US010786510B2

(12) United States Patent
Kelly et al.

(10) Patent No.: US 10,786,510 B2
(45) Date of Patent: Sep. 29, 2020

(54) METHODS OF TREATING EYE DISEASES ASSOCIATED WITH INFLAMMATION AND VASCULAR PROLIFERATION

(71) Applicant: Occurx Pty Ltd, Melbourne (AU)

(72) Inventors: Darren James Kelly, Wonga Park (AU); David Stapleton, Warrandyte (AU)

(73) Assignee: OccuRX Pty Ltd, Melbourne (AU)

( * ) Notice: Subject to any disclaimer, the term of this patent is extended or adjusted under 35 U.S.C. 154(b) by 0 days.

(21) Appl. No.: 15/807,166

(22) Filed: Nov. 8, 2017

(65) Prior Publication Data

US 2018/0117049 A1 May 3, 2018

Related U.S. Application Data

(62) Division of application No. 13/989,677, filed as application No. PCT/AU2011/001455 on Nov. 10, 2011, now Pat. No. 9,839,640.

(30) Foreign Application Priority Data

Nov. 24, 2010 (AU) ................................ 2010905197

(51) Int. Cl.

| | |
|---|---|
| *A61K 9/00* | (2006.01) |
| *A61P 27/02* | (2006.01) |
| *A61K 31/167* | (2006.01) |
| *A61K 31/5375* | (2006.01) |
| *A61K 31/192* | (2006.01) |
| *A61K 31/196* | (2006.01) |
| *A61K 31/4192* | (2006.01) |
| *A61K 31/42* | (2006.01) |
| *A61K 31/4425* | (2006.01) |
| *A61K 31/5377* | (2006.01) |
| *A61K 31/4412* | (2006.01) |

(52) U.S. Cl.

CPC ........ *A61K 31/5375* (2013.01); *A61K 9/0048* (2013.01); *A61K 31/167* (2013.01); *A61K 31/192* (2013.01); *A61K 31/196* (2013.01); *A61K 31/4192* (2013.01); *A61K 31/42* (2013.01); *A61K 31/4412* (2013.01); *A61K 31/4425* (2013.01); *A61K 31/5377* (2013.01); *A61P 27/02* (2018.01); *Y10S 514/912* (2013.01); *Y10S 514/914* (2013.01)

(58) Field of Classification Search

None

See application file for complete search history.

(56) References Cited

U.S. PATENT DOCUMENTS

| | | | |
|---|---|---|---|
| 6,114,383 | A | 9/2000 | Isaji et al. |
| 6,407,139 | B1 | 6/2002 | Isaji et al. |
| 9,839,640 | B2 | 12/2017 | Kelly et al. |
| 2007/0254055 | A1 | 11/2007 | Meydani |
| 2009/0042987 | A1 | 2/2009 | Selley |
| 2010/0158905 | A1 | 6/2010 | Pearlman et al. |
| 2018/0117050 | A1 | 5/2018 | Kelly et al. |
| 2018/0117051 | A1 | 5/2018 | Kelly et al. |

FOREIGN PATENT DOCUMENTS

| | | | |
|---|---|---|---|
| CA | 2246418 | | 8/1997 |
| CN | 1211182 | A | 3/1999 |
| EP | 0 894 496 | A1 | 2/1999 |
| EP | 0 974 352 | A1 | 1/2000 |
| JP | H09-176003 | A | 7/1997 |
| JP | H09-278653 | A | 10/1997 |
| JP | H10-259129 | A | 9/1998 |
| JP | 10330254 | | 12/1998 |
| JP | 2009-541363 | A | 11/2009 |
| WO | WO 97/29744 | A1 | 8/1997 |
| WO | WO 97/37650 | A1 | 10/1997 |
| WO | WO 98/35668 | A1 | 8/1998 |
| WO | WO 2006/073126 | A1 | 7/2006 |
| WO | WO 2008/003141 | A1 | 1/2008 |
| WO | WO 2008/131481 | A1 | 11/2008 |
| WO | WO 2009/079692 | A1 | 7/2009 |
| WO | WO 2011/047432 | A1 | 4/2011 |

OTHER PUBLICATIONS www.AMD.org, What Is AMD?, printed from http://www.amd.org/what-is-amd.html on Aug. 3, 2010, 2 pages.*

Extended European Search Report for European Application No. 11843788.8 dated Aug. 27, 2014.

International Search Report and Written Opinion from PCT/AU2011/001455 dated Jan. 20, 2012.

Afzal et al., "Targeting Retinal and Choroid Neovascularization Using the Small Molecule Inhibitor Carboxyamidotriazole", Brain Res Bull. Feb. 15, 2010; vol. 81, pp. 320-326.

Arita et al., "ROCK as a Therapeutic Target of Diabetic Retinopathy", Journal of Ophthalmology, 2010, Article ID: 175163, pp. 1-9.

Chemical Abstracts Online; Abstract Accession No. 118:93979, Itoh et al., "Effect of tranilast ophthalmic solution on allergic conjunctivitis in guinea pigs", Nippon Yakurigaku Zasshi, Jan. 1993, 101(1), pp. 27-32.

Chemical Abstracts Online; Abstract Accession No. 127:272815, WO 1997/037650 A1; Santen Pharmaceutical Co, Ltd.; Oct. 16, 1997, Okamoto et al.

Chemical Abstracts Online; Abstract Accession No. 130:105331, JP 10330254 A; Kissei Pharmaceutical Co. Ltd.; Dec. 15, 1998, Harada et al.

(Continued)

*Primary Examiner* — Gigi G Huang

(74) *Attorney, Agent, or Firm* — Wolf, Greenfield & Sacks, P.C.

(57) ABSTRACT

Methods for treating eye diseases associated with inflammation and/or vascular proliferation in subjects are disclosed. The methods include administering therapeutically effective amounts of a tranilast compound, in particular (E)-2-[[3-(3-Methoxy-4-propargyloxy)phenyl)-1-oxo-2-propenyl]amino]benzoic acid or (E)-2-[[3,4-Bis(difluoromethoxy)phenyl)-1-oxo-2-propenyl]amino]benzoic acid or pharmaceutically acceptable salts or solvates thereof.

1 Claim, 9 Drawing Sheets

Specification includes a Sequence Listing.

(56) References Cited

OTHER PUBLICATIONS

Du et al., "Effects of p38 MAPK Inhibition on Early Stages of Diabetic Retinopathy and Sensory Nerve Function", Investigative Ophthalmology & Visual Science, Apr. 2010, vol. 51, No. 4, pp. 2158-2164.

Gao, "Brief talk about diabetic eye diseases", Scientific and Technical Documentation Press, Section 41, pp. 25-26, Jul. 2002.

Miller et al., "Candesartan Attenuates Diabetic Retinal Vascular Pathology by Restoring Glyoxalase-I Function", Diabetes, 2010, vol. 59, pp. 3208-3215.

Müller et al, Fluorine in pharmaceuticals: looking beyond intuition, Science. Sep. 28, 2007;317(5846):1881-6, printed fromhttp://www.ncbi.nlm.nih.gov/pubmed/17901324, Abstract only, 1 page.

Ogita et al., Synthesis and structure-activity relationship of diarylamide derivatives as selective inhibitors of the proliferation of human coronary artery smooth muscle cells. Bioorg Med Chem Lett. Feb. 26, 2001;11(4):549-51.

Tadafumi Adachi et al., Investigative Ophthalmology & Visual Science, 2010, vol. 51, No. 8, pp. 3954-3960.

Zammit et al., Evaluation and optimization of antifibrotic activity of cinnamoyl anthranilates, Bioorg Med Chem Lett. Dec. 15, 2009;19(24):7003-6, Epub Oct. 7, 2009.

Extended European Search Report for European Application No. 18207689.3 dated Feb. 12, 2019.

Isaji et al., Tranilast inhibits the proliferation, chemotaxis and tube formation of human microvascular endothelial cells in vitro and angiogenesis in vivo. Br J Pharmacol. Nov. 1997;122(6):1061-6.

Ogawa et al., Dry eye as a major complication associated with chronic graft-versus-host disease after hematopoietic stem cell transplantation. Cornea. Oct. 2003;22(7 Suppl):S19-27. Abstract only.

* cited by examiner

SEQUENCE LISTING

<160> NUMBER OF SEQ ID NOS: 8

<210> SEQ ID NO 1
<211> LENGTH: 26
<212> TYPE: DNA
<213> ORGANISM: Artificial Sequence
<220> FEATURE:
<223> OTHER INFORMATION: Primer

<400> SEQUENCE: 1
agtgctgtac catgatcaga atacct 26

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
taaatggacg ccacgatcac 20

<210> SEQ ID NO 3
<211> LENGTH: 15
<212> TYPE: DNA
<213> ORGANISM: Artificial Sequence
<220> FEATURE:
<223> OTHER INFORMATION: Probe

<400> SEQUENCE: 3
tgatcattgc gggct 15

<210> SEQ ID NO 4
<211> LENGTH: 2602
<212> TYPE: DNA
<213> ORGANISM: Rattus norvegicus

<400> SEQUENCE: 4
ctgctgcctg cactttgccc tggtcctcca atggcttcaa cccgtgccag gcccatgctg 60
cctctgctcc tggtcctggt cgccgttgtg atccccgggc ctgtcggtgc tcaggtatcc 120
atccatccca cagaagcctt cctgcctcgg ggtggatccg tgcaggtgaa ctgctcttcc 180
tcttgcgaag acgagaacct cggcctgggg ttggagacta actggatgaa agacgaacta 240
tcgagtggac acaactggaa gctcttcaag ctgagcgaca ttggggaaga cagcagacca 300
ctgtgctttg agaactgtgg caccacgcag tcctcggctt ctgccaccat cactgtgtat 360
tcgttcccag agcgagtgga gctggatcct ctgcccgcct ggcagcaggt gggcaagaac 420
ctcatcctgc gctgcctggt ggaaggcgga gcaccgcgga cacagctctc agtagtgctg 480
ctccgtggga atgagacact gagccgccag gcagtggatg gggaccccaa ggagatcaca 540
ttcacggtgc tggccagcag aggcgaccac ggagccaatt tctcatgctt cacagaactg 600
gacctcaggc cacaagggct gtcactgttc aagaatgtct ccgaggtcag gcagctccgg 660

-continued

```
actttcgatc ttccgactag ggtcctgaag ctcgacaccc ctgacctcct ggaggtgggc    720
acccagcaga agttcttgtg ttccctggaa ggcctgtttc ctgcctctga agctcagata    780
tacctggaga tgggaggcca gatgctgacc ctggagagca caaacagcag agattttgtg    840
tcagccactg cctcagtgga ggtgactgag aagttggaca gaaccctgca gctgcgctgt    900
gttttggagc tggcggacca gaccctggag atggagaaga ccttgagaat ctacaacttt    960
tcagctccca tcctgaccct gagccagccg gaggtctcag aaggggacca agtaactgtg   1020
aagtgtgaag cccacggtgg ggcacaggtg gtgcttctga acagtacttc ccccaggcca   1080
cccacctcac agggtacttc ccccaggcca cccacctcac agatccaatt cacactgaat   1140
gccagcccgg aggatcacaa acgacgcttc ttttgctctg cggccttgga ggtggatggg   1200
aagtccctgt ttaaaaacca gaccttggaa ctccatgtgc tatatggtcc tcacctggac   1260
aagaaggact gcttggggaa ctggacctgg caagaggggt ctcagcagac tcttacatgc   1320
cagccccagg ggaatccagc ccctaatctg acctgcagcc ggaaagcaga tggtgtcccg   1380
ctgcctatcg ggatggtgaa gtctgtcaaa cgggagatga atggtaccta caagtgccgt   1440
gcctttagct cccgtgggag tatcaccagg gacgtgcacc tgacagtgct gtaccatgat   1500
cagaatacct gggtcataat tgttggtgtg ttggtactga tcattgcggg cttcgtgatc   1560
gtggcgtcca tttacaccta ttaccgccag aggaagatca ggatatacaa gttacagaag   1620
gctcaggagg aggccctaaa actcaaggta caagccccgc ctccctgagc ccactggaca   1680
ggacacctgc ctgggccccg ctgctcttga acagatcaat ggacagcatt tacccctcac   1740
ccacctcctc tggctgtcac aggacaggac agtggcctgg ggatgcatac ttgtagcctc   1800
aggcctaaga ggactcggag gggcaagact gtgaactcgt gacctggaca cacctacagc   1860
ctggtgggcc tgcagccaag aaaggctgac ttccttctct attacccctg ctgaggggcc   1920
ccctacctta ggaaggtgtg atatccggta gacacaagca agagaagaaa aggaacacca   1980
tgcttcctct gacatgggaa agctgggaca ctgtccccaa ctcttgttga tgtatttatt   2040
aattcagagt tctgacagtt atttattgag taccctgtac agacactaga ggagtgagca   2100
ggttaacatg taagttattg cctagaccct ggtgaagggg cacaacagag tctggggaaa   2160
gatcatacgg gtttgggctt ctccacaggt cagggtgctt tcctcaaaag agctgatttc   2220
tttcacgagt catataaata ctatgtggac gagcagtggc cctctgctcg tagacctctc   2280
tgggacccct gcctcctccc acagcctgga gtctcccagc accagcatgg gtgaccacct   2340
ccccacctac atacattcct acctttgttc ccaatgtcaa ccaccatgcc taaatatgga   2400
cgctcacctt tagcagctca acaatggagt ctcatgcccg tgaaattatg gtcaatccct   2460
gcatgcctcc acccggctcc acctcaaaga gaatgcctgg gagaaaatgt tccaaccact   2520
tagaagggtc ctgcaagctg ttgtgggagg gtaggcaccc ctcccagcgc agaagccttt   2580
cctttgaatc aataaagttt ta                                            2602
```

<210> SEQ ID NO 5
<211> LENGTH: 1869
<212> TYPE: DNA
<213> ORGANISM: Homo sapiens

<400> SEQUENCE: 5

```
tacctggttg atcctgccag tagcatatgc ttgtctcaaa gattaagcca tgcatgtcta     60
agtacgcacg gccggtacag tgaaactgcg aatggctcat taaatcagtt atggttcctt    120
tggtcgctcg ctcctctccc acttggataa ctgtggtaat tctagagcta atacatgccg    180
```

-continued

```
acgggcgctg accccccttcg cgggggggat gcgtgcattt atcagatcaa aaccaacccg    240
gtcagcccct ctccggcccc ggccgggggg cgggcgccgg cggctttggt gactctagat    300
aacctcgggc cgatcgcacg ccccccgtgg cggcgacgac ccattcgaac gtctgcccta    360
tcaactttcg atggtagtcg ccgtgcctac catggtgacc acgggtgacg gggaatcagg    420
gttcgattcc ggagagggag cctgagaaac ggctaccaca tccaaggaag gcagcaggcg    480
cgcaaattac ccactcccga cccggggagg tagtgacgaa aaataacaat acaggactct    540
ttcgaggccc tgtaattgga atgagtccac tttaaatcct ttaacgagga tccattggag    600
ggcaagtctg gtgccagcag ccgcggtaat tccagctcca atagcgtata ttaaagttgc    660
tgcagttaaa aagctcgtag ttggatcttg ggagcgggcg ggcggtccgc cgcgaggcga    720
gccaccgccc gtccccgccc cttgcctctc ggcgcccccct cgatgctctt agctgagtgt    780
cccgcggggc ccgaagcgtt tactttgaaa aaattagagt gttcaaagca ggcccgagcc    840
gcctggatac cgcagctagg aataatggaa taggaccgcg gttctatttt gttggttttc    900
ggaactgagg ccatgattaa gagggacggc cgggggcatt cgtattgcgc cgctagaggt    960
gaaattcttg gaccggcgca agacggacca gagcgaaagc atttgccaag aatgttttca   1020
ttaatcaaga acgaaagtcg gaggttcgaa gacgatcaga taccgtcgta gttccgacca   1080
taaacgatgc cgaccggcga tgcggcggcg ttattcccat gacccgccgg gcagcttccg   1140
ggaaaccaaa gtctttgggt tccgggggga gtatggttgc aaagctgaaa cttaaaggaa   1200
ttgacggaag ggcaccacca ggagtggagc ctgcggctta atttgactca acacgggaaa   1260
cctcacccgg cccggacacg gacaggattg acagattgat agctctttct cgattccgtg   1320
ggtggtggtg catggccgtt cttagttggt ggagcgattt gtctggttaa ttccgataac   1380
gaacgagact ctggcatgct aactagttac gcgacccccg agcggtcggc gtcccccaac   1440
ttcttagagg gacaagtggc gttcagccac ccgagattga gcaataacag gtctgtgatg   1500
cccttagatg tccggggctg cacgcgcgct acactgactg gctcagcgtg tgcctaccct   1560
acgccggcag gcgcgggtaa cccgttgaac cccattcgtg atggggatcg gggattgcaa   1620
ttattcccca tgaacgagga attcccagta agtgcgggtc ataagcttgc gttgattaag   1680
tccctgccct ttgtacacac cgcccgtcgc tactaccgat tggatggttt agtgaggccc   1740
tcggatcggc cccgccgggg tcggcccacg gccctggcgg agcgctgaga agacggtcga   1800
acttgactat ctagaggaag taaaagtcgt aacaaggttt ccgtaggtga acctgcggaa   1860
ggatcatta                                                            1869
```

<210> SEQ ID NO 6
<211> LENGTH: 3561
<212> TYPE: DNA
<213> ORGANISM: Rattus norvegicus

<400> SEQUENCE: 6

```
ttggggcagc cgagctgcag cgaggccgcg gcgctggggg cgagctgagc ggcggcagcg     60
gagctctgtc gcgagacgca gcgacaaggc agactattca acggactcat cagccaggga    120
gtctgtgctc tgggatttga tattcaaacc tctttttttt ttcttaaact gtattgtttt    180
acgctttaat ttatttttgc ttcctattcc cctcttaaat cgtgccaacg gtttggagag    240
gttgctcctt cactccctca aattacttcg gattttggaa atcagcagag gaaagaggta    300
gcaggagctc cagagagaag tcaaggaaga gagagagaga gagagaccgg tcagagagcg    360
```

-continued

```
cgctggcgag cgaacagaga gagggacagg ggcaaagtga ctgacctgct tttgggggtg    420
accgccagag cgcggcgtga gccctccccc ttgggatctt tcatcggacc agtcgcgctg    480
acggacagac agacagacac cgcccccagc cccagcgccc acctcctcgc cggcgggcag    540
ccgacggtgg acgcggcggc gagccgcgag caggagccga agcccgcgcc cggaggcggg    600
gtggaggggg tcggggctcg cgggattgca cggaaacttt tcgtccaact tctgggctct    660
tctctctccg gagtagccgt ggtctgcgcc gcaggaggca aaccgatcgg agctgggaga    720
agtgctagct cgggcctgga gaagccgggg cccgagaaga gaggggagaa agagaaggaa    780
gaggagaggg ggccgcagtg ggcgctcggc tctcgggagc cgggctcatg gacgggtgag    840
gcggcggtgt gcgcagacag tgctccagcc gcgcgcgcgc cccaggcccc ggcccgggcc    900
tcggttccag aagggagagg agcccgccaa ggcgcgcaag agagcgggct gcctcgcagt    960
ccgagccgga gagggagcgc gagccgcgcc ggccccggac gggcctctga aaccatgaac   1020
tttctgctct cttgggtgca ctggaccctg gctttactgc tgtacctcca ccatgccaag   1080
tggtcccagg ctgcacccac gacagaaggg gagcagaaag cccatgaagt ggtgaagttc   1140
atggacgtct accagcgcag ctattgccgt ccaattgaga ccctggtgga catcttccag   1200
gagtaccccg atgagataga gtatatcttc aagccgtcct gtgtgcccct aatgcggtgt   1260
gcgggctgct gcaatgatga agccctggag tgcgtgccca cgtcggagag caacgtcact   1320
atgcagatca tgcggatcaa acctcaccaa agccagcaca taggagagat gagcttcctg   1380
cagcatagca gatgtgaatg cagaccaaag aaagatagaa caaagccaga aaaaaaatca   1440
gttcgaggaa agggaaaggg tcaaaaacga aagcgcaaga aatcccggtt taaatcctgg   1500
agcgttcact gtgagccttg ttcagagcgg agaaagcatt tgtttgtcca agatccgcag   1560
acgtgtaaat gttcctgcaa aaacacagac tcgcgttgca aggcgaggca gcttgagtta   1620
aacgaacgta cttgcagatg tgacaagcca aggcggtgag ccaggctgca ggaaggagcc   1680
tccctcaggg tttcgggaac tagacctctc accggaaaga ccgattaacc atgtcaccac   1740
cacaccacca tcgtcaccgt cgacagaaca gtccttaatc cagaaagcct gacatgaagg   1800
gagaggagac tcttcgagga gcactttggg tccggagggc gagactccgg cagacgcatt   1860
cccgggcagg tgaccaagca cggtggtccc tcgtggaact ggattcgcca ttttcttata   1920
tttgctgcta aatcgccaag cccggaagat tagggagttt tgtttctggg attcctgtag   1980
acacacccac ccacatacac acacatatat atatatatat tatatatata aataaatata   2040
tatgttttat atataaaata tatatatatt cttttttttt ttaaattaac tctgctaatg   2100
ttattggtgt cttcactgga tatgtttgac tgctgtggac ttgagttggg aggaggatgt   2160
cctcacttgg atcccgacag ggaagacaat gggatgaaag actccggtgt ggtctttcgt   2220
ccttcttaga gaggccgaag tctgtttgcc tgccagggag cacgcaaggc cagggcacgg   2280
gggcacgttg gctcacttcc agaaacacga caaacccatc cctggccctg agtcaagagg   2340
acagagagac agatgacaga taaagagata aagattctgg ttccgaccag acgtttttgg   2400
ggagcctcag gacatggcac tattgtggat ccccactaga ttctgcaaga gcaccctgcc   2460
cctctgggca ctgcctggaa gaatcaggag cctggccatc aagctctctc ctccacttct   2520
gaggagccta ggaggcctcc cacaggggtc ctggcaaaga gaagacacag tggtggaaga   2580
agaggcctgg taatggctcc tcctcctcct cctgggaacc cctcgtcctc tccctacccc   2640
acttcctggg tatagctcag gaggaccttg tgtgatcaga ccattgaaac cactaattct   2700
gtccccagga gacttggctg tgtgtgtgag tggcttaccc ttccccattt tcccttccca   2760
```

```
aggtacagag caatggggca ggacccgcaa gcccctcatg gaggcagaga aaagagaaag   2820

tgttttatat acggtactta tttaatagcc ctttttaatt agaaattaaa acagttaatt   2880

taattaaaga gtagggtttt tttcagtatt cttggttaat atttaatttc aactatttat   2940

gaggatgcat ctcttgctct ttcttatttg tactgttttt ttttgttttg tttttctgtg   3000

tgtgtgtgtg tatgaaatct gtgtttccaa tctctctctc ccagatcggt gacagtcact   3060

agcttgtcct gagaagatat ttaattttgc taacactcag ctctgccctc ccctgtcccc   3120

accacacatt cctttgaaat aaggtttcaa tatacattta catactatat atatatttgg   3180

caacttgtgt ttgtatataa atatatatat atatatatgt ttatgtatat atgtgattct   3240

gataaaatag acattgctat tctgtttttt atatgtaaaa acaaaacgag aaaaaataga   3300

gaattctaca tactaaatct ctctcctttt ttaattttaa tatttgttat catttattta   3360

ttggtgctac tgtttatccg taataattgt gggggaaaag atattaacat cacgtctttg   3420

tctctagagc agttttccga gatattccgt agtacatatt tatttttaaa cagcaacaaa   3480

gaaatacaga tatatcttaa gaaaaaaaaa gcattttgta ttaaagaatt gaattctgat   3540

ctcaaaaaaa aaaaaaaaaa a                                             3561
```

<210> SEQ ID NO 7
<211> LENGTH: 3489
<212> TYPE: DNA
<213> ORGANISM: Rattus norvegicus

<400> SEQUENCE: 7

```
ttggggcagc cgagctgcag cgaggccgcg gcgctggggg cgagctgagc ggcggcagcg     60

gagctctgtc gcgagacgca gcgacaaggc agactattca acggactcat cagccaggga    120

gtctgtgctc tgggatttga tattcaaacc tctttttttt ttcttaaact gtattgtttt    180

acgctttaat ttatttttgc ttcctattcc cctcttaaat cgtgccaacg gtttggagag    240

gttgctcctt cactccctca aattacttcg gattttggaa atcagcagag gaaagaggta    300

gcaggagctc cagagagaag tcaaggaaga gagagagaga gagagaccgg tcagagagcg    360

cgctggcgag cgaacagaga gagggacagg ggcaaagtga ctgacctgct tttgggggtg    420

accgccagag cgcggcgtga gccctccccc ttgggatctt tcatcggacc agtcgcgctg    480

acggacagac agacagacac cgcccccagc cccagcgccc acctcctcgc cggcgggcag    540

ccgacggtgg acgcggcggc gagccgcgag caggagccga agcccgcgcc cggaggcggg    600

gtggaggggg tcggggctcg cgggattgca cggaaacttt tcgtccaact tctgggctct    660

tctctctccg gagtagccgt ggtctgcgcc gcaggaggca aaccgatcgg agctgggaga    720

agtgctagct cgggcctgga gaagccgggg cccgagaaga gaggggagaa agagaaggaa    780

gaggagaggg ggccgcagtg ggcgctcggc tctcgggagc cgggctcatg gacgggtgag    840

gcggcggtgt gcgcagacag tgctccagcc gcgcgcgcgc cccaggcccc ggcccgggcc    900

tcggttccag aagggagagg agcccgccaa ggcgcgcaag agagcgggct gcctcgcagt    960

ccgagccgga gagggagcgc gagccgcgcc ggccccggac gggcctctga aaccatgaac   1020

tttctgctct cttgggtgca ctggaccctg gctttactgc tgtacctcca ccatgccaag   1080

tggtcccagg ctgcacccac gacagaaggg gagcagaaag cccatgaagt ggtgaagttc   1140

atggacgtct accagcgcag ctattgccgt ccaattgaga ccctggtgga catcttccag   1200

gagtaccccg atgagataga gtatatcttc aagccgtcct gtgtgcccct aatgcggtgt   1260
```

-continued

```
gcgggctgct gcaatgatga agccctggag tgcgtgccca cgtcggagag caacgtcact   1320
atgcagatca tgcggatcaa acctcaccaa agccagcaca taggagagat gagcttcctg   1380
cagcatagca gatgtgaatg cagaccaaag aaagatagaa caaagccaga aaatcactgt   1440
gagccttgtt cagagcggag aaagcatttg tttgtccaag atccgcagac gtgtaaatgt   1500
tcctgcaaaa acacagactc gcgttgcaag gcgaggcagc ttgagttaaa cgaacgtact   1560
tgcagatgtg acaagccaag gcggtgagcc aggctgcagg aaggagcctc cctcagggtt   1620
tcgggaacta gacctctcac cggaaagacc gattaaccat gtcaccacca caccaccatc   1680
gtcaccgtcg acagaacagt ccttaatcca gaaagcctga catgaaggga gaggagactc   1740
ttcgaggagc actttgggtc cggagggcga gactccggca gacgcattcc cgggcaggtg   1800
accaagcacg gtggtccctc gtggaactgg attcgccatt ttcttatatt tgctgctaaa   1860
tcgccaagcc cggaagatta gggagttttg tttctgggat tcctgtagac acacccaccc   1920
acatacacac acatatatat atatatatta tatatataaa taaatatata tgttttatat   1980
ataaaatata tatatattct tttttttttt aaattaactc tgctaatgtt attggtgtct   2040
tcactggata tgtttgactg ctgtggactt gagttgggag gaggatgtcc tcacttggat   2100
cccgacaggg aagacaatgg gatgaaagac tccggtgtgg tctttcgtcc ttcttagaga   2160
ggccgaagtc tgtttgcctg ccagggagca cgcaaggcca gggcacgggg gcacgttggc   2220
tcacttccag aaacacgaca aacccatccc tggccctgag tcaagaggac agagagacag   2280
atgacagata aagagataaa gattctggtt ccgaccagac gtttttgggg agcctcagga   2340
catggcacta ttgtggatcc ccactagatt ctgcaagagc accctgcccc tctgggcact   2400
gcctggaaga atcaggagcc tggccatcaa gctctctcct ccacttctga ggagcctagg   2460
aggcctccca caggggtcct ggcaaagaga agacacagtg gtggaagaag aggcctggta   2520
atggctcctc ctcctcctcc tgggaacccc tcgtcctctc cctaccccac ttcctgggta   2580
tagctcagga ggaccttgtg tgatcagacc attgaaacca ctaattctgt ccccaggaga   2640
cttggctgtg tgtgtgagtg gcttaccctt ccccattttc ccttcccaag gtacagagca   2700
atggggcagg acccgcaagc ccctcatgga ggcagagaaa agagaaagtg ttttatatac   2760
ggtacttatt taatagccct ttttaattag aaattaaaac agttaattta attaaagagt   2820
agggtttttt tcagtattct tggttaatat ttaatttcaa ctatttatga ggatgcatct   2880
cttgctcttt cttatttgta ctgttttttt ttgttttgtt tttctgtgtg tgtgtgtgta   2940
tgaaatctgt gtttccaatc tctctctccc agatcggtga cagtcactag cttgtcctga   3000
gaagatattt aattttgcta acactcagct ctgccctccc ctgtccccac cacacattcc   3060
tttgaaataa ggtttcaata tacatttaca tactatatat atatttggca acttgtgttt   3120
gtatataaat atatatatat atatatgttt atgtatatat gtgattctga taaaatagac   3180
attgctattc tgttttttat atgtaaaaac aaaacgagaa aaaatagaga attctacata   3240
ctaaatctct ctcctttttt aattttaata tttgttatca tttatttatt ggtgctactg   3300
tttatccgta ataattgtgg gggaaaagat attaacatca cgtctttgtc tctagagcag   3360
ttttccgaga tattccgtag tacatattta tttttaaaca gcaacaaaga aatacagata   3420
tatcttaaga aaaaaaaagc attttgtatt aaagaattga attctgatct caaaaaaaaa   3480
aaaaaaaaa                                                            3489
```

<210> SEQ ID NO 8
<211> LENGTH: 3357

<212> TYPE: DNA
<213> ORGANISM: Rattus norvegicus

<400> SEQUENCE: 8
ttggggcagc cgagctgcag cgaggccgcg gcgctggggg cgagctgagc ggcggcagcg 60
gagctctgtc gcgagacgca gcgacaaggc agactattca acggactcat cagccaggga 120
gtctgtgctc tgggatttga tattcaaacc tctttttttt ttcttaaact gtattgtttt 180
acgctttaat ttatttttgc ttcctattcc cctcttaaat cgtgccaacg gtttggagag 240
gttgctcctt cactccctca aattacttcg gattttggaa atcagcagag gaaagaggta 300
gcaggagctc cagagagaag tcaaggaaga gagagagaga gagagaccgg tcagagagcg 360
cgctggcgag cgaacagaga gagggacagg ggcaaagtga ctgacctgct tttgggggtg 420
accgccagag cgcggcgtga gccctccccc ttgggatctt tcatcggacc agtcgcgctg 480
acggacagac agacagacac cgcccccagc cccagcgccc acctcctcgc cggcgggcag 540
ccgacggtgg acgcggcggc gagccgcgag caggagccga agcccgcgcc cggaggcggg 600
gtggaggggg tcggggctcg cgggattgca cggaaacttt tcgtccaact tctgggctct 660
tctctctccg gagtagccgt ggtctgcgcc gcaggaggca aaccgatcgg agctgggaga 720
agtgctagct cgggcctgga gaagccgggg cccgagaaga gaggggagaa agagaaggaa 780
gaggagaggg ggccgcagtg ggcgctcggc tctcgggagc cgggctcatg gacgggtgag 840
gcggcggtgt gcgcagacag tgctccagcc gcgcgcgcgc cccaggcccc ggcccgggcc 900
tcggttccag aagggagagg agcccgccaa ggcgcgcaag agagcgggct gcctcgcagt 960
ccgagccgga gagggagcgc gagccgcgcc ggccccggac gggcctctga aaccatgaac 1020
tttctgctct cttgggtgca ctggaccctg gctttactgc tgtacctcca ccatgccaag 1080
tggtcccagg ctgcacccac gacagaaggg gagcagaaag cccatgaagt ggtgaagttc 1140
atggacgtct accagcgcag ctattgccgt ccaattgaga ccctggtgga catcttccag 1200
gagtaccccg atgagataga gtatatcttc aagccgtcct gtgtgcccct aatgcggtgt 1260
gcgggctgct gcaatgatga agccctggag tgcgtgccca cgtcggagag caacgtcact 1320
atgcagatca tgcggatcaa acctcaccaa agccagcaca taggagagat gagcttcctg 1380
cagcatagca gatgtgaatg cagaccaaag aaagatagaa caaagccaga aaaatgtgac 1440
aagccaaggc ggtgagccag gctgcaggaa ggagcctccc tcagggtttc gggaactaga 1500
cctctcaccg gaaagaccga ttaaccatgt caccaccaca ccaccatcgt caccgtcgac 1560
agaacagtcc ttaatccaga aagcctgaca tgaagggaga ggagactctt cgaggagcac 1620
tttgggtccg gagggcgaga ctccggcaga cgcattcccg ggcaggtgac caagcacggt 1680
ggtccctcgt ggaactggat tcgccatttt cttatatttg ctgctaaatc gccaagcccg 1740
gaagattagg gagttttgtt tctgggattc ctgtagacac acccacccac atacacacac 1800
atatatatat atatattata tatataaata aatatatatg ttttatatat aaaatatata 1860
tatattcttt ttttttttaa attaactctg ctaatgttat tggtgtcttc actggatatg 1920
tttgactgct gtggacttga gttgggagga ggatgtcctc acttggatcc cgacagggaa 1980
gacaatggga tgaaagactc cggtgtggtc tttcgtcctt cttagagagg ccgaagtctg 2040
tttgcctgcc agggagcacg caaggccagg gcacgggggc acgttggctc acttccagaa 2100
acacgacaaa cccatccctg gccctgagtc aagaggacag agagacagat gacagataaa 2160
gagataaaga ttctggttcc gaccagacgt tttggggag cctcaggaca tggcactatt 2220

-continued

| | |
|---|---|
| gtggatcccc actagattct gcaagagcac cctgcccctc tgggcactgc ctggaagaat | 2280 |
| caggagcctg gccatcaagc tctctcctcc acttctgagg agcctaggag gcctcccaca | 2340 |
| ggggtcctgg caaagagaag acacagtggt ggaagaagag gcctggtaat ggctcctcct | 2400 |
| cctcctcctg ggaacccctc gtcctctccc taccccactt cctgggtata gctcaggagg | 2460 |
| accttgtgtg atcagaccat tgaaaccact aattctgtcc ccaggagact tggctgtgtg | 2520 |
| tgtgagtggc ttacccttcc ccattttccc ttcccaaggt acagagcaat ggggcaggac | 2580 |
| ccgcaagccc ctcatggagg cagagaaaag agaaagtgtt ttatatacgg tacttattta | 2640 |
| atagcccttt ttaattagaa attaaaacag ttaatttaat taaagagtag ggtttttttc | 2700 |
| agtattcttg gttaatattt aatttcaact atttatgagg atgcatctct tgctctttct | 2760 |
| tatttgtact gttttttttt gttttgtttt tctgtgtgtg tgtgtgtatg aaatctgtgt | 2820 |
| ttccaatctc tctctcccag atcggtgaca gtcactagct tgtcctgaga agatatttaa | 2880 |
| ttttgctaac actcagctct gccctcccct gtccccacca cacattcctt tgaaataagg | 2940 |
| tttcaatata catttacata ctatatatat atttggcaac ttgtgtttgt atataaatat | 3000 |
| atatatatat atatgtttat gtatatatgt gattctgata aaatagacat tgctattctg | 3060 |
| ttttttatat gtaaaaacaa aacgagaaaa aatagagaat tctacatact aaatctctct | 3120 |
| cctttttttaa ttttaatatt tgttatcatt tatttattgg tgctactgtt tatccgtaat | 3180 |
| aattgtgggg gaaaagatat taacatcacg tctttgtctc tagagcagtt ttccgagata | 3240 |
| ttccgtagta catatttatt tttaaacagc aacaaagaaa tacagatata tcttaagaaa | 3300 |
| aaaaaagcat tttgtattaa agaattgaat tctgatctca aaaaaaaaaa aaaaaaa | 3357 |

METHODS OF TREATING EYE DISEASES ASSOCIATED WITH INFLAMMATION AND VASCULAR PROLIFERATION

RELATED APPLICATIONS

The present application is a Divisional Application of U.S. application Ser. No. 13/989,677, filed May 24, 2013, which is a National Stage filing under 35 U.S.C. 371 of International Application No. PCT/AU2011/001455, filed Nov. 10, 2011, entitled "METHODS OF TREATING EYE DISEASES ASSOCIATED WITH INFLAMMATION AND VASCULAR PROLIFERATION," which claims priority to Australian Patent Application No. 2010905197, filed Nov. 24, 2010, each incorporated herein by reference for all purposes.

FIELD OF THE INVENTION

The present invention relates broadly to methods of treating eye diseases associated with inflammation and/or vascular proliferation including diabetic retinopathy. More particularly, the invention relates to a method of treating these eye diseases with analogues of the anti-fibrotic agent, Tranilast, as well as a kit for treating these eye diseases.

BACKGROUND OF THE INVENTION

Ocular diseases that involve inflammation and/or vascular proliferation as a causal element(s) usually, but not always, relate to the anterior- and posterior-segments of the eye. For example, ocular disorders that have an etiology in inflammation and/or vascular proliferation could be corneal edema, anterior and posterior uveitis, pterygium, corneal diseases that are caused by infections from microbes or microorganisms such as bacteria, viruses, fungi, amoebas and parasites, dry eye, conjunctivitis, allergy- and laser-induced exudation, non-age related macular degeneration, macular edema, diabetic retinopathy (DR), age-related macular degeneration (Kim et al. 2001; A. M. Joussen et al. 2004; S. C. Pflugfelder 2004) and ocular von Hippel-Lindau disease which is characterised by fine vascular proliferation in the retina.

One of the ocular diseases mentioned above, DR, is a common complication of diabetes and remains one of the leading causes of vision loss (Cheung, Fung et al. 2005; Santos, Tschiedel et al. 2005). Vision loss in DR develops by slow and progressive alterations to the retinal microvasculature (pericytes and endothelial cells) leading to breakdown of the blood-retinal barrier, pathological angiogenesis and scarring. Based on the extent of vascular abnormalities, DR can be broadly categorized into non-proliferative DR (NPDR) and proliferative DR (PDR) (Klein, Klein et al. 2004). In NPDR, hyperglycaemia induces thickening of capillary basement membrane, apoptosis or 'dropout' of pericytes, microaneurysms and vascular leakage. Blockade of retinal capillaries causes localized hypoxia, which increases the production of angiogenic growth factors. In some microvessels, endothelial cells become apoptotic resulting in acellular capillaries (devoid of both pericytes and endothelial cells), capillary closure and areas of retinal non-perfusion. Adherent leukocytes may also contribute to the lesion by causing retinal capillary occlusion (Joussen, Poulaki et al. 2004). Multiple haemorrhages, soft exudates, cotton wool spots, intraretinal microvascular abnormalities and venous beading and loops develop. Increased areas of tissue non-perfusion stimulate the production of angiogenic factors leading to the proliferation of vessels, which is the hallmark feature of PDR. Retinal angiogenesis can be accompanied by fibrosis resulting in a fibrovascular ridge, which extends into the vitreous cavity or on the surface of the retina. Contraction of the fibrovascular ridge causes retinal detachment and vision loss and blindness (Watkins 2003).

The pathogenesis of DR is not fully understood. However, metabolic and biochemical changes, such as increased flux of glucose through the polyol pathway, activation of protein kinase C, oxidative damage and increased advanced glycation endproduct formations are contributors in the development of DR (Cheung, Fung et al. 2005). Accumulating evidences indicate that vascular endothelial growth factor (VEGF) plays a critical role in angiogenesis (Sarlos, Rizkalla et al. 2003) in DR, while intercellular adhesion molecule (ICAM-1) mediated leukocytosis resulting in secondary endothelial damage (Joussen, Poulaki et al. 2002; Khalfaoui, Lizard et al. 2009). Recently, DR has also been recognized as a chronic inflammatory disease (Adamis 2002; Joussen, Poulaki et al. 2004). With this notion, studies demonstrated that anti-inflammatory therapy prevents classic histopathological features of DR: acellular capillary formation, retinal haemorrhage development, microaneurysm progress, and pericyte loss (Adamis 2002; Joussen, Poulaki et al. 2002).

The current treatment for DR is laser photocoagulation, a procedure that destroys angiogenic vessels and the surrounding hypoxic tissue (Aiello 2003).

Although beneficial, laser photocoagulation can destroy healthy retina, and the disease continues despite intensive treatment. Therefore, less invasive therapies are being investigated, with a particular focus on the inhibition of injurious molecules such as VEGF and ICAM-1 (Arita, Hata et al.; Sarlos, Rizkalla et al. 2003; Khalfaoui, Lizard et al. 2009). Nevertheless, there remains a need for further therapies for treating eye diseases associated with inflammation and/or vascular proliferation such as diabetic retinopathy as well as corneal edema, anterior and posterior uveitis, pterygium, corneal diseases that are caused by infections from microbes or microorganisms such as bacteria, viruses, fungi, amoebas and parasites, dry eye, conjunctivitis, allergy- and laser-induced exudation, non-age related macular degeneration, macular edema, age-related macular degeneration and ocular von Hippel-Lindau disease.

The reference to any prior art in this specification is not, and should not be taken as an acknowledgement or any form of suggestion that the referenced prior art forms part of the common general knowledge in Australia.

SUMMARY OF THE INVENTION

In a first aspect, the present invention provides a method for treating an eye disease associated with inflammation and/or vascular proliferation in a subject including administering to the subject a therapeutically effective amount of a tranilast compound, or a pharmaceutically acceptable salt or solvate thereof.

As used herein, the term "tranilast compound" refers to tranilast per se or a compound that one of ordinary skill in the art would understand as a derivative or analogue thereof such as the compounds of formulae 1 to 20 described below. However, the term is not intended to limit the present invention to tranilast per se or compounds of formulae 1 to 20 as other derivatives or analogues may also be suitable for use in the present invention.

However, as with any group of structurally related compounds which possess a particular utility, certain tranilast compounds may be particularly useful in the present invention.

In some embodiments of the first aspect of the invention, the tranilast compound is a compound of Formula 1

Formula 1

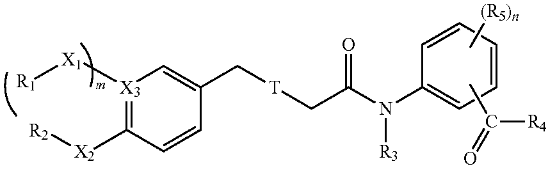

wherein $R_1$ and $R_2$, which may be the same or different, are selected from the group consisting of H, $NHR_6$, $NR_6R_7$, $OR_8$, halogen, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, fused $C_5$ to $C_{20}$ aryl or alkaryl, and a hydrocarbon chain containing a heterocyclic or fused ring, any of which may be optionally substituted;

$R_3$ is selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted;

$R_4$ is selected from the group consisting of H, OH, $OR_6$, $NHR_6$ and $NR_6R_7$;

$R_5$ is selected from the group consisting of H, $NHR_6$, $NR_6R_7$, $OR_8$, halogen, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, fused $C_5$ to $C_{20}$ aryl or alkaryl, and a hydrocarbon chain containing a heterocyclic or fused ring, any of which may be optionally substituted;

$X_1$ and $X_2$, which may be the same or different, are selected from the group consisting of a bond, C, O, N and S;

$X_3$ is C or N;

T is a single or double bond;

m is the integer 0 or 1;

n is an integer between 0 and 4;

$R_6$ and $R_7$, which may be the same or different, are selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted;

$R_8$ is selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted;

or derivatives thereof, analogues thereof, pharmaceutically acceptable salts thereof, or metabolites thereof.

In some embodiments of the first aspect of the invention, the tranilast compound is a compound of Formula 2

Formula 2

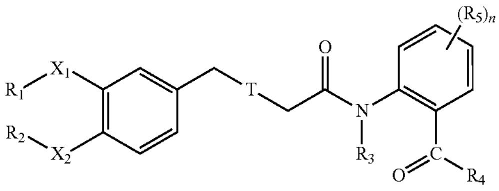

wherein $R_1$ and $R_2$, which may be the same or different, are selected from the group consisting of a $C_1$ to $C_{10}$ alkyl, $C_3$ to $C_{o1}$ cycloalkyl, $C_3$ to $C_{10}$ cycloalkylmethyl, $C_3$ to $C_{10}$ alkene, $C_3$ to $C_{10}$ alkyne and a chain containing a heterocyclic or fused ring, any of which may be optionally substituted;

$X_1$ and $X_2$ are the same or different and are selected from the group consisting of a bond, O, N and S;

T is a single or double bond;

$R_3$ is selected from the group consisting of H, $C_3$ to $C_{10}$ alkene, $C_3$ to $C_{10}$ alkyne and a chain containing a heterocyclic or fused ring, any of which may be optionally substituted;

$R_4$ is selected from the group consisting of H, OH, $OR_6$, $NHR_6$ and $NR_6R_7$;

$R_5$ is selected from the group consisting of H, $NHR_6$, $NR_6R_7$, $OR_8$, halogen, $C_3$ to $C_{10}$ alkene, $C_3$ to $C_{10}$ alkyne and a chain consisting of a heterocyclic or fused ring, any of which may be optionally substituted;

$R_6$ and $R_7$, which may be the same or different, are selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing, a heterocyclic or fused ring, any of which may be optionally substituted;

$R_8$ is selected from the group consisting of H, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, and a hydrocarbon chain containing a heterocyclic or fused ring, any of which may be optionally substituted; and n is an integer between 0 and 4;

or derivatives thereof, analogues thereof, pharmaceutically acceptable salts thereof and metabolites thereof.

In another embodiment of the first aspect of the invention, the tranilast compound is a compound of Formula 3

Formula 3

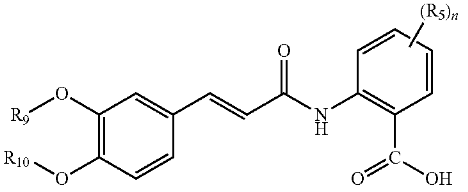

wherein $R_9$ or $R_{10}$, which may be the same or different, are selected from the group consisting of H, $C_1$ to $C_{10}$ alkyl, $C_3$ to $C_8$ terminal or non-terminal alkyne or a cyclopentyl, cyclohexyl, cyclohexylmethyl or cyclopentylmethyl group;

$R_5$ and n are as described above in respect of formulae 1 and 2;

or derivatives thereof, analogues thereof, pharmaceutically acceptable salts thereof, and metabolites thereof.

In some embodiments of the first aspect of the invention, the tranilast compound is a compound of Formula 4 or Formula 5

Formula 4

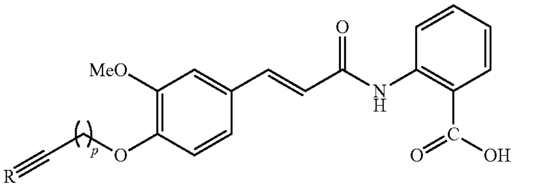

Formula 5

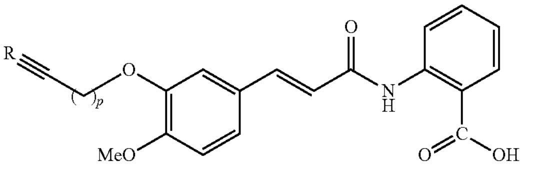

where p is an integer between 1 and 10; and R is selected from the group consisting of H and $C_1$ to $C_{10}$ alkyl;

or derivatives thereof, analogues thereof, pharmaceutically acceptable salts thereof, and metabolites thereof.

In yet another embodiment of the first aspect of the invention, the tranilast compound is a compound of Formula 6 or Formula 7

Formula 6

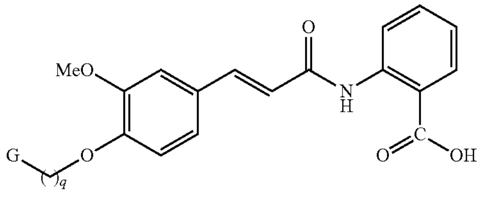

Formula 7

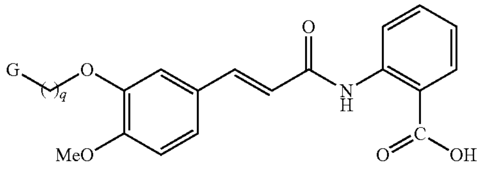

wherein G is a cyclopentyl ring, a cyclohexyl ring or a 1,4-disubstituted 1,2,3-triazole ring; and q is an integer between 0 and 6;

or derivatives thereof, analogues thereof, pharmaceutically acceptable salts thereof, and metabolites thereof.

Non-limiting examples of suitable tranilast compounds of formulae 1 to 7 as described above include:

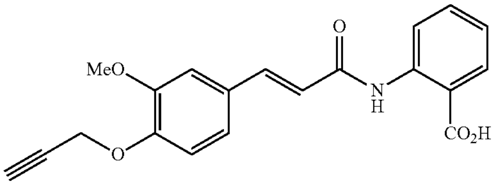

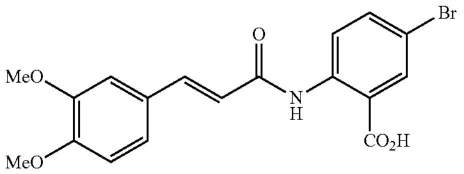

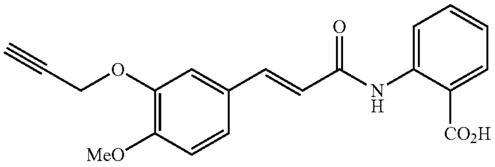

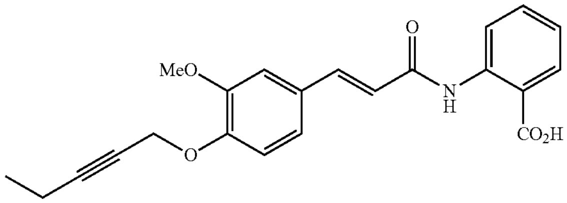

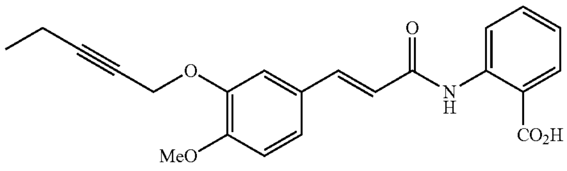

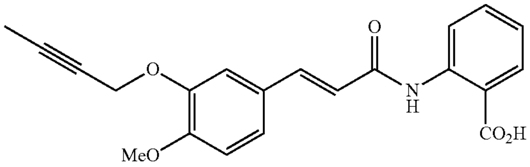

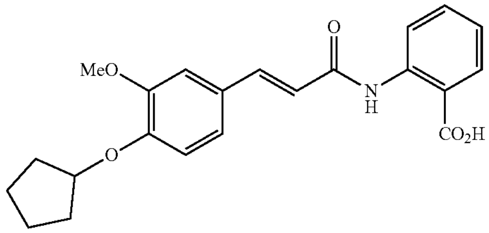

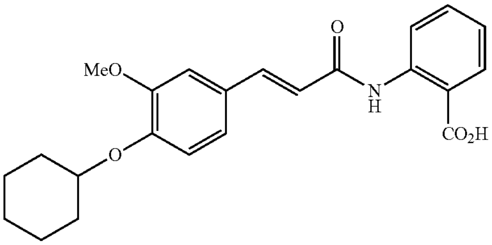

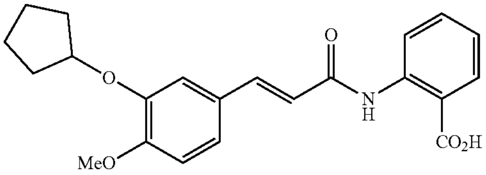

-continued
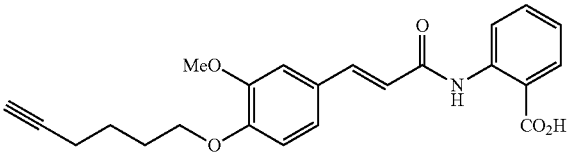
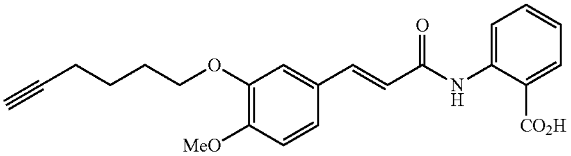
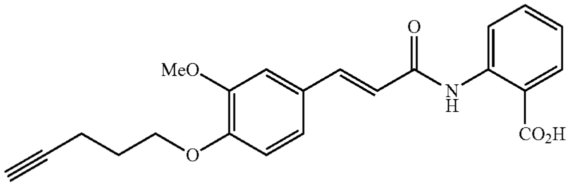
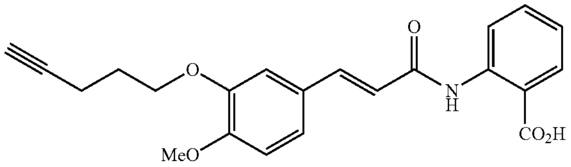
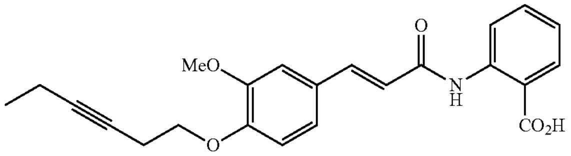
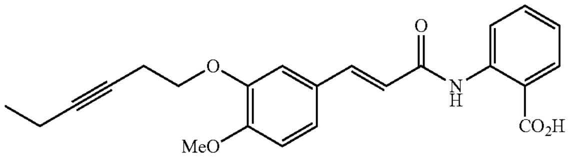
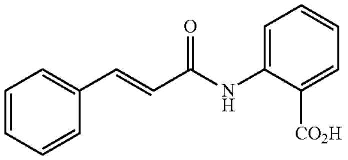
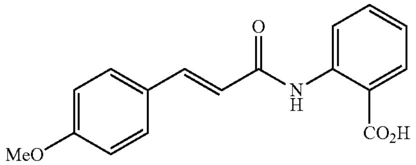
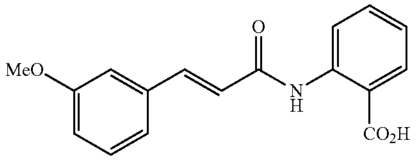
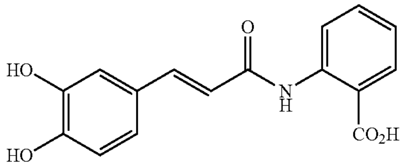
-continued
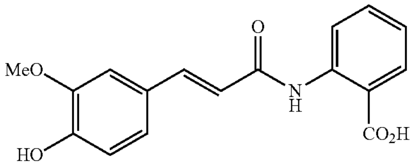
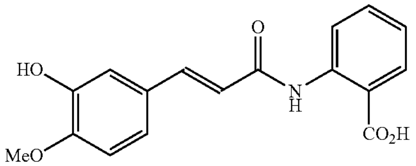
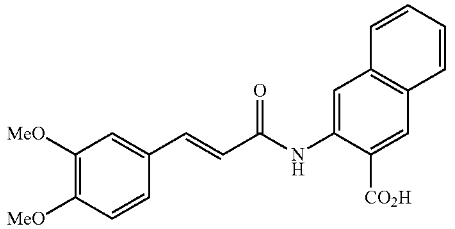
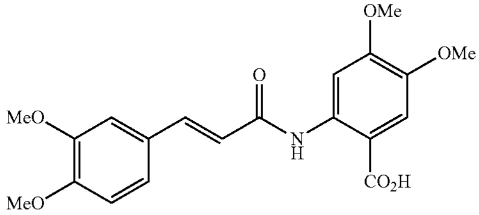
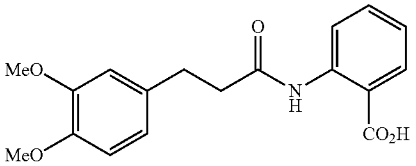
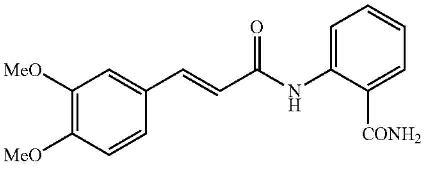
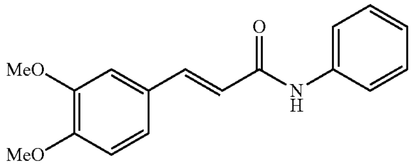
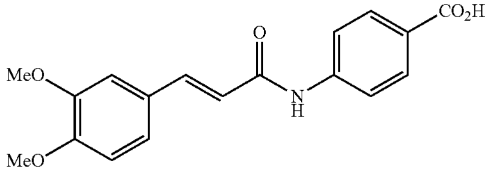
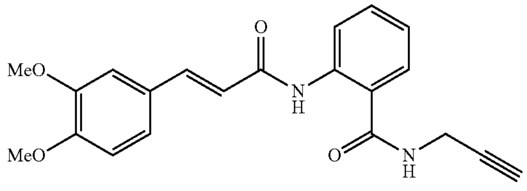

-continued
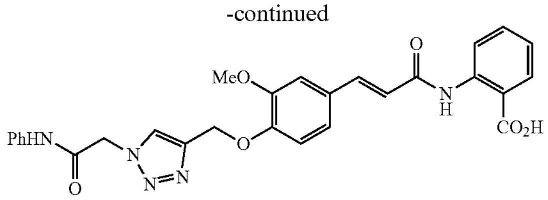
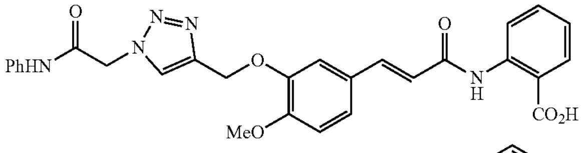
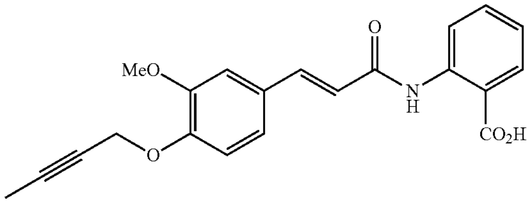
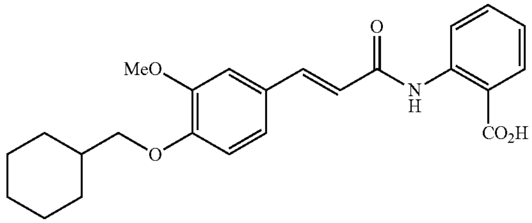
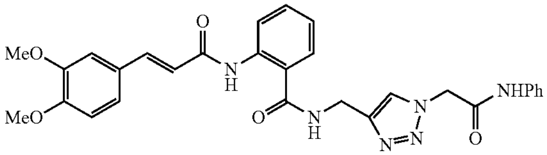
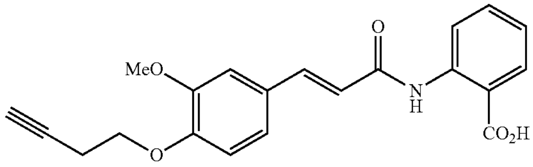
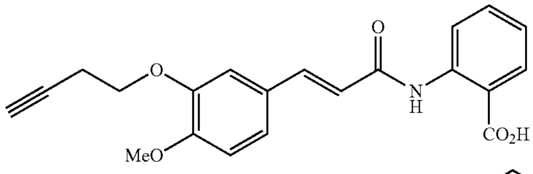
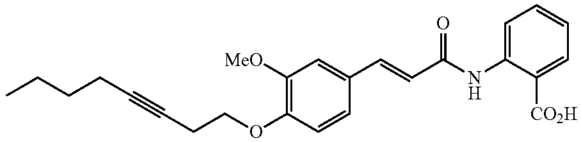
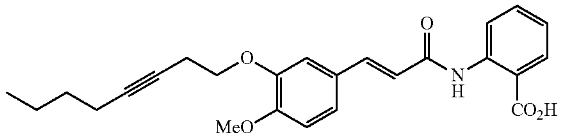
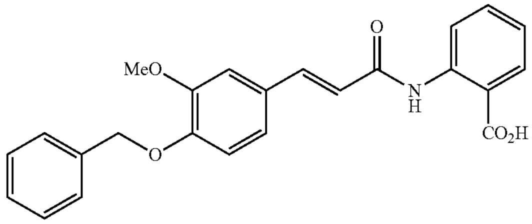
-continued
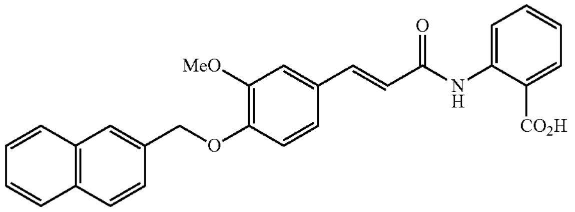
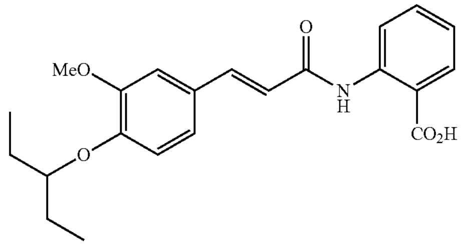
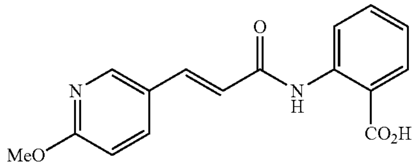
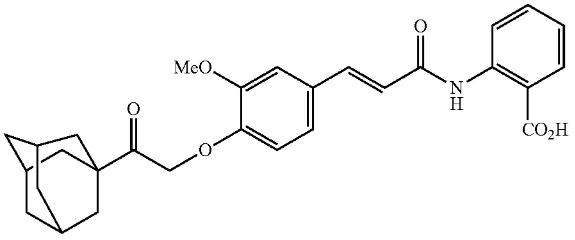
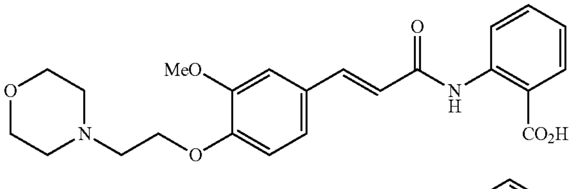
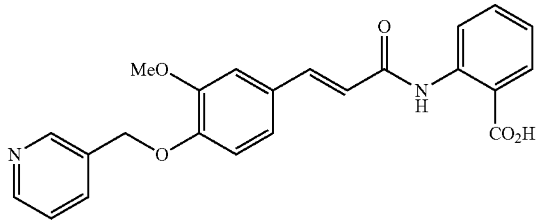
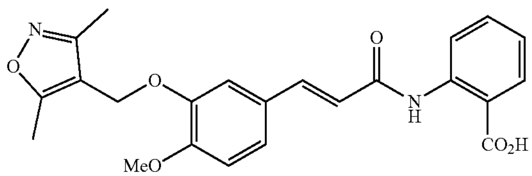
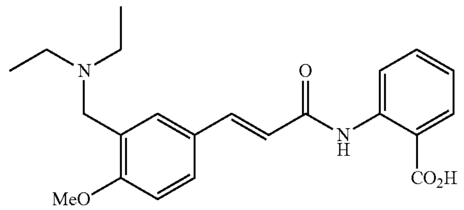

-continued
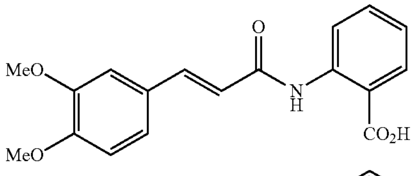
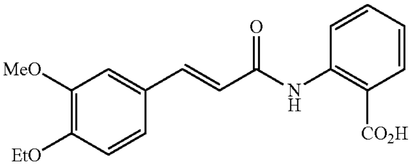
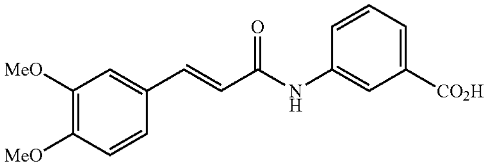
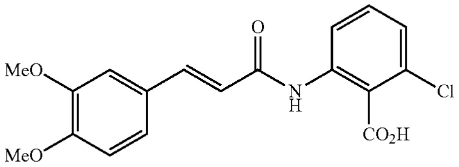
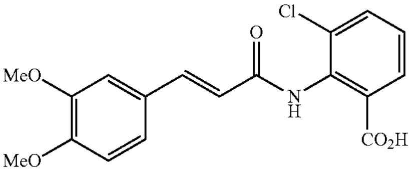
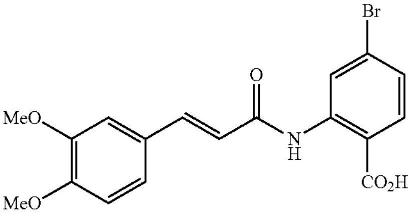
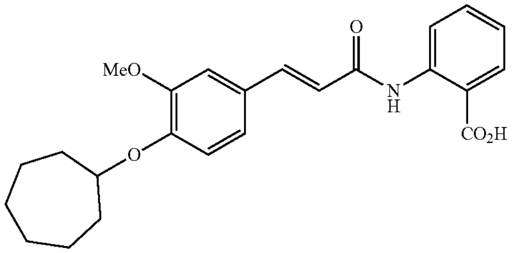
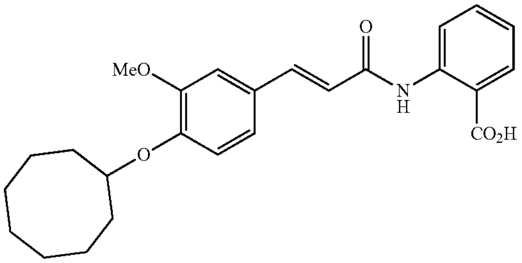
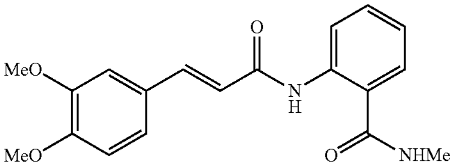
-continued
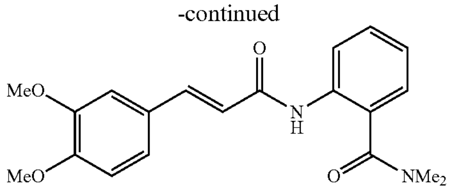
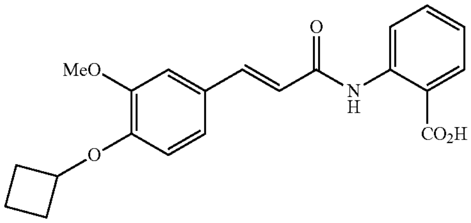
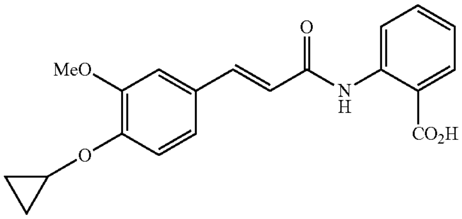
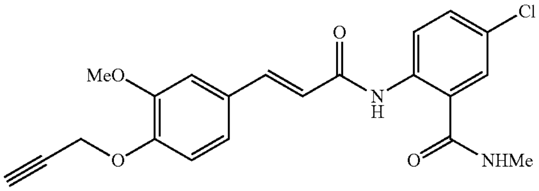
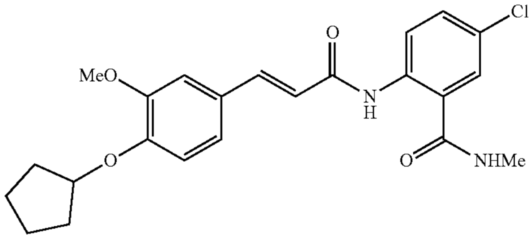
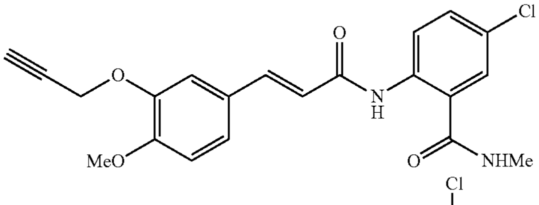
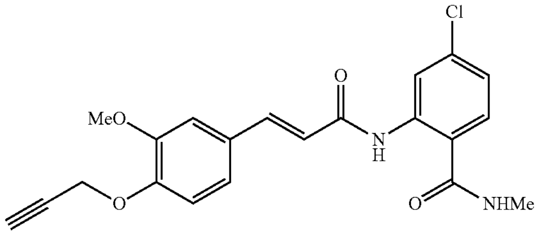
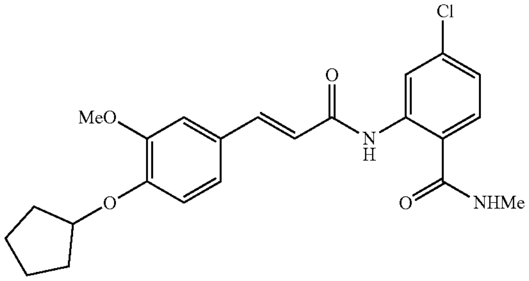

-continued

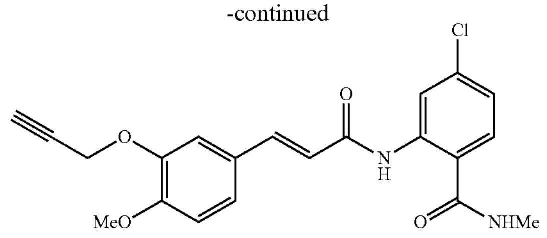

or derivatives thereof, analogues thereof, pharmaceutically acceptable salts thereof, and metabolites thereof.

In a preferred embodiment of the first aspect of the present invention, the tranilast compound has the formula

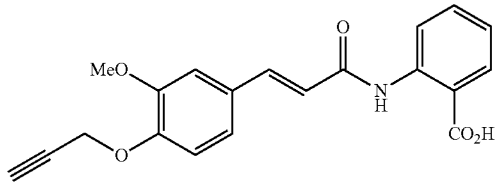 [SMILES: C#CCOc1ccc(/C=C/C(=O)Nc2ccccc2C(=O)O)cc1OC]

or a pharmaceutically acceptable salt thereof.

In alternate embodiments of the first aspect of the invention, the tranilast compound has the formula 8

Formula 8

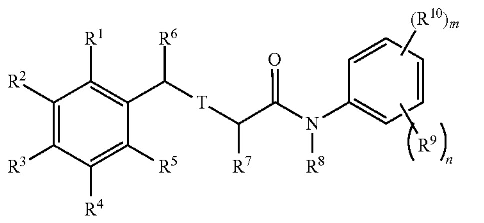

wherein:

T is a single bond, a double bond or a triple bond;

$R^1$, $R^2$, $R^3$, $R^4$, and $R^5$ are each independently selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, COOH, $COOR^{11}$, $CONR^{11}R^{12}$, $NR^{11}COR^{12}$, $NR^{11}COOR^{12}$, $NR^{11}SO_2R^{12}$, $NR^{11}CONR^{12}R^{13}$, $NR^{11}R^{12}$, and acyl; provided that at least one of $R^1$, $R^2$, $R^3$, $R^4$, and $R^5$ contains a halogen;

$R^6$ and $R^7$ are present when T is a single bond or a double bond but not when T is a triple bond, each $R^6$ and $R^7$ being independently selected from the group consisting of: H, $NO_2$, CN, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, COOH, $COOR^{11}$, $CONR^{11}R^{12}$, $NR^{11}COR^{12}$, $NR^{11}COR^{12}$, $NR^{11}SO_2R^{12}$, $NR^{11}CONR^{12}R^{13}$, $NR^{11}R^{12}$, and acyl;

$R^8$ is selected from the group consisting of: H, a N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

$R^9$ is selected from the group consisting of: H, $COOR^{11}$, $CONR^{11}R^{12}$, $COSR^{11}$, $OR^{11}$, $NR^{11}R^{12}$, and $SR^{11}$;

$R^{10}$ is selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, COOH, $COOR^{11}$, $CONR^{11}R^{12}$, $NR^{11}COR^{12}$, $NR^{11}COOR^{12}$, $NR^{11}SO_2R^{12}$, $NR^{11}CONR^{12}R^{13}$, $NR^{11}R^{12}$, and acyl;

each $R^{11}$, $R^{12}$ and $R^{13}$ is independently selected from the group consisting of H, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

m is an integer selected from the group consisting of 0, 1, 2, 3, and 4;

n is an integer selected from the group consisting of 1, 2, 3, and 4, and 5; and m+n is an integer selected from the group consisting of 1, 2, 3, 4, and 5;

or derivatives thereof, analogues thereof, pharmaceutically acceptable salts thereof, and metabolites thereof.

In a preferred embodiment of the first aspect of the invention, the tranilast compound of formula 8 described immediately above has the formula 9

Formula 9

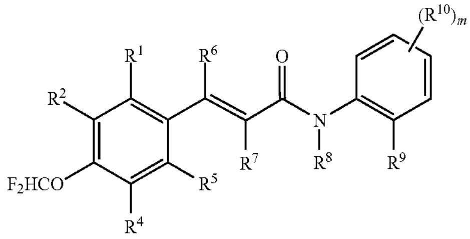

or derivatives thereof, analogues thereof, pharmaceutically acceptable salts thereof, and metabolites thereof.

In another preferred embodiment of the first aspect of the invention, the tranilast compound of formula 8 described above has the formula 10

Formula 10

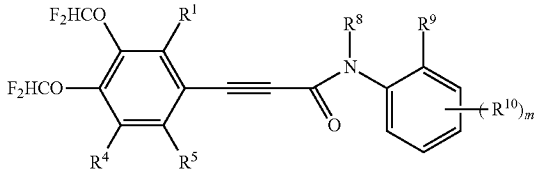

or derivatives thereof, analogues thereof, pharmaceutically acceptable salts thereof, and metabolites thereof.

Non-limiting examples of suitable tranilast compounds of formulae 8 to 10 as described above include:

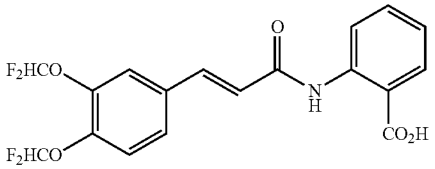

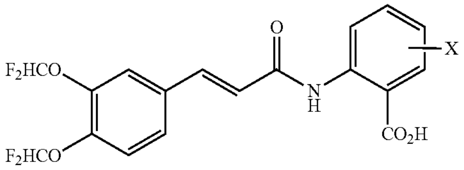

X = Cl, Br

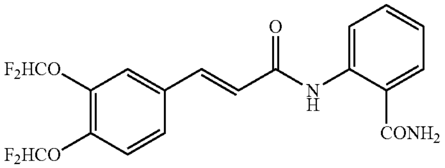

-continued

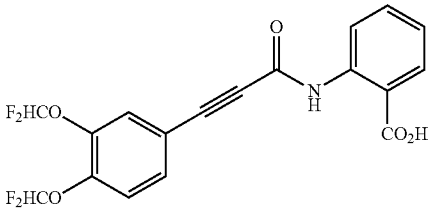

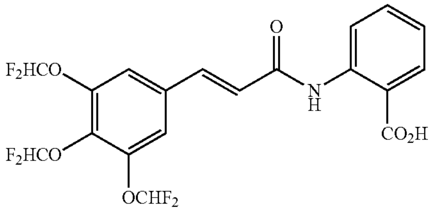

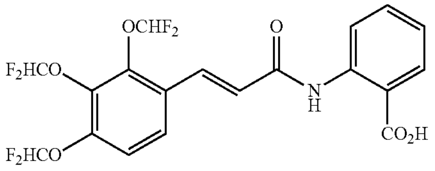

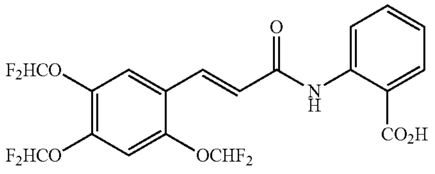

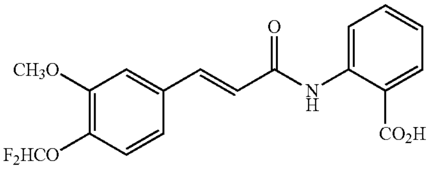

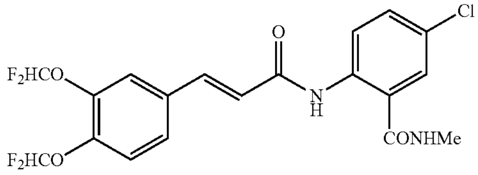

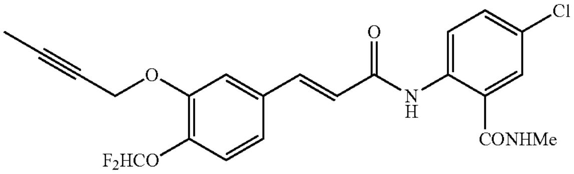

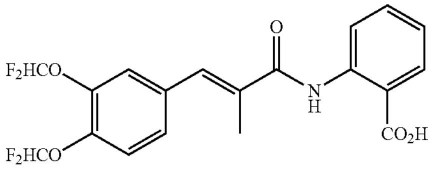

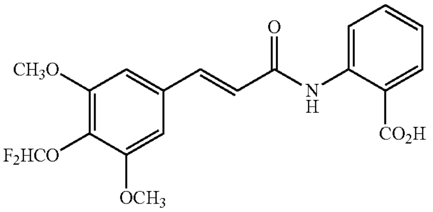

-continued

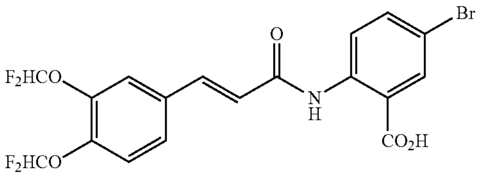

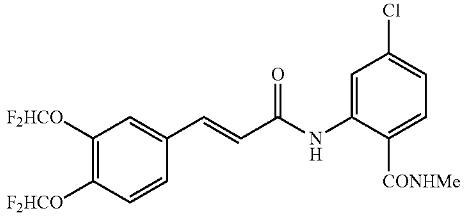

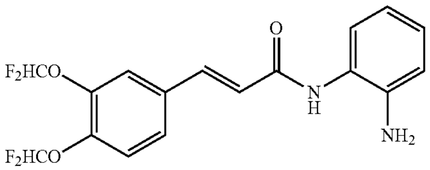

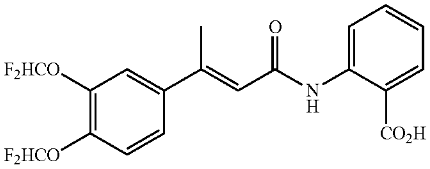

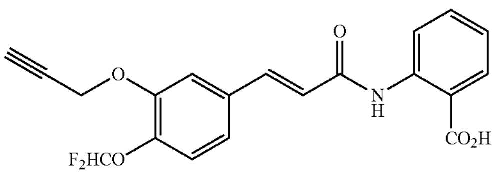

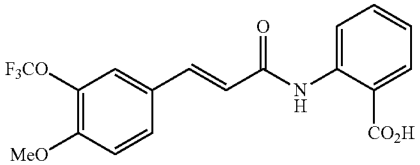

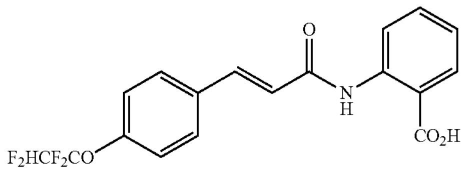

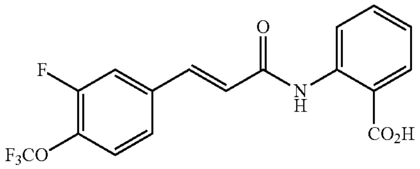

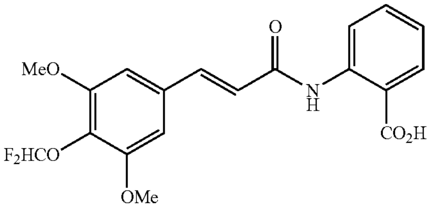

or a pharmaceutically acceptable salt thereof.

In a preferred embodiment of the first aspect of the present invention, the tranilast compound has the formula

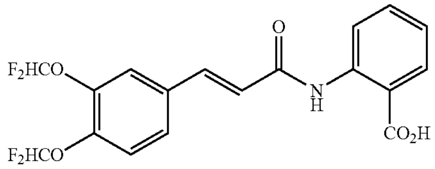

or a pharmaceutically acceptable salt thereof.

In some embodiments of the first aspect of the invention, the tranilast compound has the formula 11

Formula 11

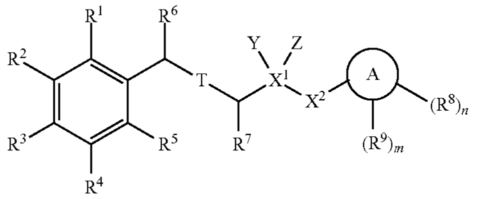

wherein;

$X^1(YZ)$ is C═O, $C(F_2)$ or $SO_2$;

$X^2$ is $NR^{10}$ or $(CH_2)_p$;

T is a double bond, a triple bond or when T is a single bond, one pair of $R^6$ and $R^7$ are fused to form a cyclopropane ring of the formula

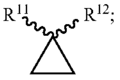

A is selected from the group consisting of $C_3$ to $C_{12}$ cycloalkyl, $C_3$ to $C_{12}$ cycloalkenyl, $C_1$ to $C_{12}$ heterocycloalkyl, $C_1$ to $C_{12}$ heterocycloalkenyl, $C_6$-$C_{18}$ aryl and $C_6$ to $C_{18}$ heteroaryl;

$R^1$, $R^4$ and $R^5$ are each independently selected from the group consisting of: H, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{13}$, $SO_3H$, $SO_2NR^{13}R^{14}$, $SO_2R^{13}$, $SONR^{13}R^{14}$, $SOR^{13}$, $COR^{13}$, COOH, $COOR^{13}$, $CONR^{13}R^{14}$, $NR^{13}COR^{14}$, $NR^{13}COOR^{14}$, $NR^{13}SO_2R^{14}$, $NR^{13}CONR^{14}R^{15}$, $NR^{13}R^{14}$, and acyl;

$R^2$ and $R^3$, are each independently selected from the group consisting of: H, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{13}$, $SO_3H$, $SO_2NR^{13}R^{14}$, $SO_2R^{13}$, $SONR^{13}R^{14}$, $SOR^{13}$, $COR^{13}$, COOH, $COOR^{13}$, $CONR^{13}R^{14}$, $NR^{13}COR^{14}$, $NR^{13}COOR^{14}$, $NR^{13}SO_2R^{14}$, $NR^{13}CONR^{14}R^{15}$, $NR^{13}R^{14}$ and acyl; or $R^2$ and $R^3$ may be fused to form a 5 or 6 membered cycloalkyl, heterocycloalkyl, aryl or heteroaryl ring each of which may be optionally substituted;

one pair of $R^6$ and $R^7$ are present when T is a double bond but $R^6$ and $R^7$ are not present when T is a triple bond, each $R^6$ and $R^7$ being independently selected from the group consisting of: H, $NO_2$, CN, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{13}$, $SO_3H$, $SO_2NR^{13}R^{14}$, $SO_2R^{13}$, $SONR^{13}R^{14}$, $SOR^{13}$, $COR^{14}$, COOH, $COOR^{13}$, $CONR^{13}R^{14}$, $NR^{13}COR^{14}$, $NR^{13}COOR^{14}$, $NR^{13}SO_2R^{14}$, $NR^{13}CONR^{14}R^{15}$, $NR^{13}R^{14}$, and acyl;

$R^8$ is selected from the group consisting of H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{13}$, $SO_3H$, $SO_2NR^{13}R^{14}$, $SO_2R^{13}$, $SONR^{13}R^{14}$, $SOR^{13}$, $COR^{13}$, COOH, $COOR^{13}$, $CONR^{13}R^{14}$, $NR^{13}COR^{14}$, $NR^{13}COOR^{14}$, $NR^{13}SO_2R^{14}$, $NR^{13}CONR^{14}R^{15}$ and $NR^{13}R^{14}$ and acyl;

$R^9$ is selected from the group consisting of OH, $OR^{13}$, $COOR^{13}$, $CONR^{13}R^{14}$, $NR^{13}R^{14}$, tetrazol-5-yl, $SO_2R^{13}$, $SO_2NR^{13}R^{14}$ and $CONHOR^{13}$;

$R^{10}$ is selected from the group consisting of H, a N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$aryl, and optionally substituted $C_1$-$C_{18}$heteroaryl;

$R^{11}$ and $R^{12}$ are independently selected from the group consisting of H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{13}$, $SO_3H$, $SO_2NR^{13}R^{14}$, $SO_2R^{13}$, $SONR^{13}R^{14}$, $SOR^{13}$, $COR^{13}$, COOH, $COOR^{13}$, $CONR^{13}R^{14}$, $NR^{13}COR^{14}$, $NR^{13}COOR^{14}$, $NR^{13}SO_2R^{14}$, $NR^{13}CONR^{14}R^{15}$, $NR^{13}R^{14}$, and acyl;

each $R^{13}$, $R^{14}$, $R^{15}$ are each independently selected from the group consisting of H, —OH, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl; optionally substituted $C_1$-$C_{12}$ heterocycloalkyl, optionally substituted $C_1$-$C_{12}$ heterocycloalkenyl, optionally substituted $C_6$-$C_{18}$aryl, and optionally substituted $C_1$-$C_{18}$heteroaryl;

n is an integer selected from the group consisting of 0, 1, 2, 3, and 4;

m is an integer selected from the group consisting of 1, 2, 3, and 4;

m+n is an integer selected from the group consisting of 1, 2, 3, 4, and 5; and p is an integer selected from the group consisting of 0, 1, 2, 3, 4, and 5;

and when $X^1(YZ)$ is $C(F_2)$ or $SO_2$; or when T is a cyclopropane ring as defined above; or when $R^1$ and $R^5$ are H and T is a double bond; or when $X^2$ is $(CH_2)_p$ and p is 0 or 1; or when A is selected from the group consisting of $C_3$ to $C_{12}$ cycloalkyl, preferably $C_4$ to $C_6$ cycloalkyl, $C_1$ to $C_{12}$ heterocycloalkenyl, and $C_6$ to $C_{18}$ heteroaryl;

then $R^2$ and $R^3$ may also be independently selected from —$X^3$—$R^{16}$ or —$X^4$—$R^{17}$;

wherein $X^3$ and $X^4$ may be the same or different and are selected from the group consisting of a bond C, O, N and S; and $R^{16}$ and $R^{17}$ may be the same or different and are selected from the group consisting of H, $NHR^{13}$, $NR^{13}R^{14}$, $OR^{13}$, halogen, $C_1$ to $C_{10}$ alkyl, $C_3$ to $C_{10}$ cycloalkyl, $C_3$ to $C_{10}$ cycloalkylmethyl, $C_3$ to $C_{10}$ alkene, $C_3$ to $C_{10}$ alkyne, aryl, $C_5$ to $C_{20}$ alkaryl, fused $C_5$ to $C_{20}$ aryl or alkaryl and a hydrocarbon chain containing a heterocyclic or fused ring, any of which may be optionally substituted;

or derivatives thereof, analogues thereof, pharmaceutically acceptable salts thereof, and metabolites thereof.

In a preferred embodiment of the first aspect of the invention, the tranilast compound of formula 11 described above has the formula 12

Formula 12

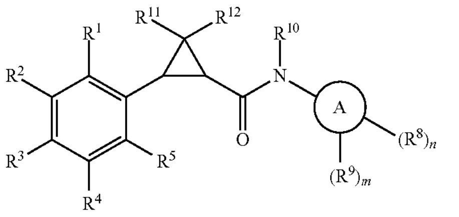

or derivatives thereof, analogues thereof, pharmaceutically acceptable salts thereof, and metabolites thereof.

In another preferred embodiment of the first aspect of the invention, the tranilast compound of formula 11 described above has the formula 13

Formula 13

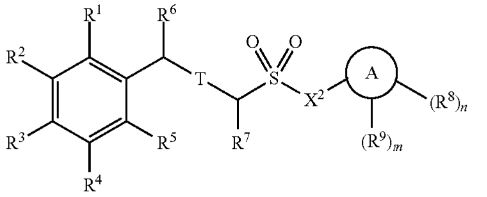

or derivatives thereof, analogues thereof, pharmaceutically acceptable salts thereof, and metabolites thereof.

In yet another preferred embodiment of the first aspect of the invention, the tranilast compound of formula 11 described above has the formula 14

Formula 14

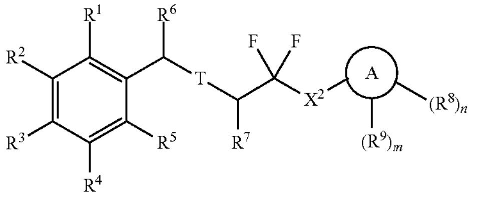

or derivatives thereof, analogues thereof, pharmaceutically acceptable salts thereof, and metabolites thereof.

In another embodiment of the first aspect of the invention, the tranilast compound of formula 11 described above has the formula 15

Formula 15

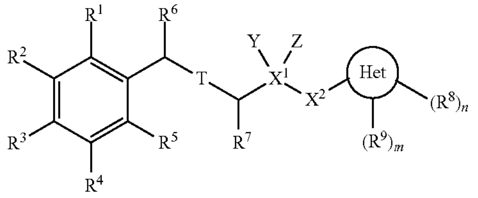

wherein Het represents a heterocyclic ring;

or derivatives thereof, analogues thereof, pharmaceutically acceptable salts thereof, and metabolites thereof.

In some embodiments of the first aspect of the invention, the tranilast compound of formula 11 described above has the formula 16

Formula 16

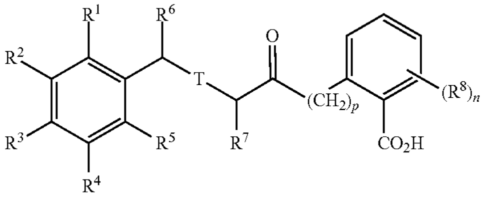

or derivatives thereof, analogues thereof, pharmaceutically acceptable salts thereof, and metabolites thereof.

Non-limiting examples of suitable tranilast compounds of formulae 11 and 12 as described above include:

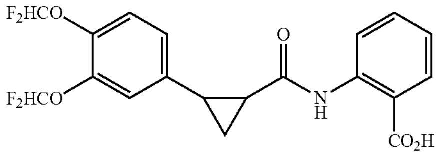

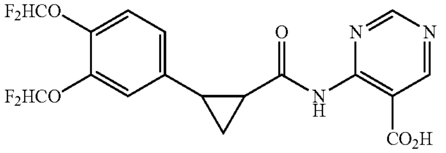

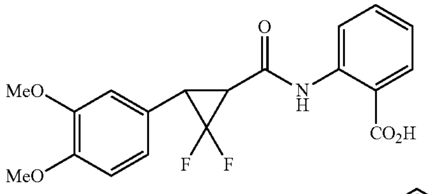

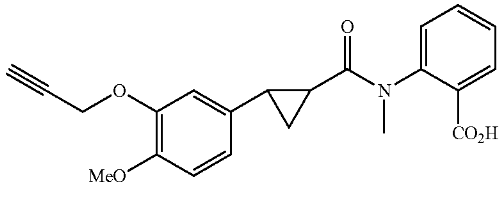

-continued
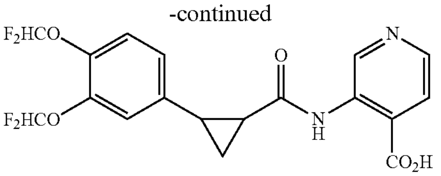
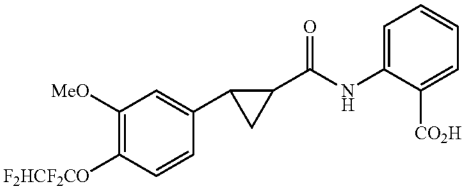
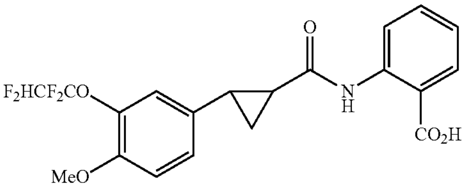
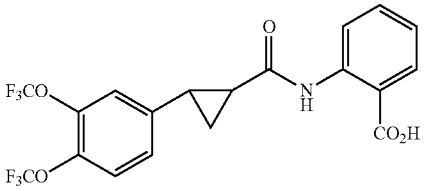
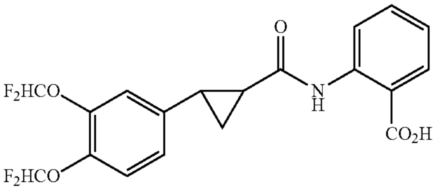
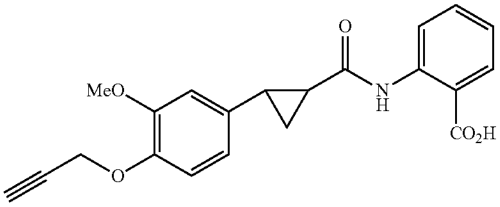
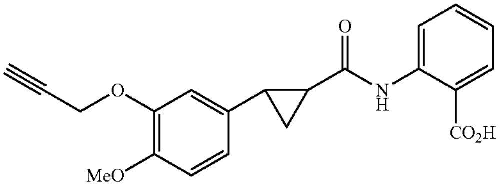
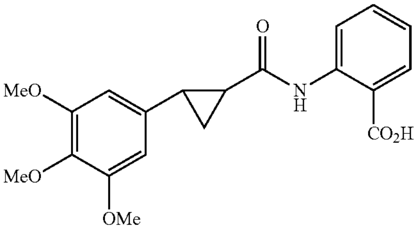
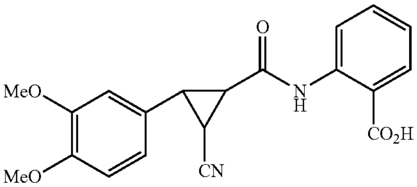
-continued
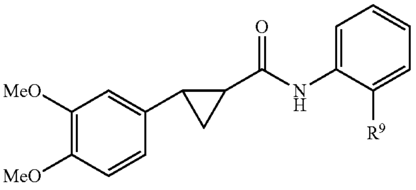
$R^9$ = $SO_2Me$, $SO_2NH_2$
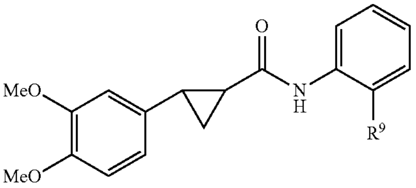
$R^9$ = $NH_2$, $CONH_2$, CONHMe, CONHOH
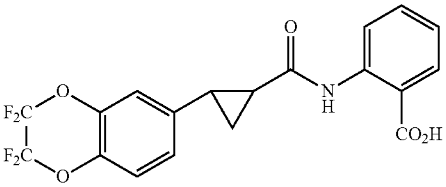
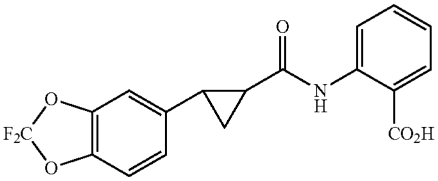
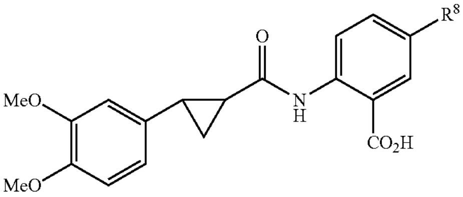
$R^8$ = Hydrogen, Halogen
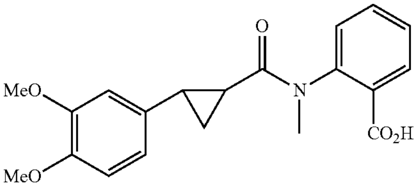
or a pharmaceutically acceptable salt thereof.
Non-limiting examples of suitable tranilast compounds of formulae 11 and 13 as described above include:
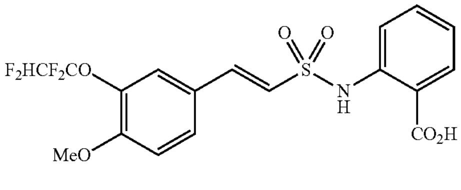

-continued
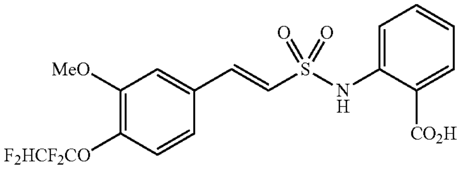
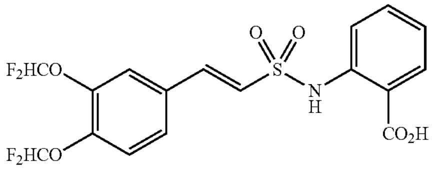
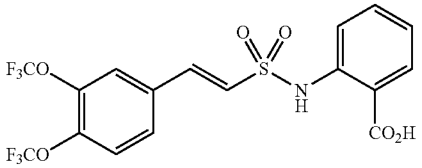
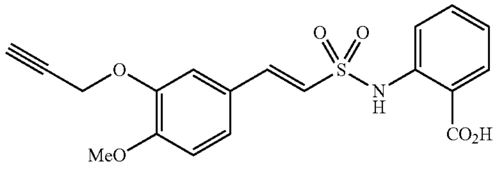
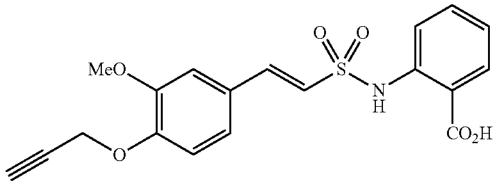
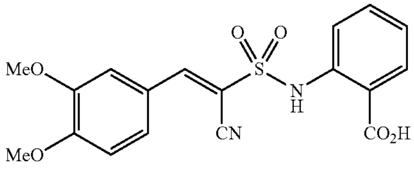
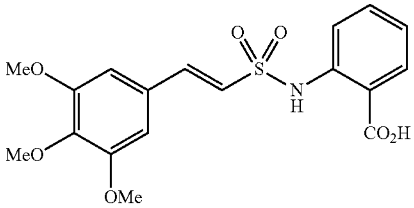
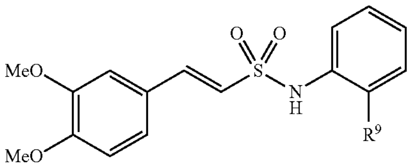
$R^9$= $SO_2Me$, $SO_2NH_2$, 5-tetrazolyl
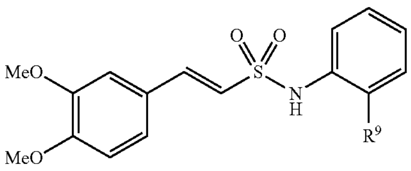
$R^9$= $NH_2$, $CONH_2$, CONHMe, CONHOH
-continued
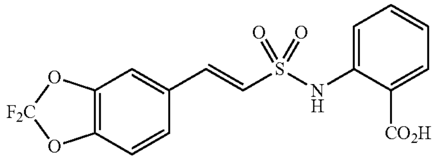
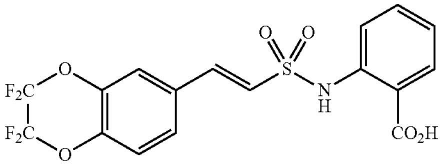
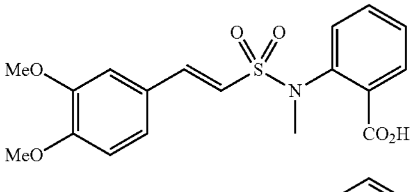
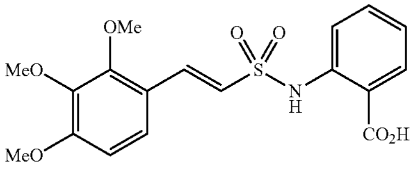
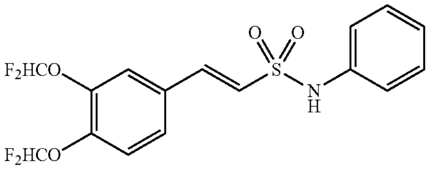
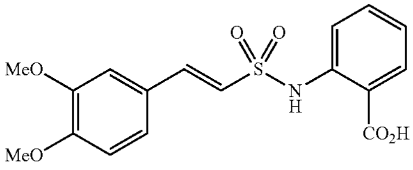
or a pharmaceutically acceptable salt thereof.
Non-limiting examples of suitable tranilast compounds of formulae 11 and 14 as described above include:
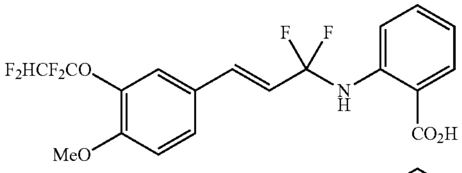
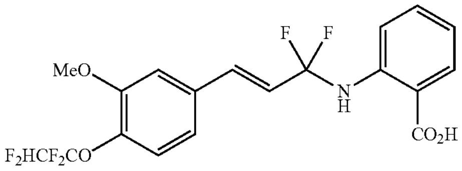
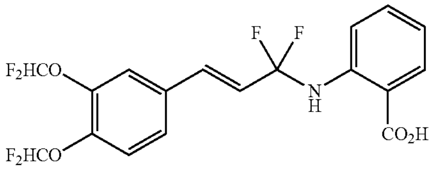

-continued
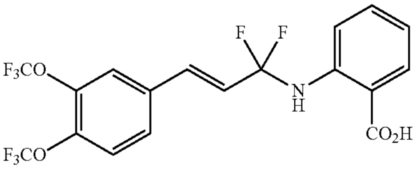
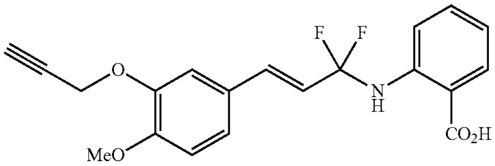
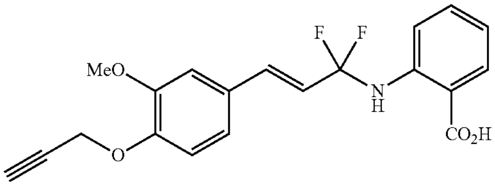
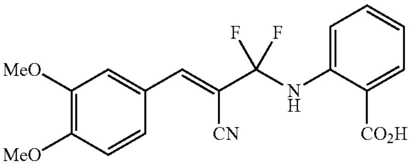
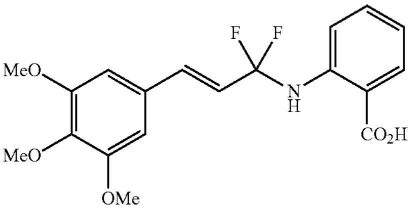
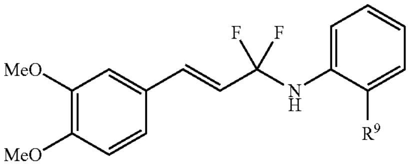
$R^9 = SO_2Me, SO_2NH_2$, 5-tetrazolyl
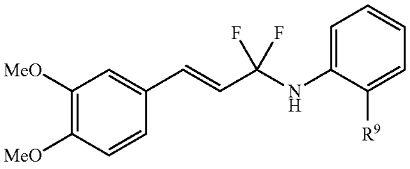
$R^9 = NH_2, CONH_2$, CONHMe, CONHOH
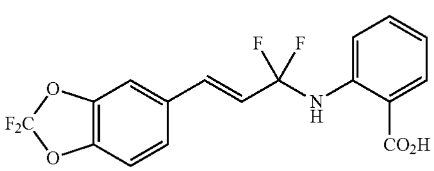
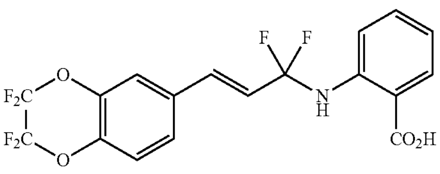
-continued
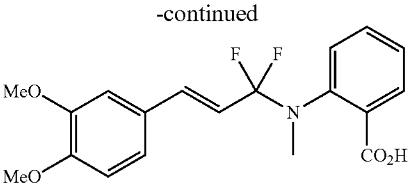
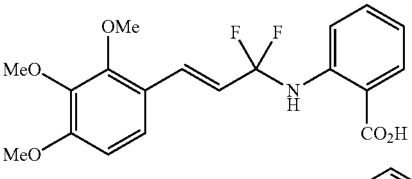
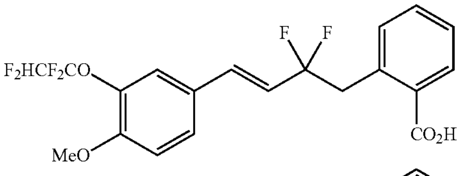
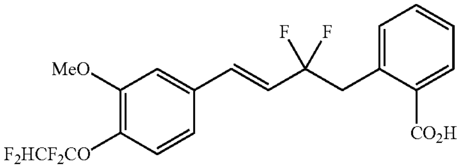
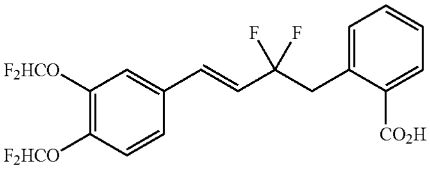
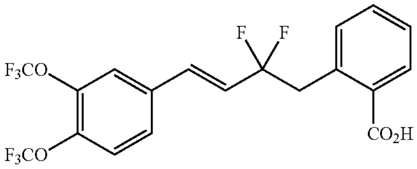
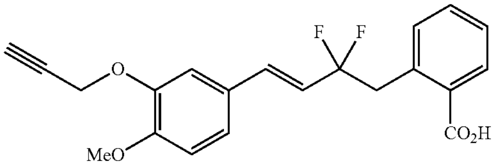
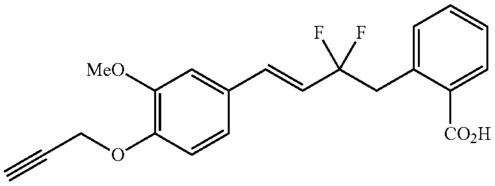
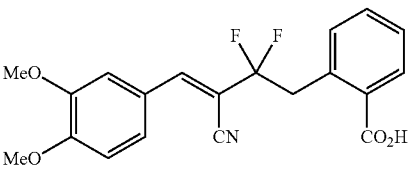
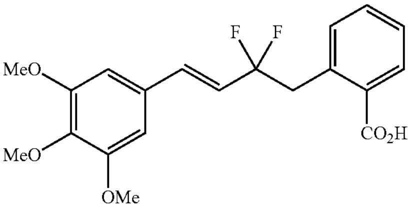

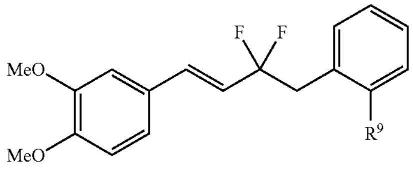
$R^9 = SO_2Me, SO_2NH_2$, 5-tetrazolyl
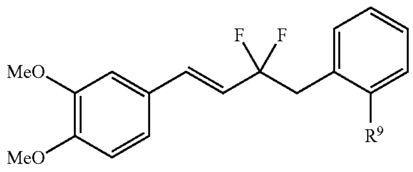
$R^9 = NH_2, CONH_2$, CONHMe, CONHOH
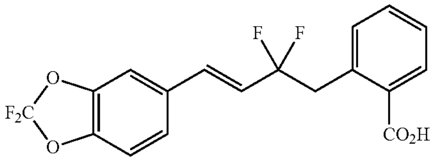
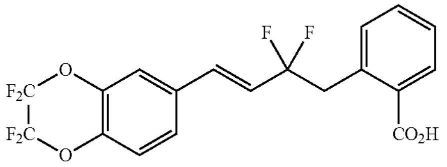
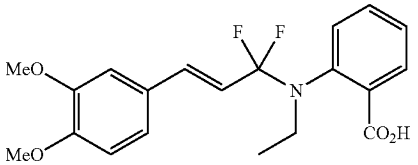
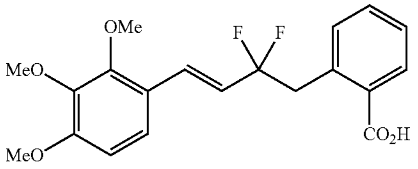
or a pharmaceutically acceptable salt thereof.
More non-limiting examples of suitable tranilast compounds of formulae 11 include:
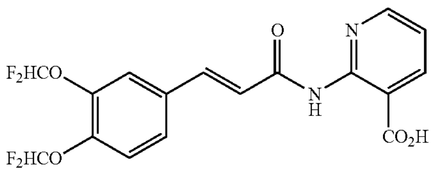
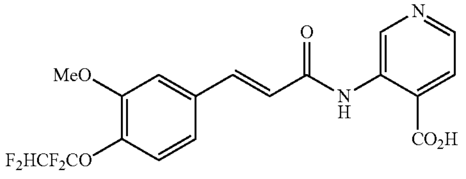
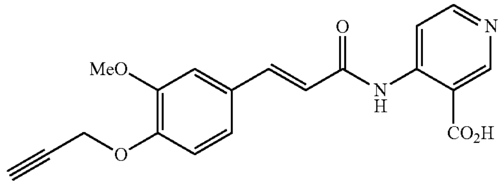
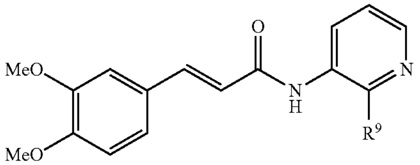
$R^9 = NH_2, CONH_2$, CONHMe, CONHOH
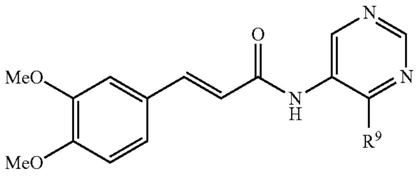
$R^9 = SO_2Me, SO_2NH_2$, SONHMe, $SONMe_2$
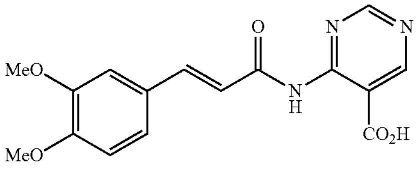
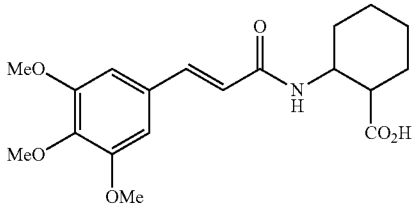
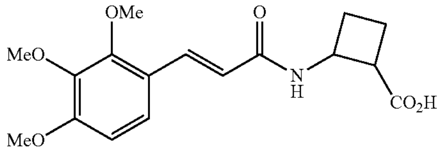
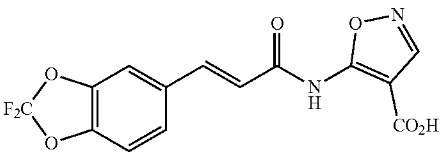
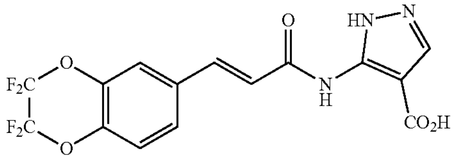
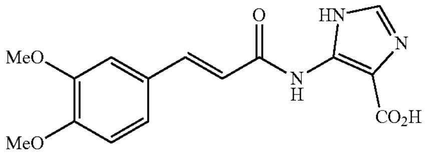

-continued
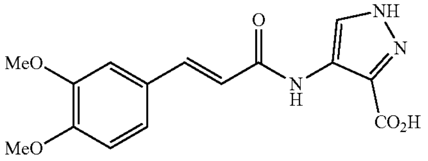
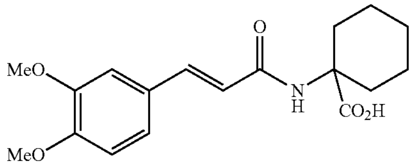
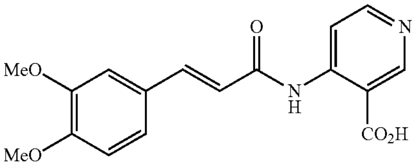
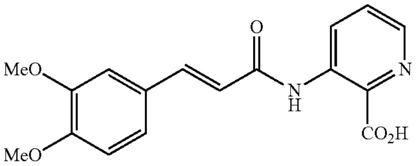
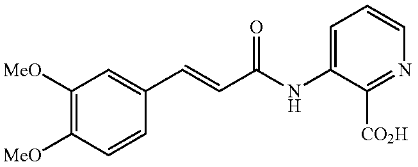
or a pharmaceutically acceptable salt thereof.
Non-limiting examples of suitable tranilast compounds of formulae 11 and 16 as described above include:
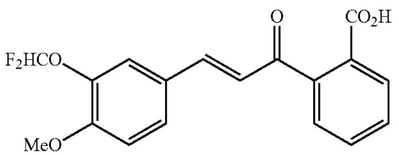
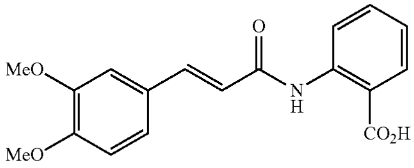
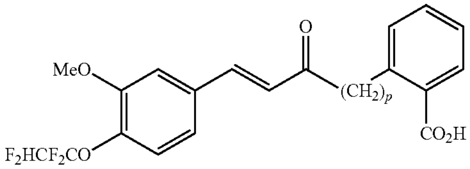
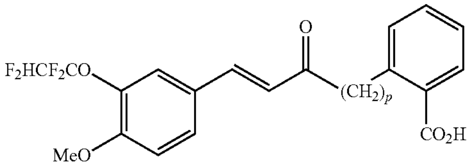
-continued
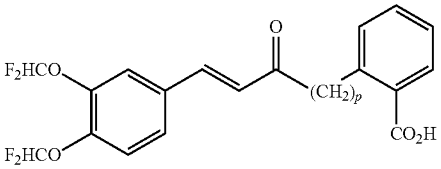
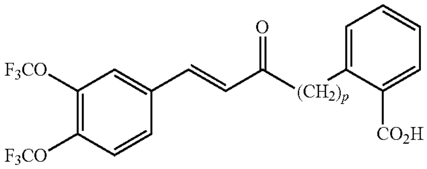
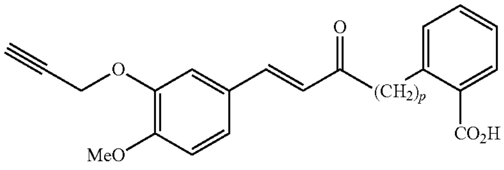
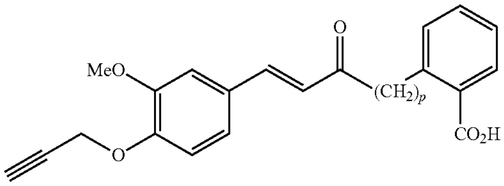
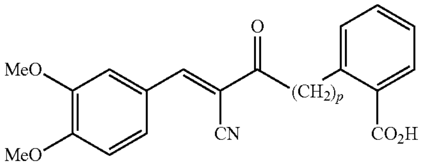
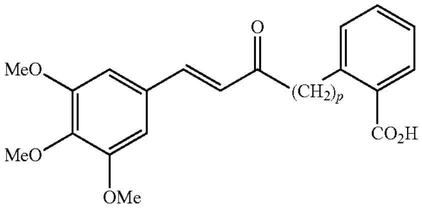
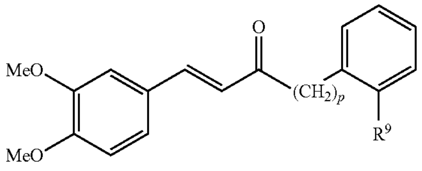
$R^9$= $SO_2Me$, $SO_2NH_2$, 5-tetrazolyl
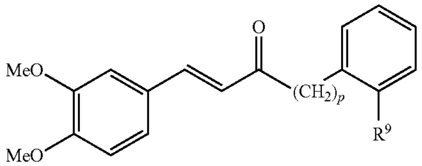
$R^9$= $NH_2$, $CONH_2$, CONHMe, CONHOH
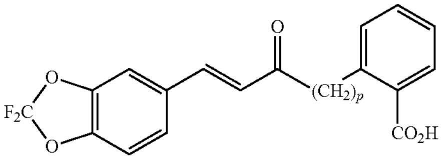

-continued

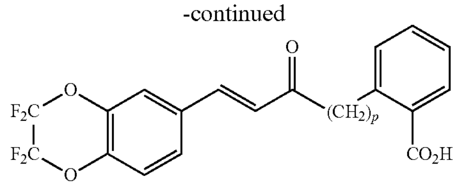

wherein p is 0 or 1;

or a pharmaceutically acceptable salt thereof.

In some embodiments of the first aspect of the invention, the tranilast compound has the formula 17

Formula 17

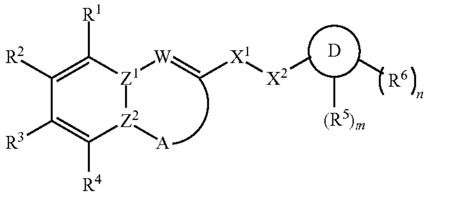

wherein:

W is selected from the group consisting of: $CR^7$ and N;

A is selected from the group consisting of: $—(CR^8R^9)_p—(Y)_q—(C(O))_r—(CR^{10}R^{11})_s—$ and $—(CR^8R^9)_p—(C(O))_r—(Y)_q—(CR^{10}R^{11})_s—$, wherein Y is selected from the group consisting of: O, S, $NR^{12}$, each p and s are an integer independently selected from the group consisting of 0, 1, and 2, each q and r are an integer independently selected from the group consisting of 0 and 1, and p+q+r+s is an integer selected from the group consisting of 1, 2, and 3;

$Z^1$-$Z^2$ is selected from the group consisting of N—C= and C=C;

$X^1$ selected from the group consisting of: C=O, $CF_2$ or $SO_2$, $PO_2$;

$X^2$ is selected from the group consisting of: $NR^{13}$ and $(CH_2)_t$ wherein t is an integer selected from the group consisting of: 0 and 1;

D is selected from the group consisting of: a cycloalkyl, heterocycloalkyl, cycloalkenyl, heterocycloalkenyl, aryl or heteroaryl ring;

$R^1$, $R^4$, $R^5$, $R^6$, $R^7$, $R^8$, $R^9$, $R^{10}$, and $R^{11}$ are each independently selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{14}$, $SO_3H$, $SO_2NR^{15}R^{16}$, $SO_2R^{14}$, $SONR^{15}R^{16}$, $SOR^{14}$, $COR^{14}$, COOH, $COOR^{14}$, $CONR^{15}R^{16}$, $NR^{15}COR^{14}$, $NR^{15}COOR^{14}$, $NR^{15}SO_2R^{14}$, $NR^{15}CONR^{15}R^{16}$, $NR^{15}R^{16}$, and acyl;

$R^2$ and $R^3$, are each independently selected from the group consisting of: H, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{14}$, $SO_3H$, $SO_2NR^{15}R^{16}$, $SO_2R^{14}$, $SONR^{15}R^{16}$, $SOR^{14}$, $COR^{14}$, COOH, $COOR^{14}$, $CONR^{15}R^{16}$, $NR^{15}COR^{14}$, $NR^{15}COOR^{14}$, $NR^{15}SO_2R^{14}$, $NR^{15}CONR^{16}R^{17}$, $NR^{15}R^{16}$, and acyl; or $R^2$ and $R^3$ may be fused to form a 5 or 6 membered cycloalkyl, heterocycloalkyl, aryl or heteroaryl ring each of which may be optionally substituted;

$R^{12}$, $R^{13}$, $R^{15}$, $R^{16}$, and $R^{17}$ are each independently selected from the group consisting of: H, an N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

$R^{14}$ is selected from the group consisting of H, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

m is an integer selected from the group consisting of 0, 1, 2, 3, and 4;

n is an integer selected from the group consisting of 1, 2, 3, 4, and 5;

m+n is an integer selected from the group consisting of 1, 2, 3, 4, and 5;

or derivatives thereof, analogues thereof, pharmaceutically acceptable salts thereof, and metabolites thereof.

Non-limiting examples of suitable tranilast compounds of formula 17 as described above include:

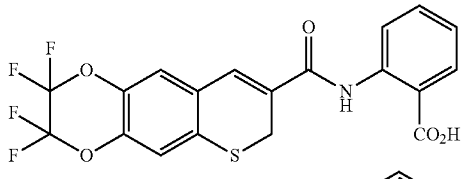

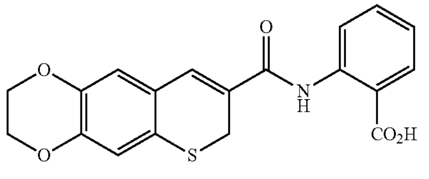

-continued
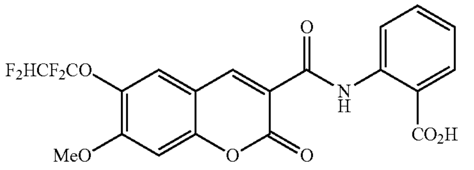
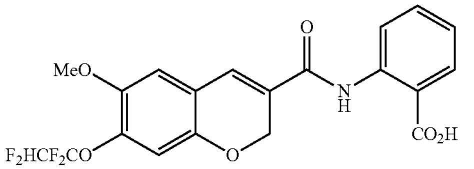
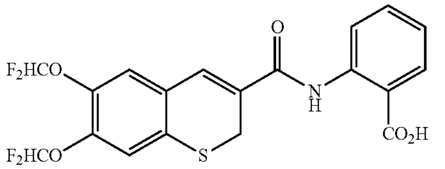
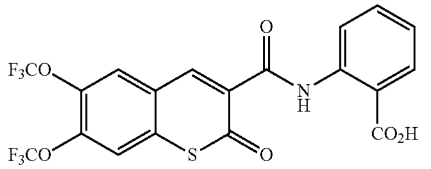
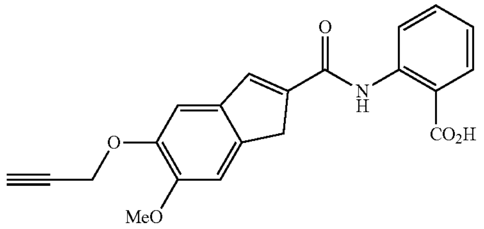
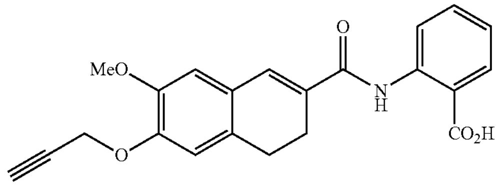
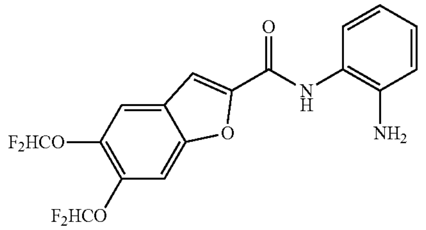
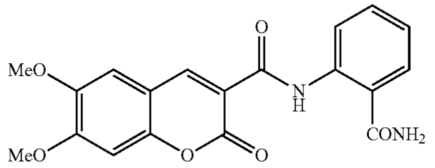
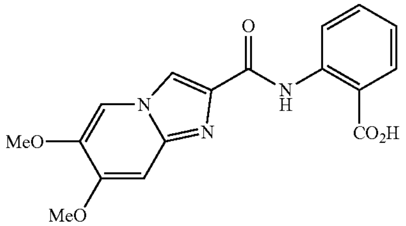
-continued
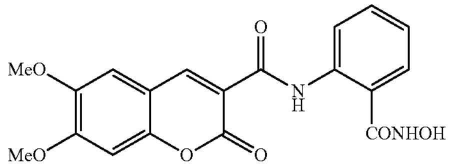
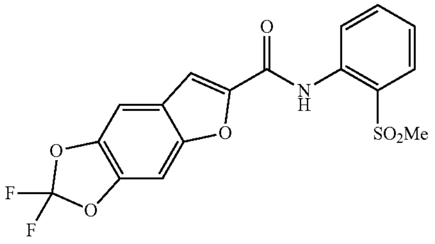
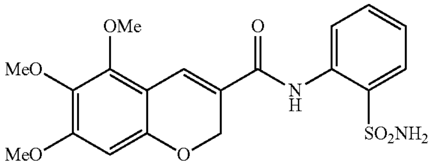
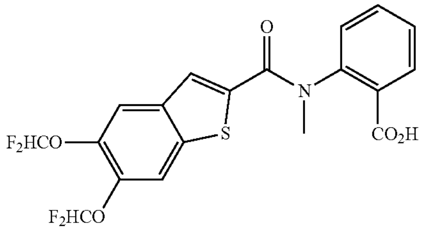
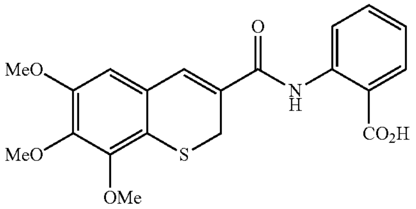
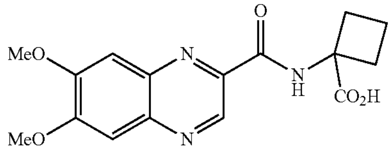
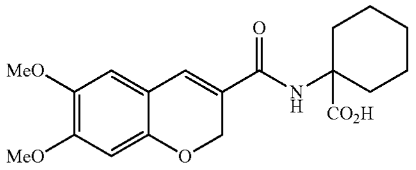
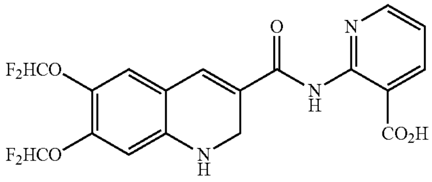
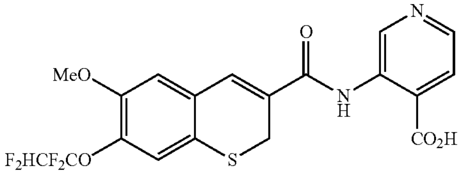

-continued
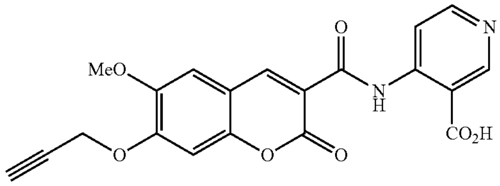
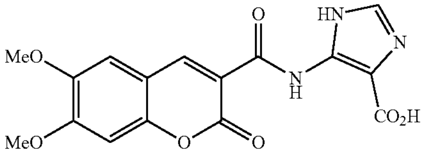
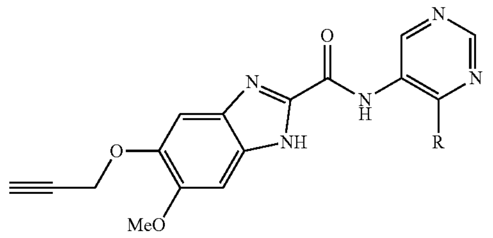
R = $SO_2Me$, $SO_2NH_2$, SONHMe, $SONMe_2$
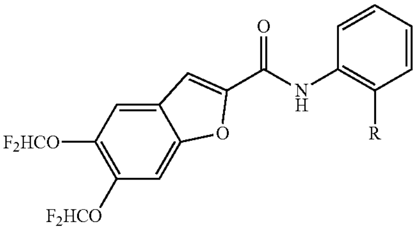
R = $NH_2$, $CONH_2$, CONHMe, CONHOH
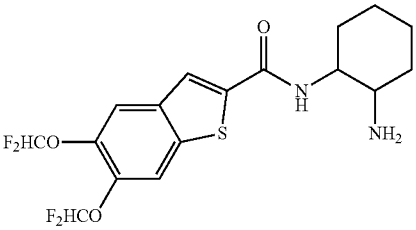
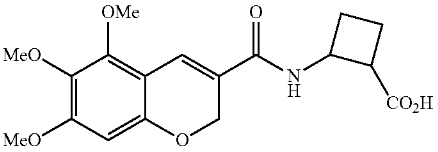
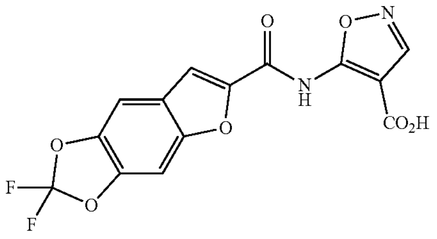
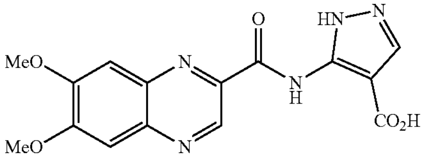
-continued
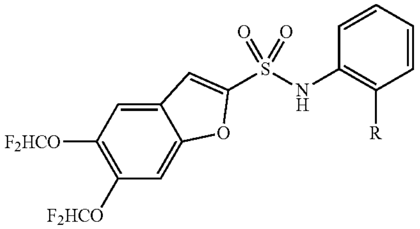
R = $SO_2Me$, $SO_2NH_2$, SONHMe, $SONMe_2$
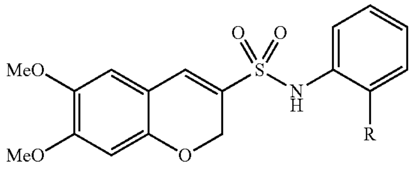
R = $NH_2$, $CONH_2$, CONHMe, CONHOH
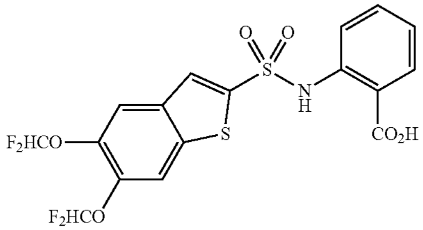
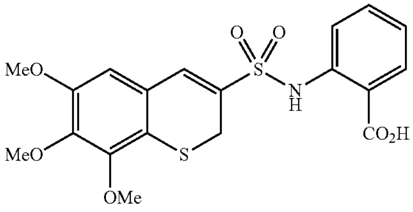
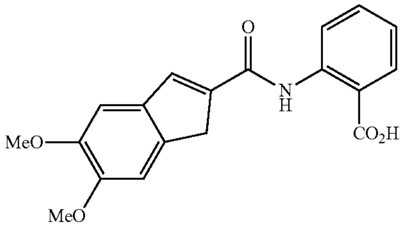
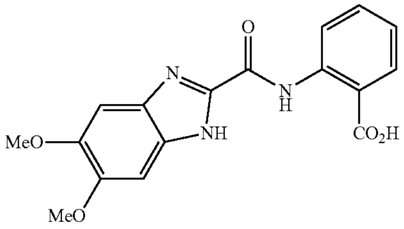
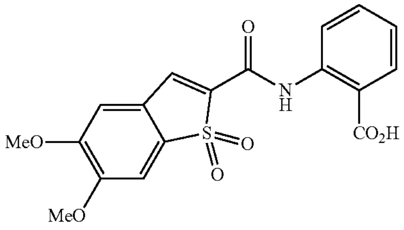

-continued

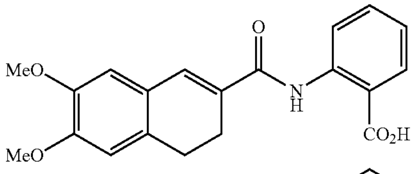

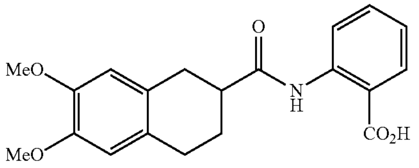

or a pharmaceutically acceptable salt or prodrug thereof.

In another embodiment of the first aspect of the invention, the tranilast compound has the formula 18

Formula 18

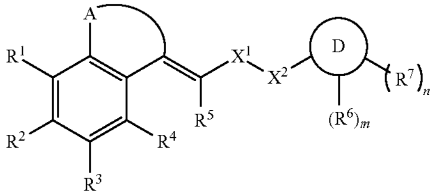

A is selected from the group consisting of: —$(CR^8R^9)_p$—$(Y)_q$—$(C(O))_r$—$(CR^{10}R^{11})_s$— and —$(CR^8R^9)_p$—$(C(O))_r$—$(Y)_q$—$(CR^{10}R^{11})_s$—, wherein Y is selected from the group consisting of: O, S, and $NR^{12}$, each p and s are an integer independently selected from the group consisting of: 0, 1, and 2, each q and r are an integer independently selected from the group consisting of: 0 and 1, and p+q+r+s is an integer selected from the group consisting of: 1, 2, and 3;

$X^1$ is selected from the group consisting of: C═O, $CF_2$, and $SO_2$, $PO_2$;

$X^2$ is selected from the group consisting of: $NR^{13}$ or $(CH_2)_t$ wherein t is an integer selected from the group consisting of: 0 and 1;

D is selected from the group consisting of: a cycloalkyl, heterocycloalkyl, cycloalkenyl, heterocycloalkenyl, aryl or heteroaryl ring;

$R^1$, $R^2$ and $R^3$, are each independently selected from the group consisting of: H, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{14}$, $SO_3H$, $SO_2NR^{15}R^{16}$, $SO_2R^{14}$, $SONR^{15}R^{16}$, $SOR^{14}$, $COR^{14}$, COOH, $COOR^{14}$, $CONR^{15}R^{16}$, $NR^{15}COR^{14}$, $NR^{15}COOR^{14}$, $NR^{15}SO_2R^{14}$, $NR^{15}CONR^{16}R^{17}$, $NR^{15}R^{16}$, and acyl; or $R^2$ and $R^3$ may be fused to form a 5 or 6 membered cycloalkyl; heterocycloalkyl, aryl or heteroaryl ring each of which may be optionally substituted;

$R^4$, $R^5$, $R^6$, $R^7$, $R^8$, $R^9$, $R^{10}$ and $R^{11}$ are each independently selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{14}$, $SO_3H$, $SO_2NR^{15}R^{16}$, $SO_2R^{14}$, $SONR^{15}R^{16}$, $SOR^{14}$, $COR^{14}$, COOH, $COOR^{14}$, $CONR^{15}R^{16}$, $NR^{15}COR^{14}$, $NR^{15}COOR^{14}$, $NR^{15}SO_2R^{14}$, $NR^{15}CONR^{16}R^{17}$, $NR^{15}R^{16}$, and acyl;

$R^{12}$, $R^{13}$, $R^{15}$, $R^{16}$, and $R^{17}$ are each independently selected from the group consisting of: H, a N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

$R^{14}$ is selected from the group consisting of H, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

m is an integer selected from the group consisting of: 0, 1, 2, 3, and 4;

n is an integer selected from the group consisting of: 1, 2, 3, 4, and 5;

m+n is an integer selected from the group consisting of: 1, 2, 3, 4, and 5;

or derivatives thereof, analogues thereof, pharmaceutically acceptable salts thereof, and metabolites thereof.

Non-limiting examples of suitable tranilast compounds of formula 18 as described above include:

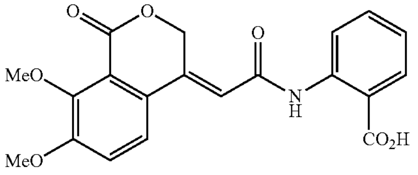

-continued
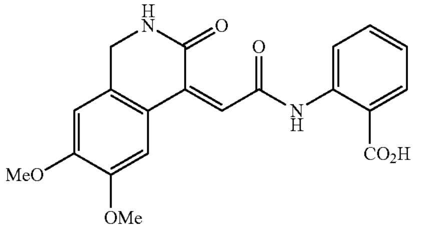
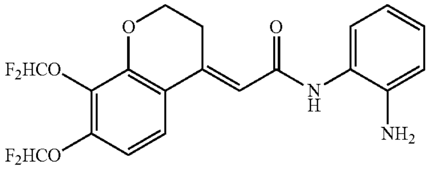
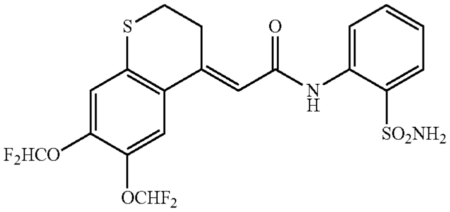
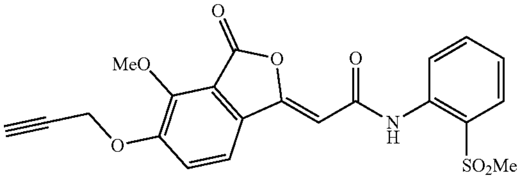
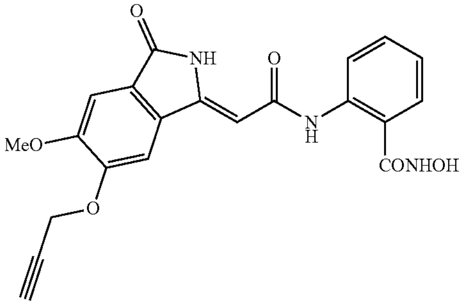
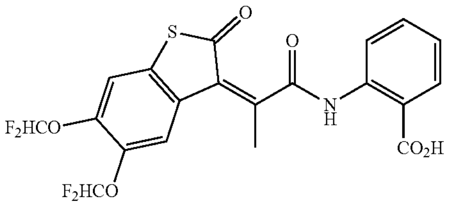
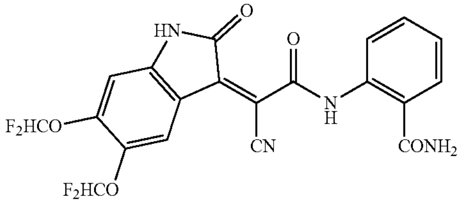
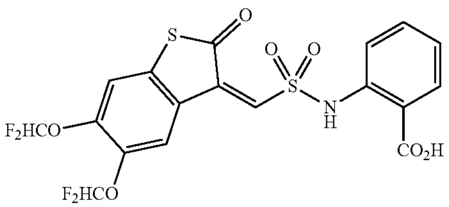
-continued
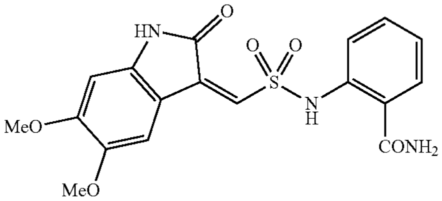
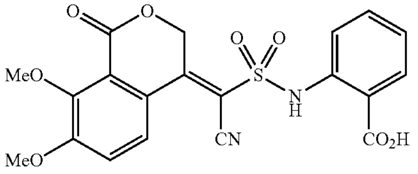
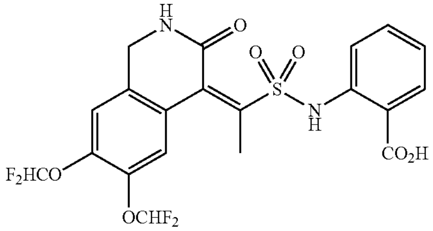
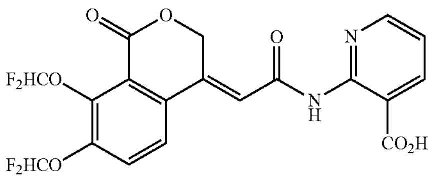
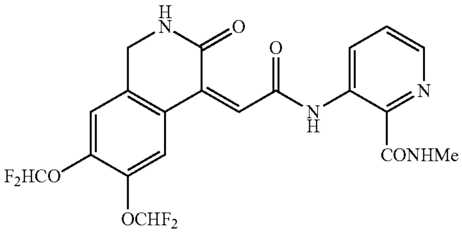
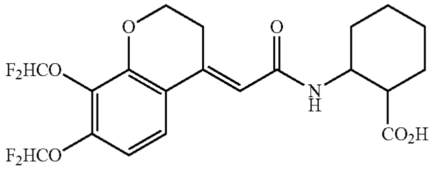
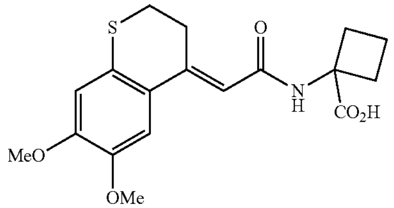
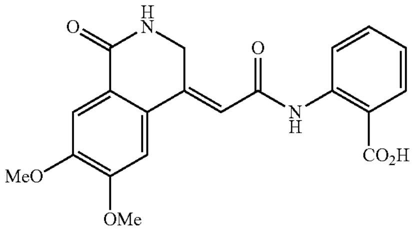 [SMILES: COc1cc2c(cc1OC)/C(=C/C(=O)Nc1ccccc1C(=O)O)CNC2=O]
or a pharmaceutically acceptable salt or prodrug thereof.

In yet another embodiment of the first aspect of the invention, the tranilast compound has the formula 19

Formula 19

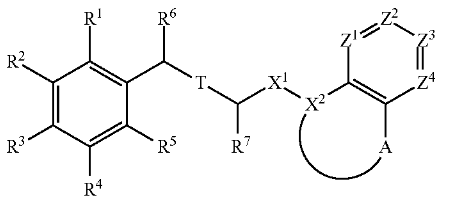

A is selected from the group consisting of: —($CR^9R^{10}$)$_p$—(Y)$_q$—(C(O))$_r$—($CR^{11}R^{12}$)$_s$— and —($CR^9R^{10}$)$_p$—(C(O))$_r$—(Y)$_q$—($CR^{11}R^{12}$)$_s$—, wherein Y is selected from the group consisting of: O, S, $NR^{13}$, each p and s are an integer independently selected from the group consisting of: 0, 1, and 2, each q and r are an integer independently selected from the group consisting of: 0 and 1, and p+q+r+s is an integer selected from the group consisting of: 1, 2, and 3;

T is selected from the group consisting of: a single bond, a double bond, a triple bond and

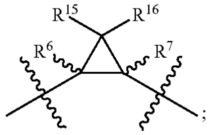

;

$X^1$ is selected from the group consisting of: C═O, $CF_2$ or $SO_2$, $PO_2$;

$X^2$ is selected from the group consisting of: $CR^{17}$ and N;

$Z^1$, $Z^2$, $Z^3$, and $Z^4$ are each independently selected from the group consisting of $CR^8$ and N;

$R^1$, $R^4$, $R^5$, $R^8$, $R^9$, $R^{10}$, $R^{11}$, $R^{12}$, $R^{15}$ and $R^{16}$ are each independently selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$.$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{18}$, $SO_3H$, $SO_2NR^{19}R^{20}$, $SO_2R^{18}$, $SONR^{19}R^{20}$, $SOR^{18}$, $COR^{18}$, COOH, $COOR^8$, $CONR^{19}R^{20}$, $NR^{19}COR^{18}$, $NR^{19}COOR^{18}$, $NR^{19}SO_2R^{18}$, $NR^{19}CONR^{20}R^{21}$, $NR^{19}R^{20}$, and acyl;

$R^2$ and $R^3$, are each independently selected from the group consisting of: H, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{18}$, $SO_3H$, $SO_2NR^{19}R^{20}$, $SO_2R^{18}$, $SONR^{19}R^{20}$, $SOR^{18}$, $COR^{18}$, COOH, $COOR^{18}$, $CONR^{19}R^{20}$, $NR^{19}COR^{18}$, $NR^{19}COOR^{18}$, $NR^{19}SO_2R^{18}$, $NR^{19}CONR^{20}R^{21}$, $NR^{19}R^{20}$, and acyl; or $R^2$ and $R^3$ may be fused to form a 5 or 6 membered cycloalkyl, heterocycloalkyl, aryl or heteroaryl ring, each of which may be optionally substituted;

$R^6$ and $R^7$ are present when T is a single bond, a double bond or

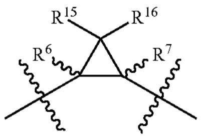

but not when T is a triple bond, each $R^6$ and $R^7$ being independently selected from the group consisting of: H, $NO_2$, CN, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{18}$, $SO_3H$, $SO_2NR^{19}R^{20}$, $SO_2R^{18}$, $SONR^{19}R^{20}$, $SOR^{18}$, $COR^{18}$, COOH, $COOR^{18}$, $CONR^{19}R^{20}$, $NR^{19}COR^{18}$, $NR^{19}COOR^{18}$, $NR^{19}SO_2R^{18}$, $NR^{19}CONR^{20}R^{21}$, $NR^{19}R^{20}$, and acyl;

$R^{13}$, $R^{19}$, $R^{20}$ and $R^{21}$ are each independently selected from the group consisting of: H: a N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

$R^{18}$ is selected from the group consisting of H, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

n is an integer selected from the group consisting of: 0, 1, 2, 3, and 4;

or derivatives thereof, analogues thereof, pharmaceutically acceptable salts thereof, and metabolites thereof.

Non-limiting examples of suitable tranilast compounds of formula 19 as described above include:

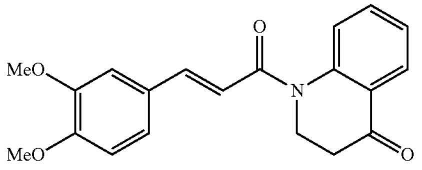

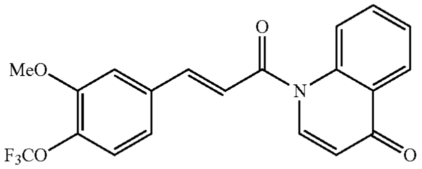

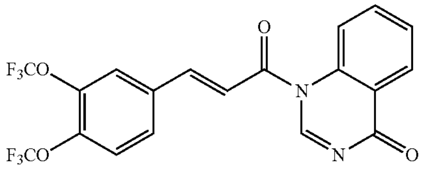

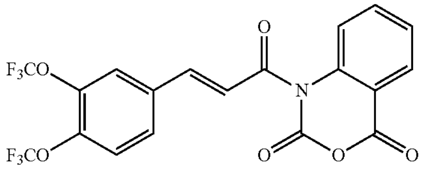

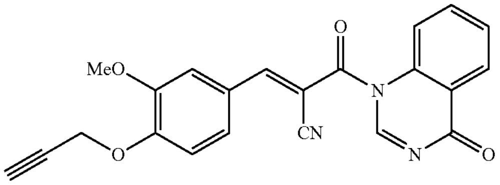

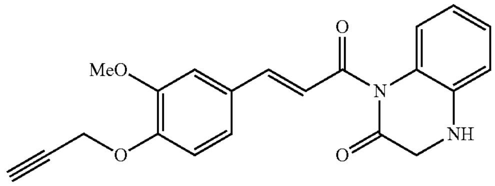

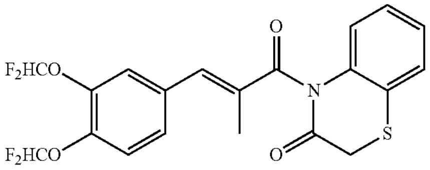

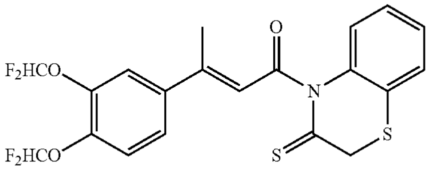

-continued

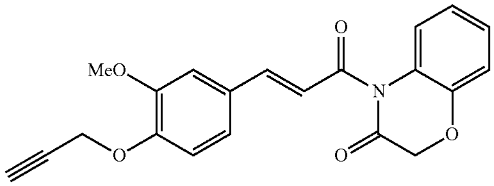

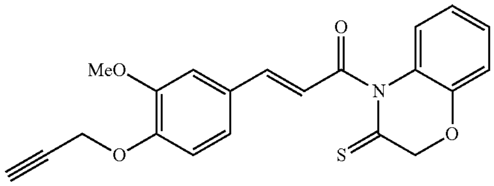

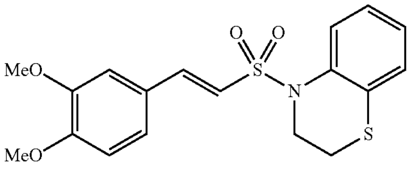

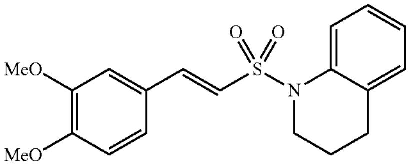

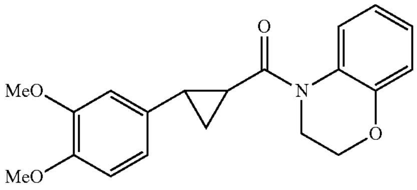

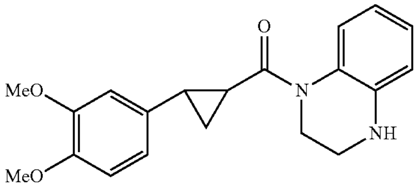

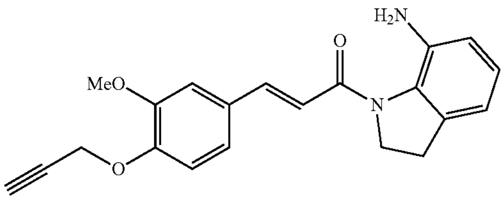

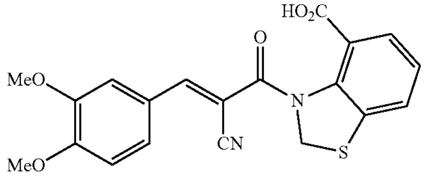

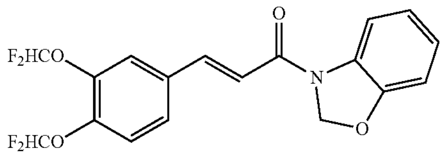

-continued
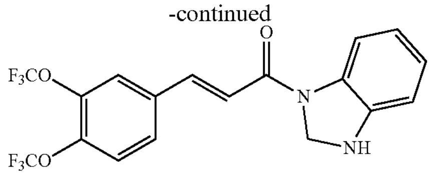
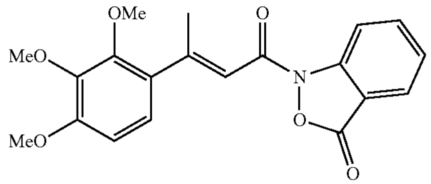
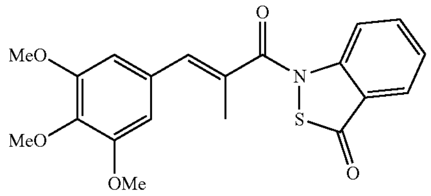
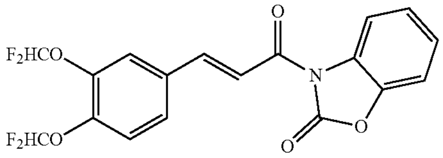
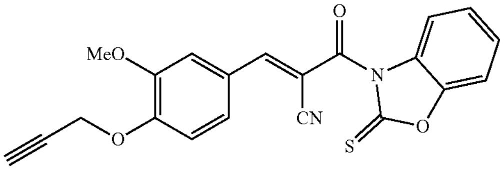
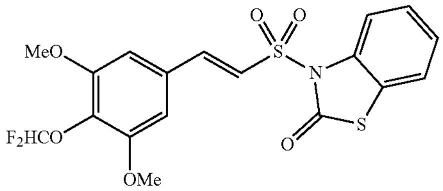
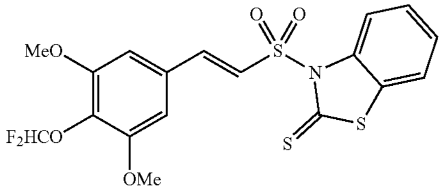
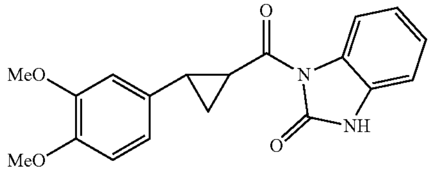
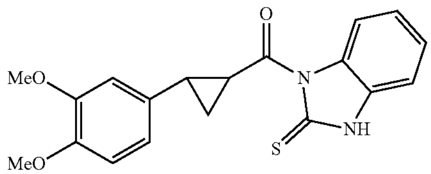
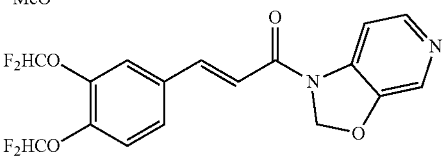
-continued
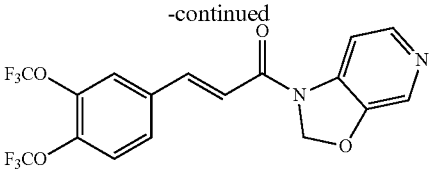
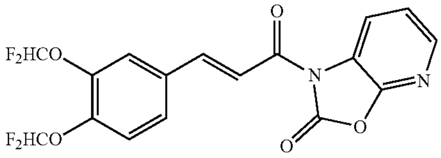
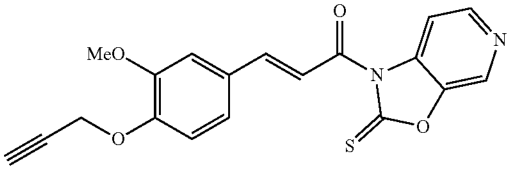
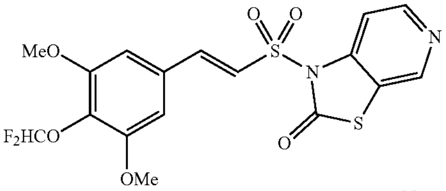
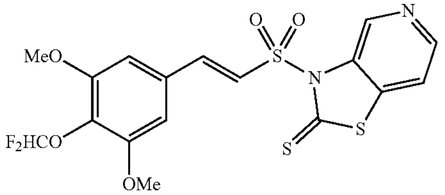
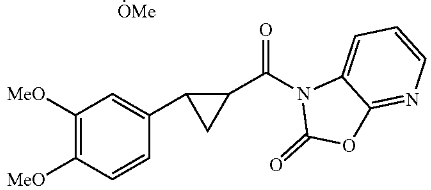
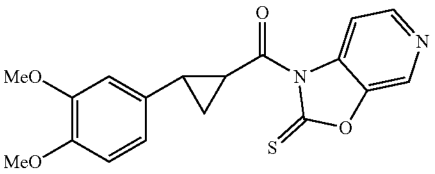
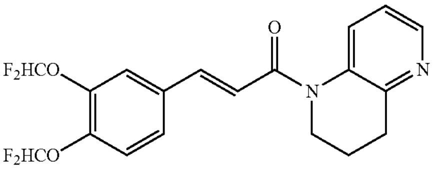
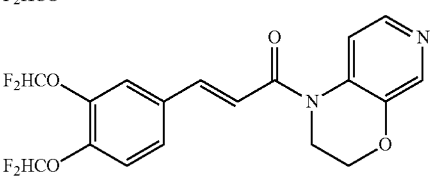
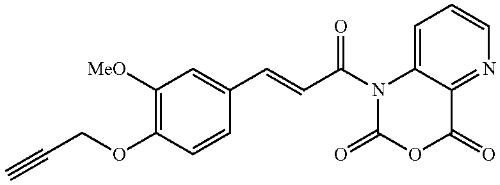

-continued

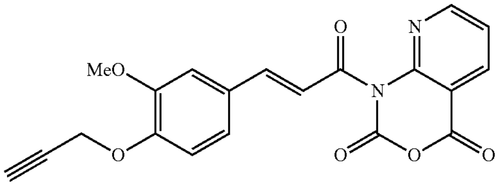

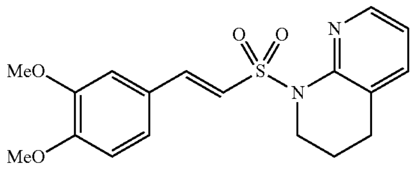

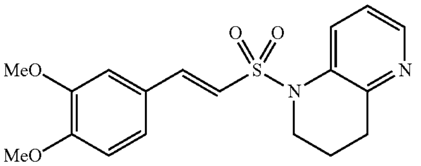

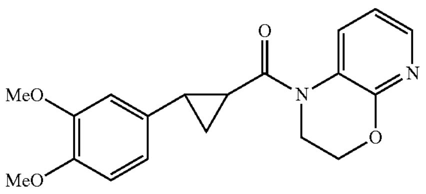

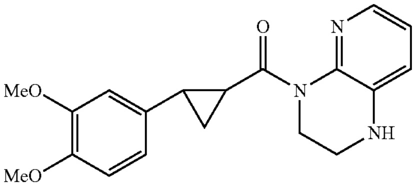

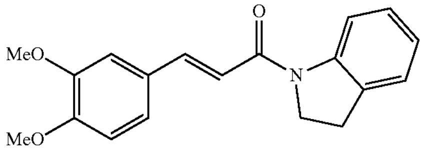

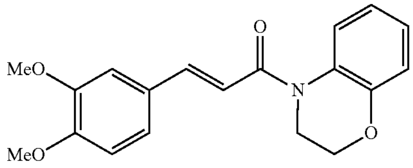

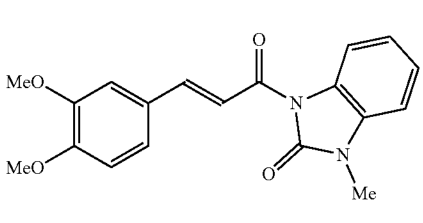

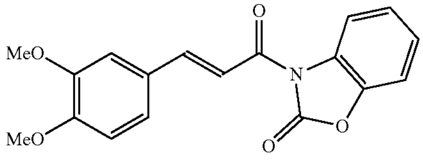

-continued

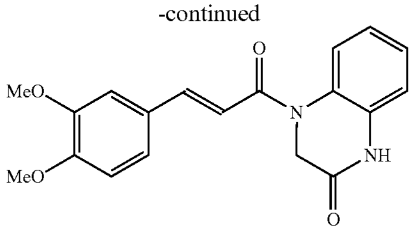

or a pharmaceutically acceptable salt or prodrug thereof.

In another embodiment of the first aspect of the invention, the tranilast compound has the formula 20

Formula 20

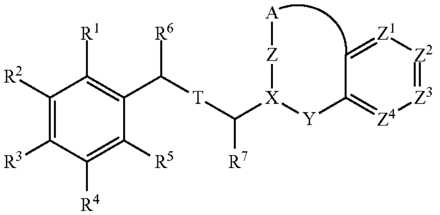

wherein:

Z—X—Y is selected from the group consisting of: N═C—N, N—C═N, O—C═N, S—C═N, N═C—O, N═C—S, C═C—NH, C═C—O, C═C—S, and C(O)—C═N;

A is selected from the group consisting of: a bond, $SO_2$, C, C═S, C═O, C═$NR^9$, and $NR^9$;

T is selected from the group consisting of: a single bond, a double bond, a triple bond, and

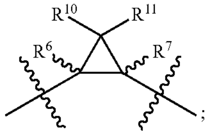

$Z^1$, $Z^2$, $Z^3$, and $Z^4$ are each independently selected from the group consisting of $CR^8$ and N;

$R^1$, $R^4$, $R^5$, $R^8$, $R^{10}$, and $R^{11}$ are each independently selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{12}$, $SO_3H$, $SO_2NR^{13}R^{14}$, $SO_2R^{12}$, $SONR^{13}R^{14}$, $SOR^{12}$, $COR^{12}$, COOH, $COOR^{12}$, $CONR^{13}R^{14}$, $NR^{13}COR^{12}$, $NR^{13}COOR^{12}$, $NR^{13}SO_2R^{12}$, $NR^{13}CONR^{14}R^{15}$, $NR^{14}R^{15}$, and acyl;

$R^2$ and $R^3$, are each independently selected from the group consisting of: H, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{12}$, $SO_3H$, $SO_2NR^{13}R^{14}$, $SO_2R^{12}$, $SONR^{13}R^{14}$, $SOR^{12}$, $COR^{12}$, COOH, $COOR^{12}$, $CONR^{13}R^{14}$, $NR^{13}COR^{12}$, $NR^{13}COOR^{12}$, $NR^{13}SO_2R^{12}$, $NR^{13}CONR^{14}R^{15}$, $NR^{14}R^{15}$, and acyl; or $R^2$ and $R^3$ may be fused to form a 5 or 6 membered cycloalkyl, heterocycloalkyl, aryl or heteroaryl ring each of which may be optionally substituted;

$R^6$ and $R^7$ are present when T is a single bond, a double bond or

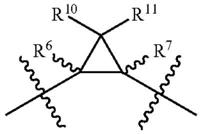

but not when T is a triple bond, each $R^6$ and $R^7$ being independently selected from the group consisting of: H, $NO_2$, CN, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{12}$, $SO_3H$, $SO_2NR^{13}R^{14}$, $SO_2R^{12}$, $SONR^{13}R^{14}$, $SOR^{12}$, $COR^{12}$, COOH, $COOR^{12}$, $CONR^{13}R^{14}$, $NR^{13}COR^{12}$, $NR^{13}COOR^{12}$, $NR^{13}SO_2R^{12}$, $NR^{13}CONR^{14}R^{15}$, $NR^{14}R^{15}$, and acyl;

$R^9$, $R^{13}$, $R^{14}$, and $R^{15}$ are each independently selected from the group consisting of: H, an N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

$R^{12}$ is selected from the group consisting of H, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

n is an integer selected from the group consisting of: 0, 1, 2, 3, and 4;

or derivatives thereof, analogues thereof, pharmaceutically acceptable salts thereof, and metabolites thereof.

Non-limiting examples of suitable tranilast compounds of formula 20 as described above include:

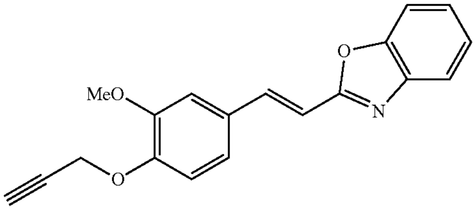

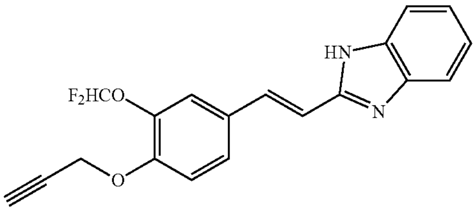

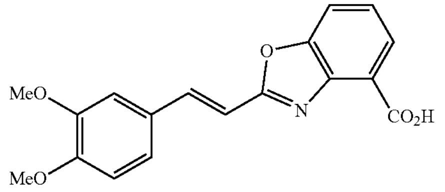

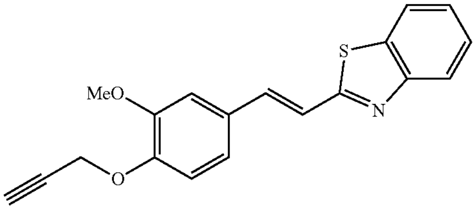

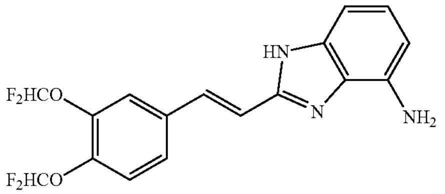

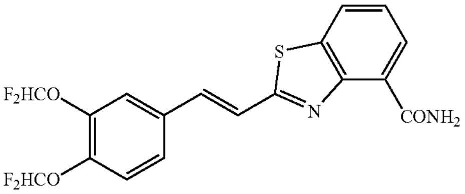

-continued
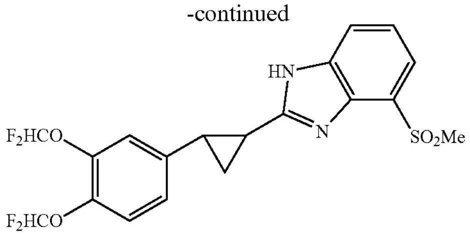
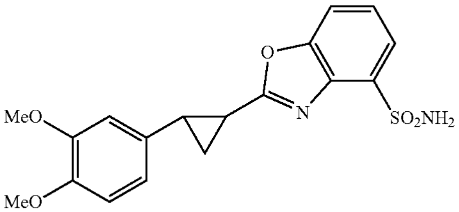
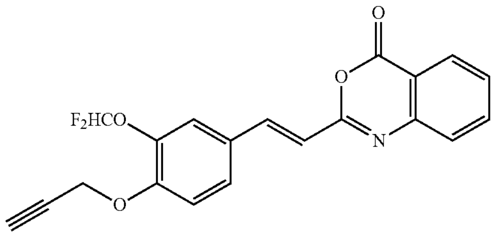
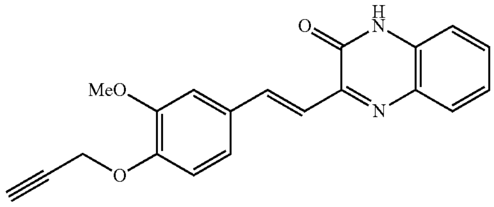
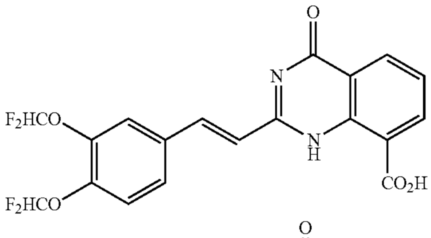
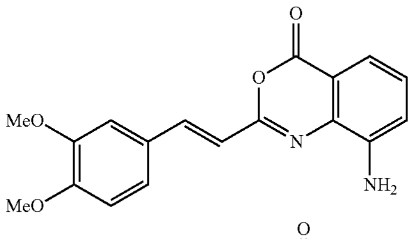
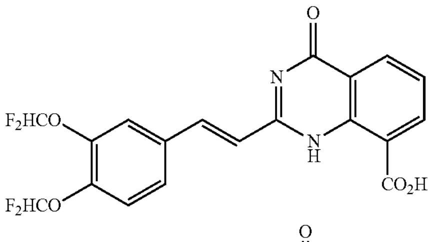
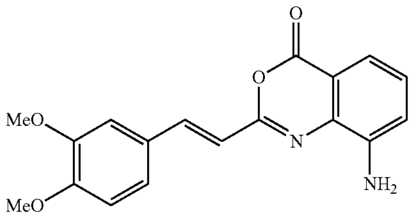
-continued
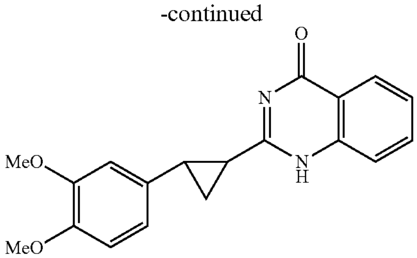
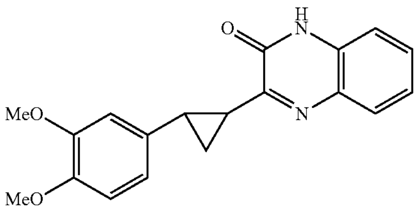
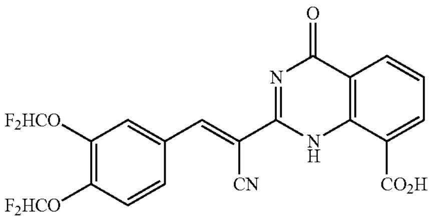
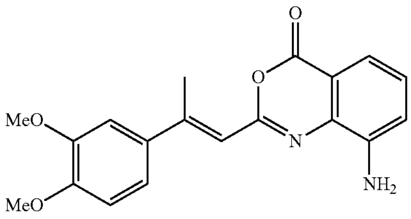
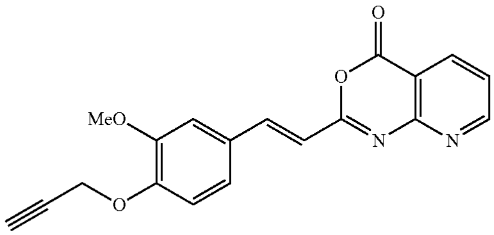
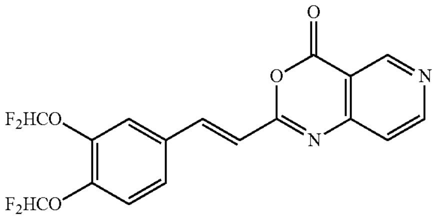
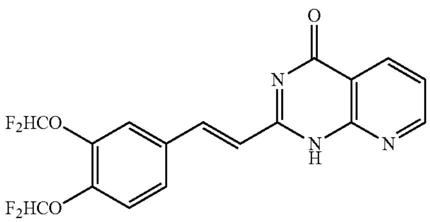

-continued

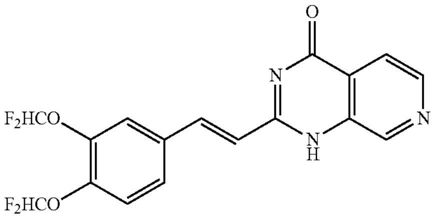

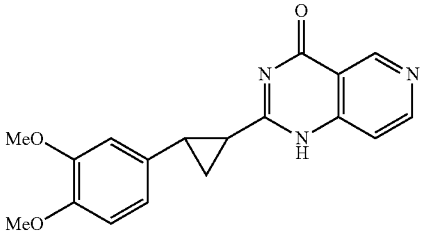

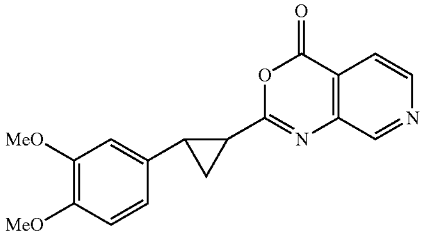

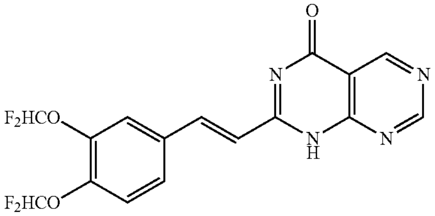

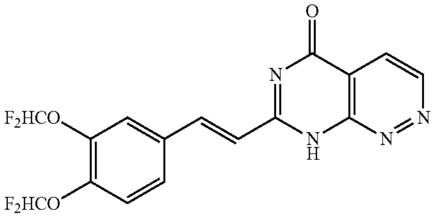

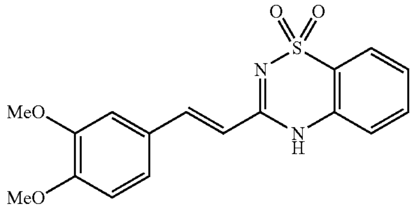

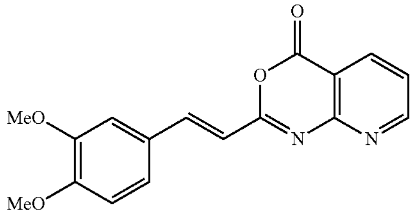

-continued

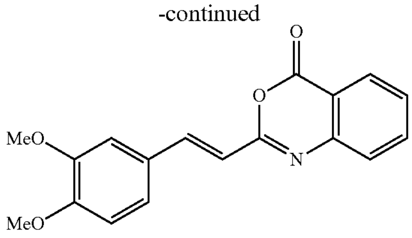

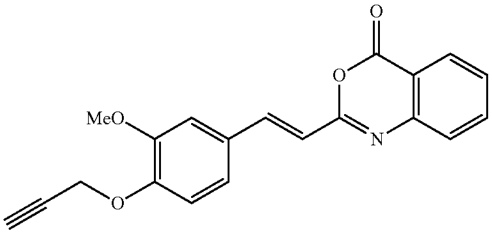

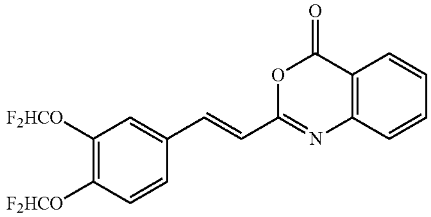

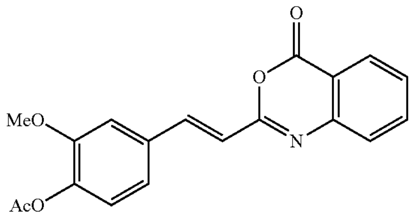

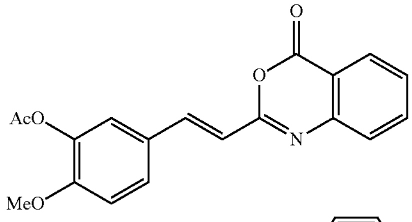

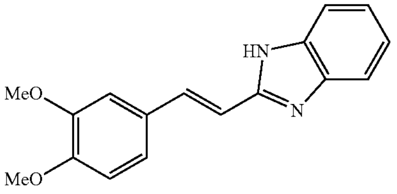

or a pharmaceutically acceptable salt or prodrug thereof.

One of ordinary skill in the art will appreciate that a variety of tranilast compounds may be used in the first aspect of the present invention.

The eye disease associated with inflammation and/or vascular proliferation in a subject is not intended to be particularly limited. In some embodiments of the first aspect of the invention, the eye disease may be selected from the group comprising diabetic retinopathy, corneal edema, anterior and posterior uveitis, pterygium, corneal diseases, dry eye, conjunctivitis, allergy- and laser-induced exudation, non-age related macular degeneration, macular edema, age-related macular degeneration and ocular von Hippel-Lindau disease.

In a further embodiment of the first aspect of the invention, the corneal disease is caused by infection from a microbe or microorganism. The microbe or microorganism may be selected from any of the groups comprising bacteria, viruses, fungi, amoebas, and parasites.

Preferably, the eye disease is diabetic retinopathy in the first aspect of the invention.

As used herein, treating the eye disease includes inhibiting the progression of the eye disease and/or ameliorating a symptom of the eye disease.

In a second aspect, the present invention provides a use of at least one tranilast compound or a pharmaceutically acceptable salt or solvate thereof in the preparation of a pharmaceutical composition for treating an eye disease associated with inflammation and/or vascular proliferation.

In preferred embodiments of the second aspect of the invention, the tranilast compound is a compound of any one of formulae 1, 2, 3, 4, 5, 6, 7, 8, 9, 10, 11, 12, 13, 14, 15, 16, 17, 18, 19 and 20 as described above in relation to the first aspect of the invention.

In another preferred embodiment of the second aspect of the invention, the tranilast compound may be a compound of the non-limiting examples of suitable tranilast compounds of formulae 1, 2, 3, 4, 5, 6, 7, 8, 9, 10, 11, 12, 13, 14, 15, 16, 17, 18, 19 and 20 described above in relation to the first aspect of the invention.

In a particularly preferred embodiment of the second aspect of the invention, the tranilast compound has the formula

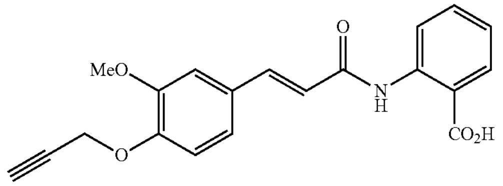 [SMILES: C#CCOc1ccc(/C=C/C(=O)Nc2ccccc2C(=O)O)cc1OC]

or a pharmaceutically acceptable salt thereof.

In another particularly preferred embodiment of the second aspect of the present invention, the tranilast compound has the formula

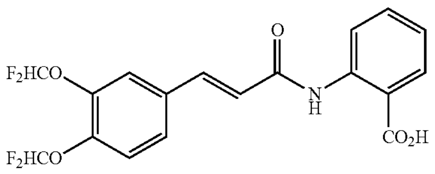 [SMILES: O=C(/C=C/c1ccc(OC(F)F)c(OC(F)F)c1)Nc1ccccc1C(=O)O]

or a pharmaceutically acceptable salt thereof.

In some embodiments of the second aspect of the invention, the eye disease may be selected from the group comprising diabetic retinopathy, corneal edema, anterior and posterior uveitis, pterygium, corneal diseases, dry eye, conjunctivitis, allergy- and laser-induced exudation, non-age related macular degeneration, macular edema, age-related macular degeneration and ocular von Hippel-Lindau disease.

In a further embodiment of the second aspect of the invention, the corneal disease is caused by infection from a microbe or microorganism. The microbe or microorganism may be selected from any of the groups comprising bacteria, viruses, fungi, amoebas, and parasites.

Preferably, the eye disease is diabetic retinopathy in the second aspect of the invention.

In a third aspect, the present invention provides a use of at least one tranilast compound, or a pharmaceutically acceptable salt or solvate thereof, in the treatment of an eye disease associated with inflammation and/or vascular proliferation disease.

In a fourth aspect, the present invention provides a kit for treating an eye disease associated with inflammation and/or vascular proliferation including: at least one tranilast compound or a pharmaceutically acceptable salt or solvate thereof; and instructions for administering the tranilast-type compound to a subject in order to treat the eye disease.

In a fifth aspect, the present invention provides a tranilast compound for treating an eye disease associated with inflammation and/or vascular proliferation.

In preferred embodiments of the third, fourth or fifth aspects of the invention, the tranilast compound is a compound of any one of formulae 1, 2, 3, 4, 5, 6, 7, 8, 9, 10, 11, 12, 13, 14, 15, 16, 17, 18, 19 and 20 as described above in relation to the first aspect of the invention.

In another preferred embodiment of the third, fourth or fifth aspects of the invention, the tranilast compound may be a compound of the non-limiting examples of suitable tranilast compounds of formulae 1, 2, 3, 4, 5, 6, 7, 8, 9, 10, 11, 12, 13, 14, 15, 16, 17, 18, 19 and 20 described above in relation to the first aspect of the invention.

In a particularly preferred embodiment of the third, fourth or fifth aspects of the invention, the tranilast compound has the formula

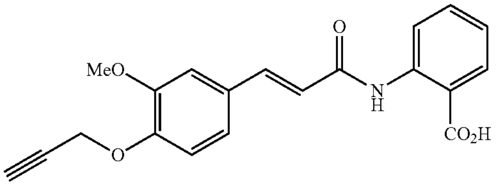 [SMILES: C#CCOc1ccc(/C=C/C(=O)Nc2ccccc2C(=O)O)cc1OC]

or a pharmaceutically acceptable salt thereof.

In another particularly preferred embodiment of the third, fourth or fifth aspects of the invention, the tranilast compound has the formula

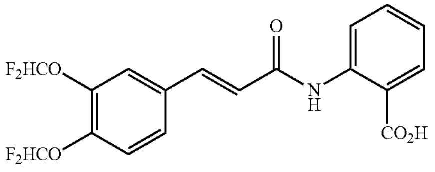 [SMILES: O=C(/C=C/c1ccc(OC(F)F)c(OC(F)F)c1)Nc1ccccc1C(=O)O]

or a pharmaceutically acceptable salt thereof.

In some embodiments of the third, fourth or fifth aspects of the invention, the eye disease may be selected from the group comprising diabetic retinopathy, corneal edema, anterior and posterior uveitis, pterygium, corneal diseases, dry eye, conjunctivitis, allergy- and laser-induced exudation, macular degeneration, macular edema, age-related macular degeneration and ocular von Hippel-Lindau disease.

In a further embodiment of the third, fourth or fifth aspects of the invention, the corneal disease is caused by infection from a microbe or microorganism. The microbe or microorganism may be selected from the group comprising bacteria, viruses, fungi, amoebas, and parasites.

Again, it is preferred the eye disease is diabetic retinopathy in the third, fourth or fifth aspects of the invention.

DETAILED DESCRIPTION OF THE INVENTION

In this specification a number of terms are used which are well known to a skilled addressee. Nevertheless for the purposes of clarity a number of terms will be defined.

As used herein, the term "unsubstituted" means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkoxy, alkoxyalkyl, alkoxycycloalkyl, alkoxyheterocycloalkyl, alkoxyaryl, alkoxyheteroaryl, alkoxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, arylalkyl, heteroarylalkyl, cycloalkylalkyl, heterocycloalkylalkyl, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —COOH, —$COR^{11}$, —C(O)$OR^{11}$, $CONHR^{11}$, $NHCOR^{11}$, $NHCOOR^{11}$, $NHCONHR^{11}$, C(=NOH)$R^{11}$, —SH, —$SR^{11}$, —$OR^{11}$ and acyl, wherein $R^{11}$ is H, optionally substituted $C_1$-$C_{12}$alkyl, optionally substituted $C_2$-$C_{12}$alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, optionally substituted $C_1$-$C_{18}$ heteroaryl, and acyl.

"Alkyl" as a group or part of a group refers to a straight or branched aliphatic hydrocarbon group, preferably a $C_1$-$C_{14}$ alkyl, more preferably $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Alkylamino" includes both mono-alkylamino and dialkylamino, unless specified. "Mono-alkylamino" means a —NH-Alkyl group, in which alkyl is as defined above. "Dialkylamino" means a —N$(alkyl)_2$ group, in which each alkyl may be the same or different and are each as defined herein for alkyl. The alkyl group is preferably a $C_1$-$C_6$ alkyl group. The group may be a terminal group or a bridging group.

"Arylamino" includes both mono-arylamino and di-arylamino unless specified. Mono-arylamino means a group of formula arylNH—, in which aryl is as defined herein. di-arylamino means a group of formula $(aryl)_2$N— where each aryl may be the same or different and are each as defined herein for aryl. The group may be a terminal group or a bridging group.

"Acyl" means an alkyl-CO— group in which the alkyl group is as described herein. Examples of acyl include acetyl and benzoyl. The alkyl group is preferably a $C_1$-$C_6$ alkyl group. The group may be a terminal group or a bridging group.

"Alkenyl" as a group or part of a group denotes an aliphatic hydrocarbon group containing at least one carbon-carbon double bond and which may be straight or branched preferably having 2-14 carbon atoms, more preferably 2-12 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkoxy" refers to an —O-alkyl group in which alkyl is defined herein. Preferably the alkoxy is a $C_1$-$C_6$ alkoxy. Examples include, but are not limited to, methoxy and ethoxy. The group may be a terminal group or a bridging group.

"Alkenyloxy" refers to an —O— alkenyl group in which alkenyl is as defined herein. Preferred alkenyloxy groups are $C_1$-$C_6$ alkenyloxy groups. The group may be a terminal group or a bridging group.

"Alkynyloxy" refers to an —O-alkynyl group in which alkynyl is as defined herein. Preferred alkynyloxy groups are $C_1$-$C_6$ alkynyloxy groups. The group may be a terminal group or a bridging group.

"Alkoxycarbonyl" refers to an —C(O)—O-alkyl group in which alkyl is as defined herein. The alkyl group is preferably a $C_1$-$C_6$ alkyl group. Examples include, but not limited to, methoxycarbonyl and ethoxycarbonyl. The group may be a terminal group or a bridging group.

"Alkylsulfinyl" means a —S(O)-alkyl group in which alkyl is as defined above. The alkyl group is preferably a $C_1$-$C_6$ alkyl group. Exemplary alkylsulfinyl groups include, but not limited to, methylsulfinyl and ethylsulfinyl. The group may be a terminal group or a bridging group.

"Alkylsulfonyl" refers to a —$S(O)_2$-alkyl group in which alkyl is as defined above. The alkyl group is preferably a $C_1$-$C_6$ alkyl group. Examples include, but not limited to methylsulfonyl and ethylsulfonyl. The group may be a terminal group or a bridging group.

"Alkynyl" as a group or part of a group means an aliphatic hydrocarbon group containing a carbon-carbon triple bond and which may be straight or branched preferably having from 2-14 carbon atoms, more preferably 2-12 carbon atoms, more preferably 2-6 carbon atoms in the normal chain. Exemplary structures include, but are not limited to, ethynyl and propynyl. The group may be a terminal group or a bridging group.

"Alkylaminocarbonyl" refers to an alkylamino-carbonyl group in which alkylamino is as defined above. The group may be a terminal group or a bridging group.

"Cycloalkyl" refers to a saturated or partially saturated, monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. The group may be a terminal group or a bridging group.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. The group may be a terminal group or a bridging group.

The above discussion of alkyl and cycloalkyl substituents also applies to the alkyl portions of other substituents, such as without limitation, alkoxy, alkyl amines, alkyl ketones, arylalkyl, heteroarylalkyl, alkylsulfonyl and alkyl ester substituents and the like.

"Cycloalkylalkyl" means a cycloalkyl-alkyl- group in which the cycloalkyl and alkyl moieties are as previously described. Exemplary monocycloalkylalkyl groups include cyclopropylmethyl, cyclopentylmethyl, cyclohexylmethyl and cycloheptylmethyl. The group may be a terminal group or a bridging group.

"Halogen" represents fluorine, chlorine, bromine or iodine.

"Heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazepane, 1,4-diazepane, 1,4-oxazepane, and 1,4-oxathiapane. The group may be a terminal group or a bridging group.

"Heterocycloalkenyl" refers to a heterocycloalkyl as described above but containing at least one double bond. The group may be a terminal group or a bridging group.

"Heterocycloalkylalkyl" refers to a heterocycloalkyl-alkyl group in which the heterocycloalkyl and alkyl moieties are as previously described. Exemplary heterocycloalkylalkyl groups include (2-tetrahydrofuryl)methyl, (2-tetrahydrothiofuranyl) methyl. The group may be a terminal group or a bridging group.

"Heteroalkyl" refers to a straight- or branched-chain alkyl group preferably having from 2 to 14 carbons, more preferably 2 to 10 carbons in the chain, one or more of which has been replaced by a heteroatom selected from S, O, P and N. Exemplary heteroalkyls include alkyl ethers, secondary and tertiary alkyl amines, amides, alkyl sulfides, and the like. The group may be a terminal group or a bridging group. As used herein reference to the normal chain when used in the context of a bridging group refers to the direct chain of atoms linking the two terminal positions of the bridging group.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$cycloalkyl or $C_{5-7}$ cycloalkenyl group are fused together to form a cyclic structure, such as tetrahydronaphthyl, indenyl or indanyl. The group may be a terminal group or a bridging group.

"Arylalkenyl" means an aryl-alkenyl- group in which the aryl and alkenyl are as previously described. Exemplary arylalkenyl groups include phenylallyl. The group may be a terminal group or a bridging group.

"Arylalkyl" means an aryl-alkyl- group in which the aryl and alkyl moieties are as previously described. Preferred arylalkyl groups contain a $C_{1-5}$ alkyl moiety. Exemplary arylalkyl groups include benzyl, phenethyl and naphthalenemethyl. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isoxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. The group may be a terminal group or a bridging group.

"Heteroarylalkyl" means a heteroaryl-alkyl group in which the heteroaryl and alkyl moieties are as previously described. Preferred heteroarylalkyl groups contain a lower alkyl moiety. Exemplary heteroarylalkyl groups include pyridylmethyl. The group may be a terminal group or a bridging group.

"Lower alkyl" as a group means unless otherwise specified, an aliphatic hydrocarbon group which may be straight or branched having 1 to 6 carbon atoms in the chain, more preferably 1 to 4 carbons such as methyl, ethyl, propyl (n-propyl or isopropyl) or butyl (n-butyl, isobutyl or tertiary-butyl). The group may be a terminal group or a bridging group.

The compounds may be prepared by any suitable method known to one of ordinary skill in the art. For instance, suitable methods of preparation of the compounds of formulae 1 to 20 above are disclosed in WO 2008/003141 (formulae 1 to 7), WO 2009/079692 (formulae 8 to 10), WO 2010/144959 (formulae 11 to 16), and WO 2011/047432 (formulae 17 to 20).

It is understood that included in the family of compounds of Formulae 1 to 20 are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art.

Some of the compounds as used in the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Some of the compounds as used in the disclosed embodiments are substituted cyclopropanes having the general formula

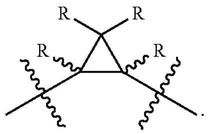

The structure shown is intended to include isomeric forms of the cyclopropanes including diastereoisomers and enantiomers.

Additionally, Formulae 1 to 20 are intended to cover, where applicable, solvated as well as unsolvated forms of the compounds. Thus, each formula includes compounds having the indicated structure, including the hydrated as well as the non-hydrated forms.

In addition to compounds of Formulae 1 to 20, the compounds of the various embodiments include pharmaceutically acceptable salts, prodrugs, N-oxides and active metabolites of such compounds, and pharmaceutically acceptable salts of such metabolites.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formulae 1 to 20 may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Suitable pharmaceutically acceptable base addition salts of compounds of Formulae 1 to 20 include metallic salts made from lithium, sodium, potassium, magnesium, calcium, aluminium, and zinc, and organic salts made from organic bases such as choline, diethanolamine, morpholine. Other examples of organic salts are: ammonium salts, quaternary salts such as tetramethylammonium salt; amino acid addition salts such as salts with glycine and arginine. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

"Prodrug" means a compound which is convertible in vivo by metabolic means (e.g. by hydrolysis, reduction or oxidation) to a compound of Formulae 1 to 20. For example an ester prodrug of a compound of Formulae 1 to 20 containing a hydroxyl group may be convertible by hydrolysis in vivo to the parent molecule. Suitable esters of compounds of Formulae 1 to 20 containing a hydroxyl group, are for example acetates, citrates, lactates, tartrates, malonates, oxalates, salicylates, propionates, succinates, fumarates, maleates, methylene-bis-p-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of Formulae 1 to 20 containing a carboxy group may be convertible by hydrolysis in vivo to the parent molecule. (Examples of ester prodrugs are those described by F. J. Leinweber, Drug Metab. Res., 18:379, 1987).

The terms "treating", "treat", or "treatment" refer generally to amelioration or elimination of a named condition once the condition has been established. The term "prophylaxis" refers generally to treatment to prevent the onset of a named condition or of a process that can lead to the condition ("primary" prophylaxis), or the recurrence of symptoms of a condition.

The term "subject" refers generally to any warm blooded animal such as, but not limited to, a mouse, guinea pig, dog, horse, or human. In an embodiment, the subject is human.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The term "pharmaceutically acceptable" refers generally to a substance or composition that is compatible chemically and/or toxicologically with the other ingredients including a formulation, and/or the subject being treated.

The compounds as utilised in the above five aspects of the present invention refers generally to compounds, prodrugs thereof, pharmaceutically acceptable salts of the compounds and/or prodrugs, and hydrates or solvates of the compounds, salts, and/or prodrugs, as well as all stereoisomers (including diastereoisomers and enantiomers), tautomers and isotopically labelled compounds. The compounds of the present invention may exist in unsolvated as well as solvated forms with pharmaceutically acceptable solvents such as water, ethanol, and the like, and it is intended that the invention embrace both solvated and unsolvated forms.

The term "derivative thereof" when used in reference to compounds of the present invention refers generally to prodrugs, pharmaceutically acceptable salts of the compounds and/or prodrugs, and hydrates or solvates of the compounds, salts, and/or prodrugs.

Administration of compounds of Formulae 1 to 20 or any composition(s) comprising same to subjects can be by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier, excipient and/or diluent and in an amount sufficient to deliver to the patient a therapeutically effective dose.

In using the compounds they can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. See *Remingtons Pharmaceutical Sciences,* $19^{th}$ edition, Mack Publishing Co. (1995) for further information.

The compounds can be administered alone or in the form of a pharmaceutical composition in combination with a pharmaceutically acceptable carrier, diluent, adjuvant and/or excipient. The compounds may be administered as the compounds themselves or in the form of their pharmaceutically acceptable salts or derivatives.

The compounds are, however, typically used in the form of pharmaceutical compositions which are formulated depending on the desired mode of administration. Suitable compositions for use in accordance with the methods of the present invention may be prepared according to methods and procedures that are known to those of ordinary skill in the art and accordingly may include a pharmaceutically acceptable carrier, excipient, diluent and/or adjuvant. As such in a further embodiment the present invention provides a pharmaceutical composition including a compound of Formulae 1 to 20 and a pharmaceutically acceptable carrier, diluent, adjuvant or excipient.

The invention in other embodiments provides a pharmaceutical pack or kit comprising one or more containers filled with one or more of the ingredients of the pharmaceutical compositions of the invention. In such a pack or kit can be found a container having a unit dosage of the agent(s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compounds may be used or administered in combination with one or more additional drug(s) for the treatment of the disorder/diseases mentioned. The components can be administered in the same formulation or in separate formulations or compositions. If administered in separate formulations or compositions, the compounds of the invention or the formulations or compositions comprising same may be administered sequentially or simultaneously with the other drug(s).

In addition to being able to be administered in combination with one or more additional drugs, the compounds may be used in a combination therapy. When this is done the compounds are typically administered in combination with each other. Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result. Administration may be systemic, regional or local.

Pharmaceutical compositions of the invention may be administered by standard routes. In general, the compositions may be administered by the parenteral (e.g., intravenous, intraspinal, subcutaneous or intramuscular), oral or topical route. The particular route of administration to be used in any given circumstance will depend on a number of factors, including the nature of the condition to be treated, the severity and extent of the condition, the required dosage of the particular compound to be delivered and the potential side-effects of the compound.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

Examples of pharmaceutically acceptable carriers or diluents are demineralised or distilled water; saline solution; vegetable based oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

These compositions may also contain one or more adjuvants such as preservatives, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol. The injectable solution or suspension can be sterilised, for example, by filtration through a bacterial-retaining filter, or by incorporating sterilising agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, dextrose, sucrose, glucose, sorbitol, mannitol, and silicic acid, b) binders as acceptable in human and veterinary pharmaceutical practice such as, for example, carboxymethylcellulose, alginates (e.g. sodium alginate), gelatin, polyvinylpyrrolidone, corn starch, sucrose, and acacia, c) humectants such as glycerol, d) disintegrating agents such as agar, agar-agar, calcium carbonate, potato or tapioca starch, alginic acid, certain silicates, sodium carbonate, corn starch, methylcellulose, polyvinylpyrrolidone, guar gum, xanthan gum and bentonite, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, stearic acid, sodium oleate, sodium chloride and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, sunflower, safflower, arachis, coconut and sesame oils), glycerol, tetrahydrofurfuryl alcohol, polyethylene glycols, triglycerides, fatty acid esters of sorbitan, lactose, sorbitol, mannitol, dextrose, kaolin, cellulose, calcium carbonate, calcium silicate and/or dicalcium phosphate and mixtures thereof.

Besides inert diluents, the oral compositions can also include adjuvants such as wetting agents, osmotic agents, comfort enhancing agents, emulsifying and suspending agents, sweeteners, thickening agents, preservatives, bactericides and/or bacteristatics, buffering agents, time delay agents, flavouring and perfuming agents. Suitable sweeteners include sucrose, lactose, glucose, aspartame or saccharine. Suitable flavouring agents include peppermint oil, oil of wintergreen, cherry, orange or raspberry flavouring. Suitable time delay agents include glyceryl monostearate or glyceryl distearate. Suitable wetting agents could be selected from the group comprising cellulose derivatives such as hydroxypropyl methyl cellulose, carboxymethyl cellulose, methyl cellulose, hydroxyethyl cellulose, dextran, gelatin, polyols, liquid such as glycerin, polyethylene glycol, polyethylene glycol, polysorbate, propylene glycol, polyvinyl alcohol, povidone (polyvinyl pyrrolidone) and copolymers such as EO/PO block copolymers. Suitable bactericides and/or bacteristatics include cationic antibacterial agents that bind with high affinity to negatively charged cell membranes of bacteria by displacing divalent cations in the membranes and causing the loss of essential cellular components (Gilbert and Moore 2005). Accordingly, cationic substances such as biguanides (i.e. salts of alexidine, alexidine free base, salt of chlorhexidine, hexamethylene biguanides, and polymeric biguanides such as polyhexamethylene biguanide [PHMB]), quaternary ammonium compounds (i.e. polyquaternium-1 [POLYQUAD], chemical registry number 75345-27-6; and cetylpyridinium chloride [CPC]), and myristamidopropyl dimethylamine [ALDOX]), povidone-iodine, hydrogen peroxide, benzyl alcohol, indolicidins, ethoxylated alkyl glucoside, and non-amine polyethyleneoxide are contemplated herein as non-limiting examples of cationic antibacterials. Similarly, dimethyldiallylammonium chloride homopolymer and strongly basic anionic exchange ammonium resins are also contemplated herein as non-limiting examples of antimicrobial agents.

For topical applications in the eye, ionic dissociating compounds as surfactants are contemplated such as lauroylethylenediaminetriacetate, polyethylene glycol fatty acid ester, an alkanolamide, an amide oxide, an ethoxylated alcohol and ethoxylated acid.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof. Suspensions may also include dispersing agents such as lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The topical compositions of the present invention, comprise an active ingredient together with one or more acceptable carriers, and optionally any other therapeutic ingredients. Compositions suitable for topical administration include liquid or semi-liquid preparations suitable for penetration through the skin to the site of where treatment is required, such as liniments, lotions, creams, powders, patches, sprays, inhalers, ointments or pastes, and drops suitable for administration to the eye, ear or nose. The active ingredient is mixed under sterile conditions with a pharmaceutically acceptable carrier and any needed preservatives, buffers, or propellants which may be required.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

Compositions for rectal or vaginal administration are preferably suppositories which can be prepared by mixing the compounds with suitable non-irritating excipients or carriers such as cocoa butter, polyethylene glycol or a suppository wax which are solid at room temperature but liquid at body temperature and therefore melt in the rectum or vaginal cavity and release the active compound.

The amount of compound administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular compound administered, the mode of administration, the bioavailability of the preparation administered, the dose regime selected, the use of other medications and other relevant circumstances.

One skilled in the art would be able, by routine experimentation, to determine an effective, non-toxic amount of the compound which would be required to treat applicable diseases and conditions. Generally, a typical and effective dosage is expected to be in the range of about 0.01 to about 1000 mg per kilogram of body weight per day, typically of about 0.1 to about 100 mg per kilogram of body weight per day, even more typically of about 1 to about 10 mg per kilogram of body weight per day, and further of about 5 mg per kilogram of body weight per day. Small doses (0.01-1 mg/kg per day) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. A more preferred dosage will be in the range from 0.1 to 300 mg per kilogram of body weight per day, more preferably from 0.1 to 100 mg per kilogram of body weight per day. A suitable dose can be administered in multiple sub-doses per day.

Typically, in therapeutic applications, the treatment would be for the duration of the disease state.

Further, it will be apparent to one of ordinary skill in the art that the optimal quantity and spacing of individual dosages such as the number of doses of the composition given per day for a defined number of days will be determined by the nature and extent of the disease state being treated, the form, route and site of administration, and the nature of the particular individual being treated. Also, such optimum conditions can be determined by conventional techniques.

If desired, and for more effective distribution, the compounds can be incorporated into slow release or targeted delivery systems such as polymer matrices, liposomes, and microspheres.

Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable, of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

The compositions may be conjugated to an array of polyethylene glycol (PEG) derivatives. The addition of PEG to proteins (PEGylation) is a well established method for decreasing the plasma clearance rates of proteins, thereby increasing their efficacy (Nucci et al., 1991, *Adv. Drug Del. Rev.* 6:133). Additional benefits of PEGylation may include, greater stability of proteins, decreased immunogenicity, enhanced solubility and decreased susceptibility to proteolysis (Sheffield W. 2001, *Curr Drug Targets Cardiovasc Haematol Disord.* 1:1-22). PEG molecules contain the basic repeating structure of $-(OCH_3CH_2)n\text{-}OH$ and are classified into groups according to their molecular weight. PEG derivatives are conjugated to proteins to increase their hydrodynamic radius and in general, their increase in half-life is directly related to the size of the PEG chain attached (Sheffield W. 2001, *Curr Drug Targets Cardiovasc Haematol Disord.* 1:1-22).

The compositions may also be administered in the form of microparticles. Biodegradable microparticles formed from polylactide (PLA), polylactide-co-glycolide (PLGA), and epsilon-caprolactone (ε-caprolactone) have been extensively used as drug carriers to increase plasma half life and thereby prolong efficacy (R. Kumar, M., 2000, *J Pharm Pharmaceut Sci.* 3(2) 234-258). Microparticles have been formulated for the delivery of a range of drug candidates including vaccines, antibiotics, and DNA. Moreover, these formulations have been developed for various delivery routes including parenteral subcutaneous injection, intravenous injection and inhalation.

The compositions may incorporate a controlled release matrix that is composed of sucrose acetate isobutyrate (SAIB) and organic solvent or organic solvents mixture. Polymer additives may be added to the vehicle as a release modifier to further increase the viscosity and slow down the release rate. SAIB is a well known food additive. It is a very hydrophobic, fully esterified sucrose derivative, at a nominal ratio of six isobutyrate to two acetate groups. As a mixed ester, SAIB does not crystallize but exists as a clear viscous liquid. Mixing SAIB with a pharmaceutically accepted organic solvent such as ethanol or benzyl alcohol decreases the viscosity of the mixture sufficiently to allow for injection. An active pharmaceutical ingredient may be added to the SAIB delivery vehicle to form SAIB solution or suspension formulations. When the formulation is injected subcutaneously, the solvent diffuses from the matrix allowing the SAIB-drug or SAIB-drug-polymer mixtures to set up as an in situ forming depot.

Figure 1:
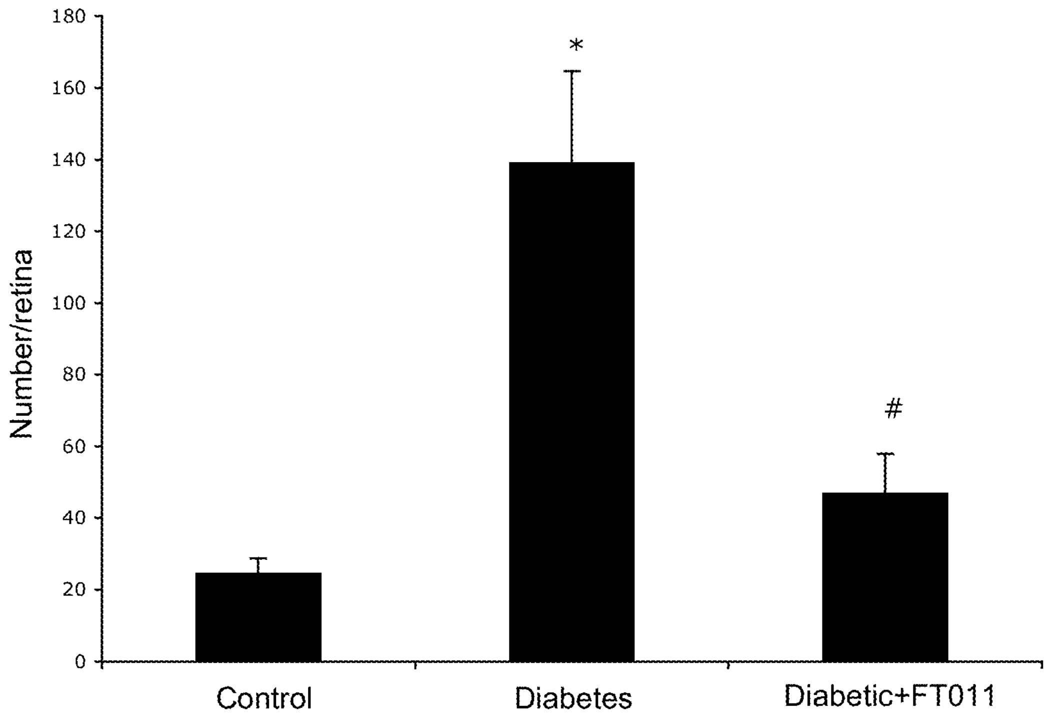
FIG. 1 is a graph depicting the number of leukocytes in the retina of control rats, diabetic rats and diabetic rats treated with FT011 from the short term study. Data were expressed mean±SEM. *P<0.05 versus control and # P<0.05 versus diabetes.

Embodiments of the invention will now be discussed in more detail with reference to the following examples and figures which are provided for exemplification only and which should not be considered limiting on the scope of the invention in any way.

Examples

Animals

The animal studies were conducted with the approval from the Animal Welfare and Ethics Committee (St Vincent's Hospital and the National Health and Medical Research Foundation of Australia). All rats received normal rat chow (Certified Rodent Diet #5002, LabDiet, USA) and drinking water ad libitum. All animals were housed in a stable environment maintained at 22±1° C. with a 12-hour light/dark cycle commencing at 6 am.

Example 1

Test Compound (FT011)

(E)-2-[[3-(3-Methoxy-4-propargyloxy)phenyl)-1-oxo-2-propenyl]amino]benzoic acid (FT011) has the structure:

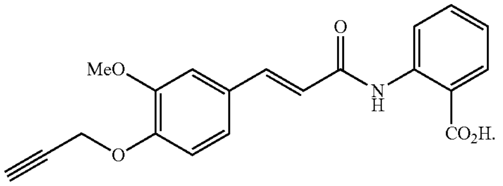 [SMILES: C#CCOc1ccc(/C=C/C(=O)Nc2ccccc2C(=O)O)cc1OC]

Diabetic Retinopathy Rats

Ninety, six-week old female, heterozygous (mRen-2)27 rats (St. Vincent's Hospital Animal House, Melbourne, Australia) were assigned to receive either 55 mg/kg of streptozotocin (STZ) (Sigma, St. Louis, USA) diluted in 0.1 M citrate buffer, pH 4.5 or citrate buffer alone (non-diabetic control) by tail vein injection following an overnight fast. In short term study, rats were randomly assigned to receive (n=10/group) treatment with either FT011 (100 mg/kg bid gavage) or vehicle for 8 weeks. Non-diabetic animals (n=10) served as controls.

In the long term study, at 16 weeks of STZ diabetes rats were randomly assigned to either treatment (n=15/group) with, FT011 (50 mg/kg/day BID), FT011 (100 mg/kg BID) or no treatment for a further 16 weeks. Non-diabetic animals (n=15) served as controls. Each week, rats were weighed and their blood glucose levels were measured (Accu-check Advantage II Blood Glucose Monitor, Roche Diagnostics, USA) and only STZ-treated animals with blood glucose>15 mmol/L were considered diabetic. Every 4 weeks, SBP was determined in preheated conscious rats via tail-cuff plethysmography using a non-invasive blood pressure (NIBP) controller and Powerlab (AD instruments, NSW, Australia). Haemoglobin A1c (HbA1c) was measured by HPLC at the end of the study in the Department of Pathology, St Vincent's Hospital. Diabetic rats received a daily injection of insulin (2-4 units intraperitoneally; Humulin NPH, Eli Lilly and Co., Indianapolis, Ind.) to reduce mortality and to promote weight gain.

Leukostasis (Short Term Study)

At the end of the short term 8 week study, rats were anaesthetized with Lethobarb (60 mg/kg) and the chest cavity was opened. Animals were perfused via the left ventricle with 0.1M phosphate buffered saline (PBS) to remove non-adherent blood cells. The rats were then perfused with rhodamine-coupled Concanavalin A (25 mg/kg, Vector Laboratories) to stain endothelium and adherent leukocytes. Eyes were enucleated and fixed with 4% paraformaldehyde in 0.1M PBS for 30 minutes. Retinae were dissected and flat mounted on microscope slides then visualised on an epi-fluorescent microscope. The total number of leukocytes was counted per retina. The investigator was masked to the group.

Real Time PCR (Short Term Study)

At the end of the short term 8 week study, rats were anaesthetized with lethobarb (60 mg/kg), eyes were enucleated and retinae dissected and placed in RNAlater (# R0901, Sigma-Aldrich). Total RNA was extracted with an RNeasy Mini Kit (#74104, Qiagen) according to manufacturers' instructions. RNA concentration was determined on a Nanodrop 3.1.2, after which 1 μg of RNA was DNase treated (DNA-free kit, Ambion) and reverse transcribed (First Strand cDNA Synthesis Kit for RT-PCR, Roche). Primers, probes (See Table) and cDNA were mixed with Taqman Universal Master Mix (#4304437, Applied Biosystems) and real-time PCR was conducted using an ABI 7900 HT Sequence Detection System (Applied Biosystems). mRNA was normalised to 18S rRNA endogenous control and the relative fold difference in expression calculated using the $2^{-\Delta\Delta}$CT method.

Primer and Probe for ICAM-1

| Gene | Species | Accession number | Primers and Taqman probe (MGB, FAM label) |
|---|---|---|---|
| ICAM1 | rat | NM_012967 | Forward Primer: AGTGCTGTACCATGAT CAGAATACCT Probe: TGA TCATTGCGGGCT Reverse Primer: TAAATGGACGCCACGA TCAC |
| 18S | eukaryote | X03205.1 | Applied Biosystems gene expression assay - endogenous control - VIC label |

Trypsin Digest (Long Term Study 32 Weeks)

At the end of long term 32 week study, rats were anaesthetised with Lethobarb (60 mg/kg), and then eyes were enucleated and fixed in 2% Carsons Fixative overnight. Retinae were dissected and washed in 0.2M Tris Buffer (pH 8.0) followed by digestion in 1% Trypsin (# T4799, Sigma-Aldrich) in 0.2M Tris buffer at 37° C. for one hour. Retinae were then incubated in 1% Triton X in 0.2M Tris buffer for approximately one hour. Subsequently, retinae were flat mounted on a microscope slide and dried overnight. Slides were stained with Periodic Acid Schiff's Stain to observe acellular capillaries.

Quantification was performed by scanning the entire retina with a 10× objective on a Zeiss Observer microscope system. Random 600 μm×800 μm fields were placed over the entire retina using Adobe Photoshop CS2. Acellular capillaries were counted per field with 10 retinae per group quantitated. Investigators were masked to the group. Data was analysed as an average of acellular capillaries per field.

Statistics

Statistics were performed using the Shapiro Wilkinson test for normality. A Krukal-Wallis test followed by Mann Whitney U test was performed for statistical significance of nonparametric data.

Results

TABLE 1

Animal characteristics (8 weeks study)

| Group | Body Weight (g) | SBP (mmHg) | HbA1C (%) |
|---|---|---|---|
| Control | 289 ± 4 | 179 ± 8 | 3.7 ± 0.06 |
| Diabetes | 274 ± 6 | 217 ± 10* | 11 ± 0.19** |
| Diabetic + FT011 (200 mg/kg/day) | 278 ± 12 | 190 ± 14 | 8.9 ± 0.50# |

*P < 0.05 and
**P < 0.01 versus control;
#P < 0.05 versus untreated diabetes

TABLE 2

Animal characteristics (32 weeks study)

| Group | Body Weight (g) | SBP (mmHg) | HbA1C (%) |
|---|---|---|---|
| Control | 353 ± 11 | 152 ± 7 | 5.4 ± 0.5 |
| Diabetes | 324 ± 7 | 160 ± 8 | 8.4 ± 0.29* |
| Diabetic + FT011 (100 mk/kg/day) | 322 ± 8 | 176 ± 10 | 7.65 ± 0.25* |
| Diabetic + FT011 (200 mk/kg/day) | 313 ± 9 | 170 ± 7 | 6.58 ± 0.37# |

*P < 0.05 versus control;
#P < 0.05 versus untreated diabetes

FIG. 1 demonstrates the total number of leukocytes in the retina from the short term study were significantly less in diabetic rats treated with FT011 compared to untreated diabetic rats.

Figure 2:
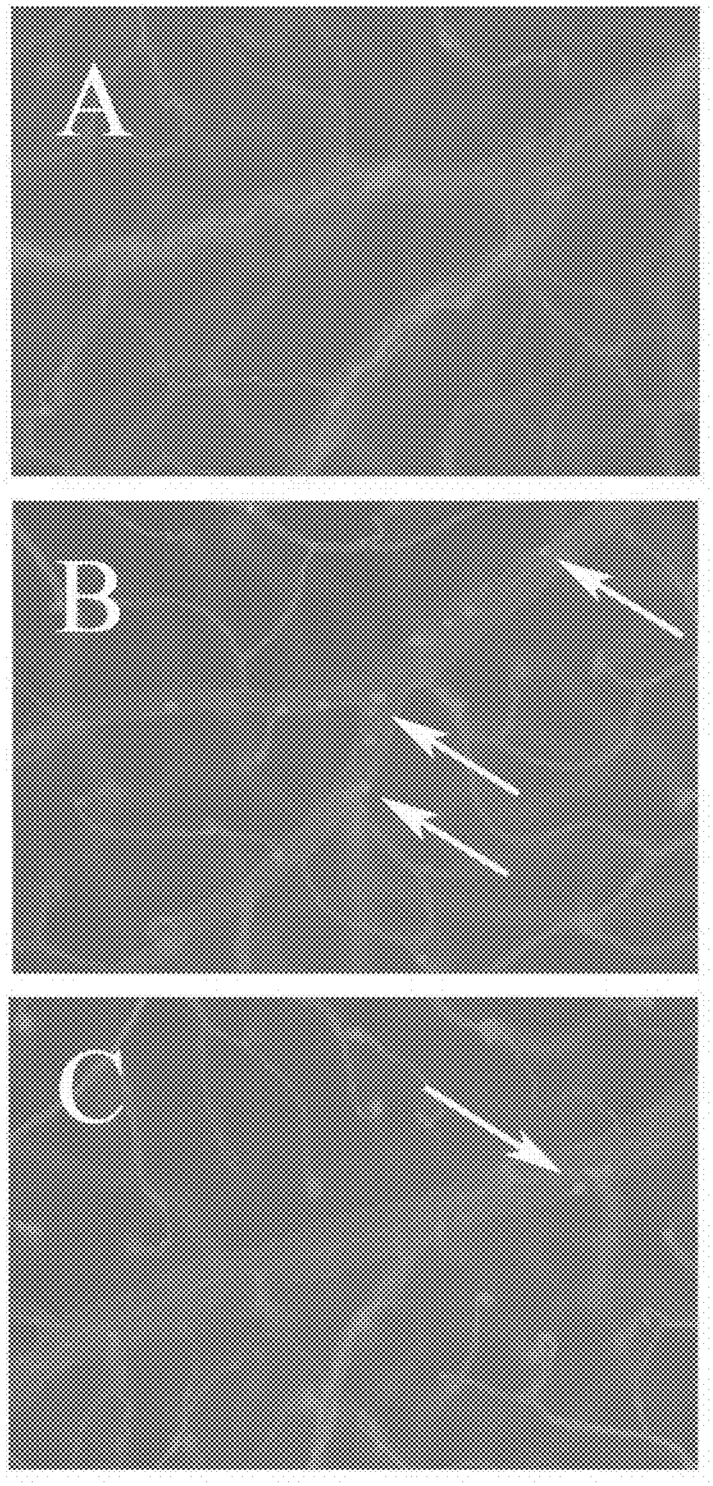
FIG. 2 illustrates representative photomicrographs of rhodamine-coupled Concanavalin A stained for endothelium and adherent leukocytes from retina of control rats (A), diabetic rats (B) and diabetic rats treated with FT011 (C).

The representative micrographs in FIG. 2 show that in diabetic rats (B) numerous leukocytes were observed in the capillaries (designated with arrows) when compared to control (A), and treatment with FT011 significantly reduced leukostasis (C).

Figure 3:
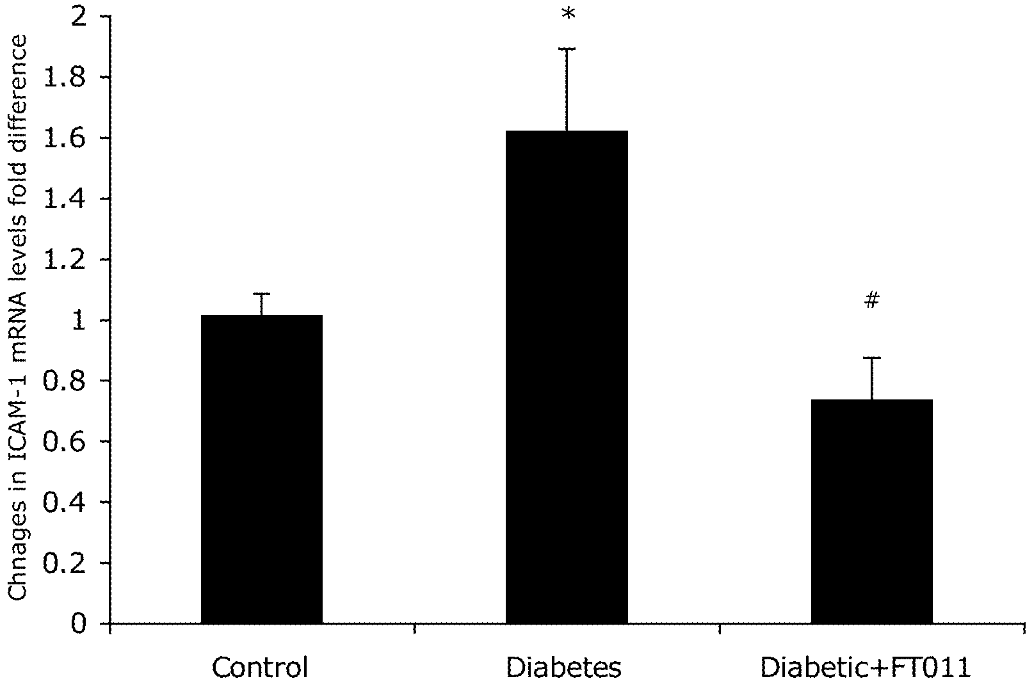
FIG. 3 is a graph showing changes in retinal ICAM-1 mRNA levels in control rats, diabetic rats and diabetic rats treated with FT011. Data were expressed mean±SEM. *P<0.05 versus control and # P<0.05 versus diabetes.

FIG. 3 shows there was an increase in ICAM-1 mRNA levels in diabetic rats when compared to controls. Moreover, treatment with FT011 was associated with a reduction in ICAM-1 mRNA levels.

Figure 4:
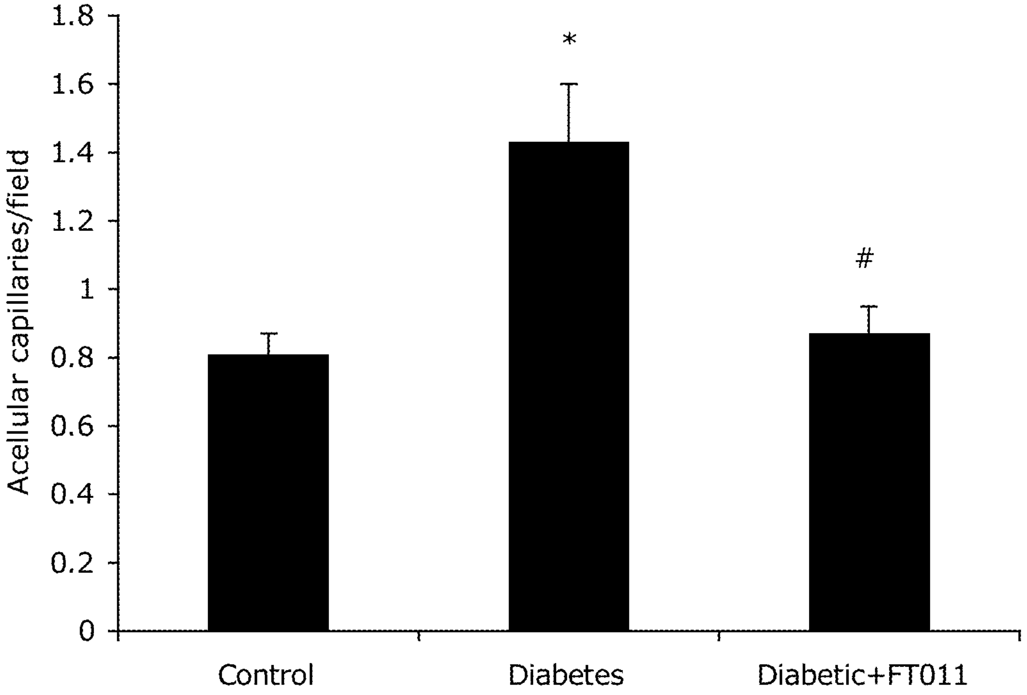
FIG. 4 is a graph illustrating the number of acellular capillaries in PAS stained retinal sections from control rats, diabetic rats and diabetic rats treated with 100 mg/kg/day FT011 from a long term study. Acellular capillaries were expressed as number of acellular capillaries per field. Data were expressed mean±SEM. *P<0.05 versus control and # P<0.05 versus diabetes.

In FIG. 4 a quantitative assessment of acellular capillaries was made by counting the number of capillaries in PAS stained retinal sections from the long term study. Clearly, there were less acellular capillaries in diabetic rats treated with FT011 compared to untreated diabetic rats.

Figure 5:
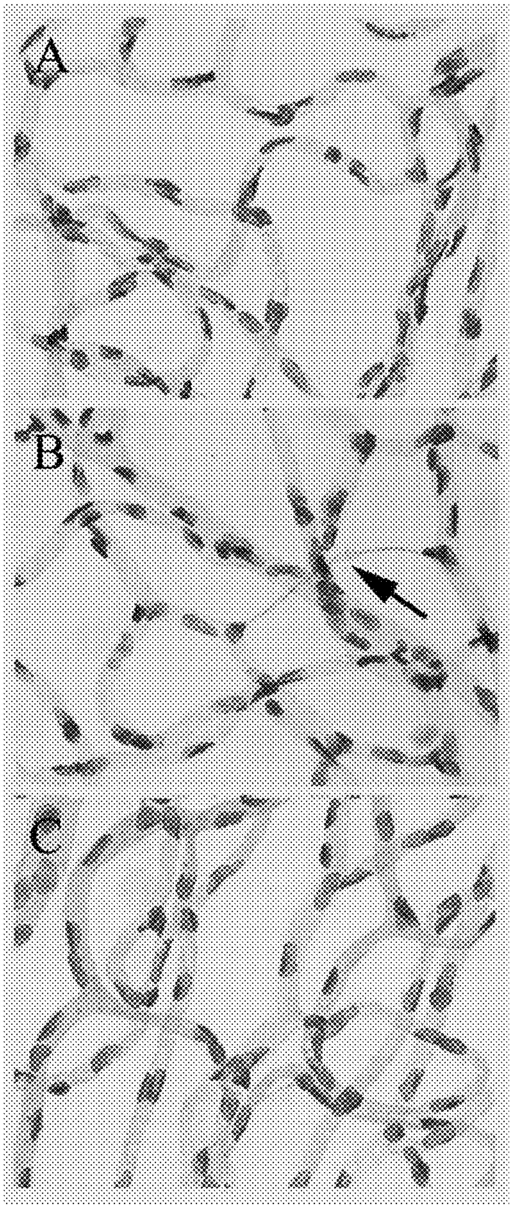
FIG. 5 illustrates representative photomicrographs of acellular capillaries from PAS stained retina of control rats (A), diabetic rats (B) and diabetic rats treated with 100 mg/kg/day FT011 (C).

The representative micrographs in FIG. 5 show that In diabetic rats (B) acellular capillaries (pericyte ghost) were observed (arrow), while pericyte ghosts were not apparent in control (A) and diabetic rats treated with FT011 (C).

Example 2

Test Compound (FT061)

(E)-2-[[3,4-Bis(difluoromethoxy)phenyl)-1-oxo-2-propenyl]amino]benzoic acid (FT061) has the structure:

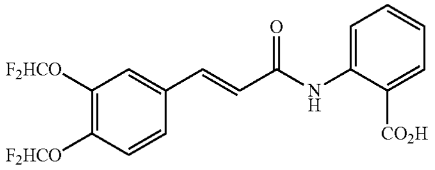 [SMILES: O=C(/C=C/c1ccc(OC(F)F)c(OC(F)F)c1)Nc1ccccc1C(=O)O]

Diabetic Retinopathy Rats

Sixty, six-week old female, heterozygous (mRen-2)27 rats (St. Vincent's Hospital Animal House, Melbourne, Australia) were assigned to receive either 55 mg/kg of streptozotocin (STZ) (Sigma, St. Louis, USA) diluted in 0.1 M citrate buffer, pH 4.5 or citrate buffer alone (non-diabetic control) by tail vein injection following an overnight fast. Rats were randomly assigned to receive (n=15/group) treatment with either FT061 (100 mg/kg/day gavage) or vehicle for 8 weeks. Non-diabetic animals (n=15) served as controls. Each week, rats were weighed and their blood glucose levels were measured (Accu-check Advantage II Blood Glucose Monitor, Roche Diagnostics, USA) and only STZ-treated animals with blood glucose>15 mmol/L were considered diabetic. Every 4 weeks, SBP was determined in preheated conscious rats via tail-cuff plethysmography using a non-invasive blood pressure (NIBP) controller and Powerlab (AD instruments, NSW, Australia). Diabetic rats received a daily injection of insulin (2-4 units intraperitoneally; Humulin NPH, Eli Lilly and Co., Indianapolis, Ind.) to reduce mortality and to promote weight gain.

Leukostasis

At the end of the study, rats were anaesthetized with Lethobarb (60 mg/kg) and the chest cavity was opened. Animals were perfused via the left ventricle with 0.1M phosphate buffered saline (PBS) to remove non-adherent blood cells. The rats were then perfused with rhodamine-coupled Concanavalin A (25 mg/kg, Vector Laboratories) to stain endothelium and adherent leukocytes. Eyes were enucleated and fixed with 4% paraformaldehyde in 0.1M PBS for 30 minutes. Retinae were dissected and flat mounted on microscope slides then visualised on an epi-fluorescent microscope. The total number of leukocytes was counted per retina. The investigator was masked to the group.

Real Time PCR

At the end of the study, rats were anaesthetized with lethobarb (60 mg/kg), eyes were enucleated and retinae dissected and placed in RNAlater (# R0901, Sigma-Aldrich). Total RNA was extracted with an RNeasy Mini Kit (#74104, Qiagen) according to manufacturers' instructions. RNA concentration was determined on a Nanodrop 3.1.2, after which 1 g of RNA was DNase treated (DNA-free kit, Ambion) and reverse transcribed (First Strand cDNA Synthesis Kit for RT-PCR, Roche). Primers, probes (See Table) and cDNA were mixed with Taqman Universal Master Mix (#4304437, Applied Biosystems) and real-time PCR was conducted using an ABI 7900 HT Sequence Detection System (Applied Biosystems). mRNA was normalised to 18S rRNA endogenous control and the relative fold difference in expression calculated using the $2^{-\Delta\Delta}$CT method.

Primer and Probe for ICAM-1 and VEGF

| Gene | Species | Accession number | Primers and Taqman probe (MGB, FAM label) |
|---|---|---|---|
| ICAM1 | rat | NM_012967 | Forward Primer: AGTGCTGTACCATGAT CAGAATACCT Probe: TGA TCATTGCGGGCT Reverse Primer: TAAATGGACGCCACGA TCAC |
| VEGF | rat | NM_031836.2 NM_001110333.1 NM_001110334.1 | Applied Biosystems gene expression assay - FAM label |
| 18S | eukaryote | X03205.1 | Applied Biosystems gene expression assay - endogenous control - VIC label |

Statistics

Statistics were performed using the Shapiro Wilkinson test for normality. A Krukal-Wallis test followed by Mann Whitney U test was performed for statistical significance of nonparametric data.

Results

TABLE 1

| Animal characteristics | | |
|---|---|---|
| Group | Body Weight (g) | SBP (mmHg) |
| Control | 308 ± 8 | 192 ± 6 |
| Diabetes | 292 ± 10 | 201 ± 10 |
| Diabetic + FT061 | 282 ± 4# | 178 ± 4 |

#P < 0.05 versus control

Figure 6:
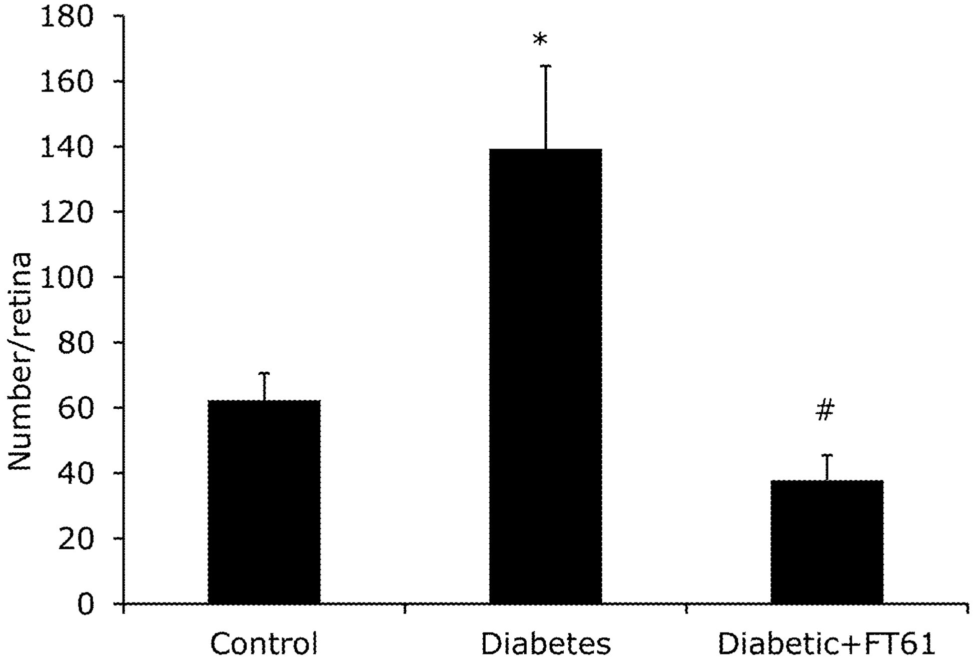
FIG. 6 is a graph depicting the number of leukocytes in the retina of control rats, diabetic rats and diabetic rats treated with FT061. Data were expressed mean±SEM. *P<0.05 versus control and # P<0.05 versus untreated diabetes.

FIG. 6 demonstrates the total number of leukocytes in the retina was significantly less in diabetic rats treated with FT061 compared to untreated diabetic rats.

Figure 7:
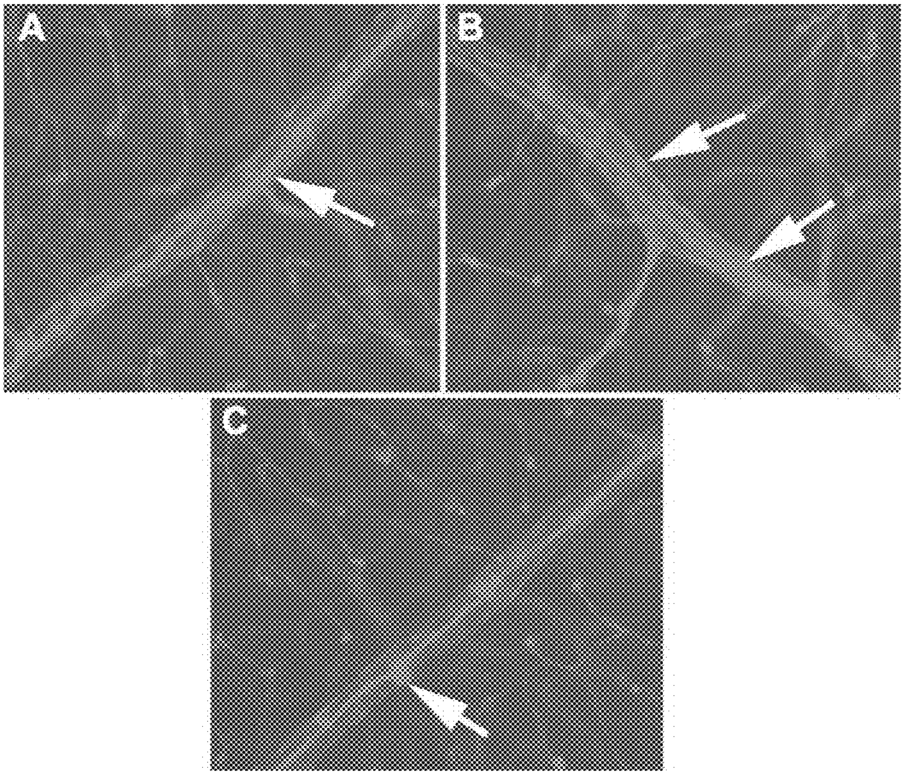
FIG. 7 illustrates representative photomicrographs of rhodamine-coupled Concanavalin A stained for endothelium and adherent leukocytes from retina of control rats (A), diabetic rats (B) and diabetic rats treated with FT061 (C).

The representative photomicrographs in FIG. 7 show that in diabetic rats (B) numerous leukocytes were observed in the capillaries (designated with arrows) when compared to control (A), and treatment with FT061 significantly reduced leukostasis (C).

Figure 8:
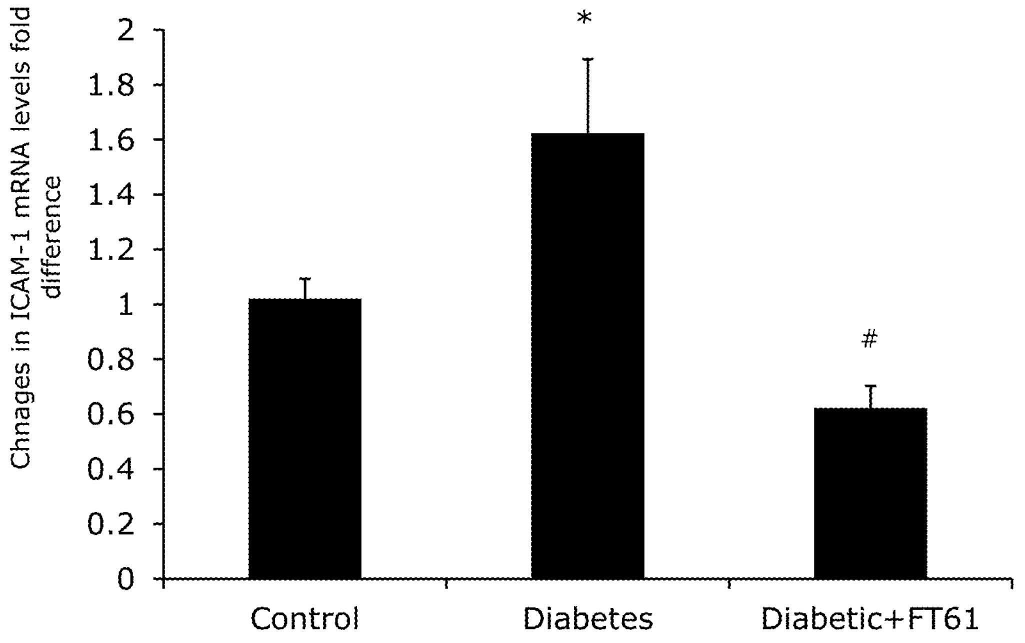
FIG. 8 is a graph showing changes in retinal ICAM-1 mRNA levels in control rats, diabetic rats and diabetic rats treated with FT061. Data were expressed mean±SEM. *P<0.05 versus control and # P<0.05 versus untreated diabetes.

FIG. 8 illustrates a quantitative real time PCR assessment of retinal ICAM-1 mRNA levels. FIG. 8 shows there was an increase in ICAM-1 mRNA levels in diabetic rats compared to controls. Moreover, treatment with FT061 was associated with a reduction in ICAM-1 mRNA levels when compared to controls and untreated diabetes.

Figure 9:
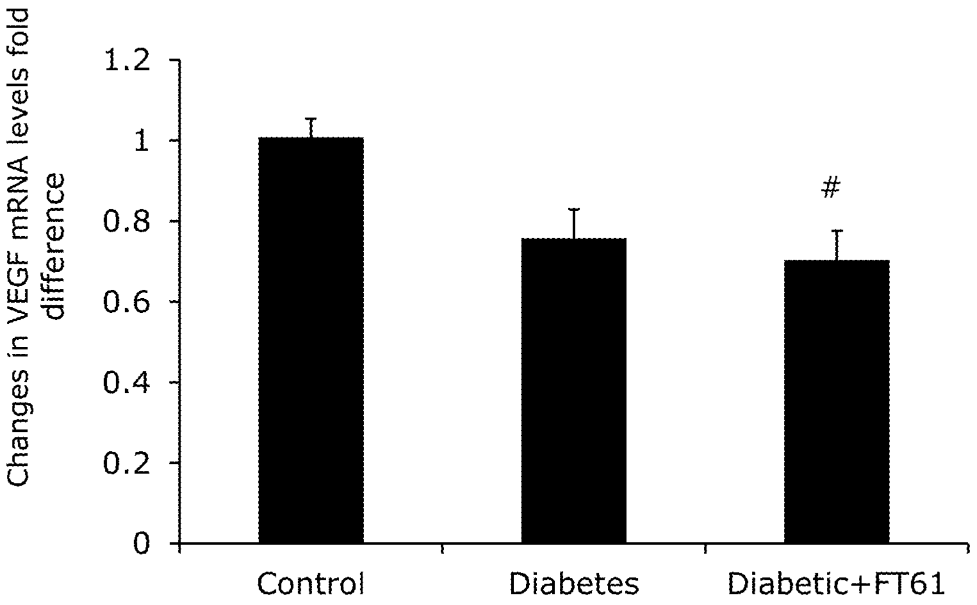
FIG. 9 is a graph illustrating changes in retinal VEGF mRNA levels in control rats, diabetic rats and diabetic rats treated with FT061. Data were expressed mean±SEM. # P<0.05 versus control.

In FIG. 9 a quantitative real time PCR assessment of retinal VEGF mRNA levels showed treatment with FT061 was associated with a reduction in VEGF mRNA levels when compared to controls and untreated diabetes.

It will of course be realised that the above has been given only by way of illustrative example of the invention and that all such modifications and variations thereto as would be apparent to persons skilled in the art are deemed to fall within the broad scope and ambit of the invention as herein set forth.

REFERENCES

Adamis, A. P. (2002). "Is diabetic retinopathy an inflammatory disease?" *Br J Ophthalmol* 86(4): 363-5.

Aiello, L. M. (2003). "Perspectives on diabetic retinopathy." *Am J Ophthalmol* 136(1): 122-35.

Arita, R., Y. Hata, et al. "ROCK as a Therapeutic Target of Diabetic Retinopathy." *J Ophthalmol* 2010: 175163.

Cheung, A. K., M. K. Fung, et al. (2005). "Aldose reductase deficiency prevents diabetes-induced blood-retinal barrier breakdown, apoptosis, and glial reactivation in the retina of db/db mice." *Diabetes* 54(11): 3119-25.

Joussen, A. M., V. Poulaki, et al. (2004). "A central role for inflammation in the pathogenesis of diabetic retinopathy." *Faseb J* 18(12): 1450-2.

Joussen, A. M., V. Poulaki, et al. (2002). "Nonsteroidal anti-inflammatory drugs prevent early diabetic retinopathy via TNF-alpha suppression." *Faseb J.* 16(3): 438-40.

Joussen, A. M., V. Poulaki, et al. (2002). "Retinal vascular endothelial growth factor induces intercellular adhesion molecule-1 and endothelial nitric oxide synthase expression and initiates early diabetic retinal leukocyte adhesion in vivo." *Am J Pathol* 160(2): 501-9.

Khalfaoui, T., G. Lizard, et al. (2009). "Immunohistochemical analysis of cellular adhesion molecules (ICAM-1, VCAM-1) and VEGF in fibrovascular membranes of patients with proliferative diabetic retinopathy: preliminary study." *Pathol Biol* (*Paris*) 57(7-8): 513-7.

Klein, R., B. E. Klein, et al. (2004). "The relation of retinal vessel caliber to the incidence and progression of diabetic retinopathy: XIX: the Wisconsin Epidemiologic Study of Diabetic Retinopathy." *Arch Ophthalmol* 122(1): 76-83.

Santos, K. G., B. Tschiedel, et al. (2005). "Prevalence of retinopathy in Caucasian type 2 diabetic patients from the South of Brazil and relationship with clinical and metabolic factors." *Braz J Med Biol Res* 38(2): 221-5.

Sarlos, S., B. Rizkalla, et al. (2003). "Retinal angiogenesis is mediated by an interaction between the angiotensin type 2 receptor, VEGF, and angiopoietin." *Am J Pathol* 163(3): 879-87.

Watkins, P. J. (2003). "Retinopathy." *Bmj* 326(7395): 924-6.

Zammit, S. C., A. J. Cox, et al. (2009). "Evaluation and optimization of antifibrotic activity of cinnamoyl anthranilates." *Bioorg Med Chem Lett* 19(24): 7003-6.

The claims defining the invention are as follows:

1. A method for inhibiting the progression of and/or ameliorating a symptom of age-related macular degeneration associated with vascular proliferation in a subject comprising administering orally to the subject a therapeutically effective amount of a compound of the formula

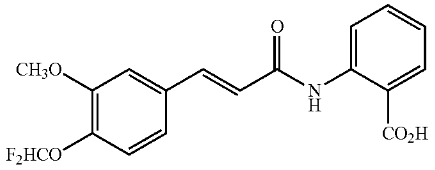

or a pharmaceutically acceptable salt thereof.

* * * * *